United States Patent
Ben Neriah et al.

(10) Patent No.: US 10,960,003 B2
(45) Date of Patent: *Mar. 30, 2021

(54) PYRAZOLE PYRIMIDINE DERIVATIVE AND USES THEREOF

(71) Applicant: Yissum Research Development Company of the Hebrew University of Jerusalem LTD, Jerusalem (IL)

(72) Inventors: Yinon Ben Neriah, Mevasseret Zion (IL); Guy Brachya, Jerusalem (IL); Ido Burstain, Moshav Sde-Yaakov (IL); Waleed Minzel, Kafr-Kanna (IL); Irit Snir-Alkalay, Mevasseret Zion (IL); Joseph Vacca, Telford, PA (US); Dansu Li, Warrington, PA (US)

(73) Assignee: BioTheryX, Inc., Chappaqua, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/538,550

(22) Filed: Aug. 12, 2019

(65) Prior Publication Data

US 2019/0365759 A1    Dec. 5, 2019

Related U.S. Application Data

(63) Continuation of application No. 15/748,536, filed as application No. PCT/IL2016/050852 on Aug. 4, 2016, now Pat. No. 10,376,511.

(60) Provisional application No. 62/268,750, filed on Dec. 17, 2015, provisional application No. 62/200,846, filed on Aug. 4, 2015.

(51) Int. Cl.

| | | |
|---|---|---|
| *A61K 31/506* | (2006.01) | |
| *A61P 35/02* | (2006.01) | |
| *C07D 405/14* | (2006.01) | |
| *C07D 413/14* | (2006.01) | |
| *C07D 403/04* | (2006.01) | |

(52) U.S. Cl.
CPC .......... *A61K 31/506* (2013.01); *A61P 35/02* (2018.01); *C07D 403/04* (2013.01); *C07D 405/14* (2013.01); *C07D 413/14* (2013.01)

(58) Field of Classification Search
CPC ... C07D 405/14; C07D 413/14; C07D 403/04
See application file for complete search history.

(56) References Cited

U.S. PATENT DOCUMENTS

| | | | |
|---|---|---|---|
| 10,376,511 B2* | 8/2019 | Ben Neriah | ......... A61K 31/506 |
| 2015/0094305 A1 | 4/2015 | Romero et al. | |
| 2015/0202205 A1 | 7/2015 | Baldino et al. | |

FOREIGN PATENT DOCUMENTS

| | | |
|---|---|---|
| WO | 2002092573 A2 | 11/2002 |
| WO | 2005095357 A2 | 10/2005 |
| WO | 2007/129195 A2 | 11/2007 |
| WO | 2015/058140 A1 | 4/2015 |

OTHER PUBLICATIONS

Adams et al., "IRAK1 is a novel DEK transcriptional target and is essential for head and neck cancer cell survival," Oncotarget 2015, 6:43395-43407.
Amit et al., "Axin-mediated CKI phosphorylation of beta-catenin at Ser 45: a molecular switch for the Wnt pathway," Genes Dev. 2002, 16:1066-1076.
Aran et al., "Widespread parainflammation in human cancer," Genome Biol. 2016, 17:145.
Bahia et al., "Interleukin-1 receptor associated kinase inhibitors: potential therapeutic agents for inflammatory- and immune-related disorders," Cell Signal. 2015, 27:1039-1055.
Berge et al., "Pharmaceutical salts," J. Pharm. Sci. 1977, 66:1-19.
Cheong et al., "Casein kinase 1: Complexity in the family," Int. J. Biochem. Cell Biol. 2011, 43:465-469.
Clevers et al., "Wnt/β-catenin signaling and disease," Cell 2012, 149:1192-1205.
Duan et al., "mTOR generates an auto-amplification loop by triggering the βTrCP- and CK1α-dependent degradation of DEPTOR," Mol. Cell 2011, 44:317-324.
Elyada et al., "CKIα ablation highlights a critical role for p53 in invasiveness control," Nature 2011, 470:409-413.
Fabian et al., "A small molecule-kinase interaction map for clinical kinase inhibitors," Nat. Biotechnol. 2005, 23:329-336.
Fish et al., "Isolation and characterization of human casein kinase I epsilon (CKI), a novel member of the CKI gene family," J. Biol. Chem. 1995, 270:14875-14883.
Karaman et al., "A quantitative analysis of kinase inhibitor selectivity," Nat. Biotechnol. 2008, 26:127-132.
Knippschild et al., "The casein kinase 1 family: participation in multiple cellular processes in eukaryotes," Cell Signal 2005, 17:675-689.
Lasry et al., "Senescence-associated inflammatory responses: aging and cancer perspectives," Trends Immunol. 2015, 36:217-228.
Pribluda et al., "A senescence-inflammatory switch from cancer-inhibitory to cancer-promoting mechanism," Cancer Cell 2013, 24:242-256.
Rhyasen et al., "Targeting IRAK1 as a therapeutic approach for myelodysplastic syndrome," Cancer Cell 2013, 24:90-104.

(Continued)

*Primary Examiner* — Mark L Shibuya
*Assistant Examiner* — Ebenezer O Sackey
(74) *Attorney, Agent, or Firm* — Lin Yu, Esq.; Juniv LLP

(57) ABSTRACT

The present invention provides pyrazole pyrimidine derivatives which inhibit Casein kinase I (CKI) and/or Interleukin-1 receptor-associated kinase 1 (IRAKI) and methods of their manufacture, compositions comprising them and uses thereof in methods of treating malignant disease and disorders and methods for treating inflammatory diseases and disorders.

20 Claims, 16 Drawing Sheets

(56) References Cited

OTHER PUBLICATIONS

Rhyasen et al., "Differential IRAK signaling in hematologic malignancies," Exp. Hematol. 2013, 41:1005-1007.
Sansom et al., "Loss of Apc in vivo immediately perturbs Wnt signaling, differentiation, and migration," Genes Dev. 2004, 18:1385-1390.
Schittek et al., "Biological functions of casein kinase 1 isoforms and putative roles in tumorigenesis," Mol. Cancer 2014, 13:231.
Wee et al., "IRAK1 is a therapeutic target that drives breast cancer metastasis and resistance to paclitaxel," Nat. Commun. 2015, 6:8746.
Zemp et al., "CK1σ and CK1ε are components of human 40S subunit precursors required for cytoplasmic 40S maturation," J. Cell Sci. 2014, 127:1242-1253.

* cited by examiner

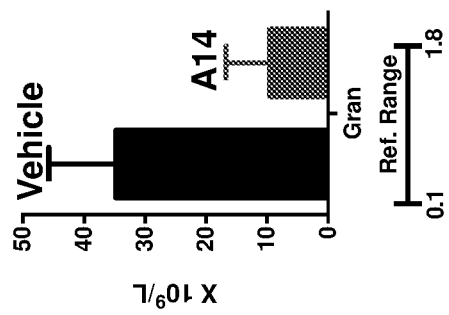
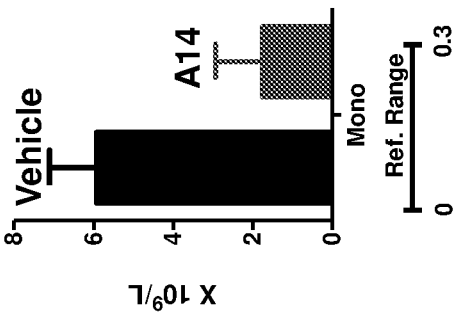
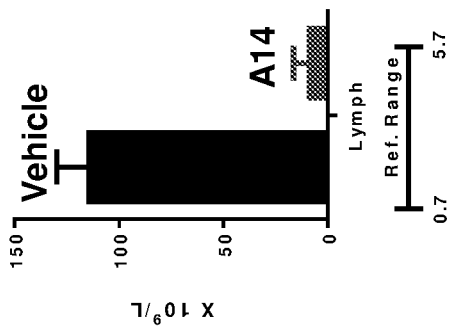
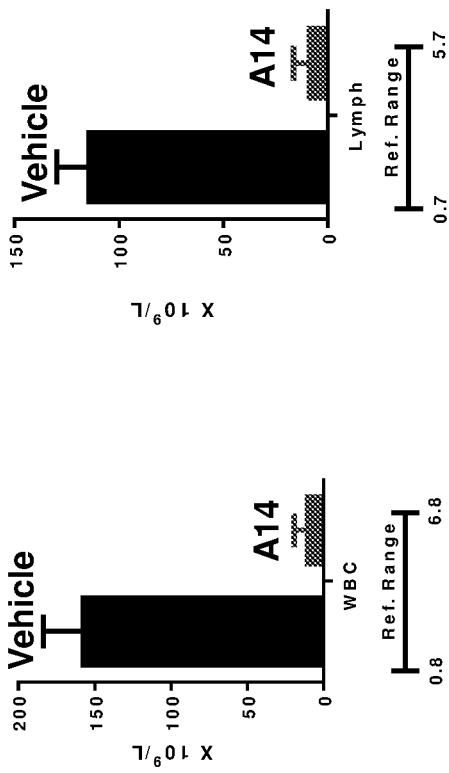
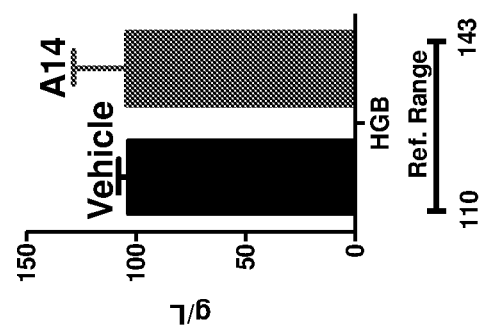
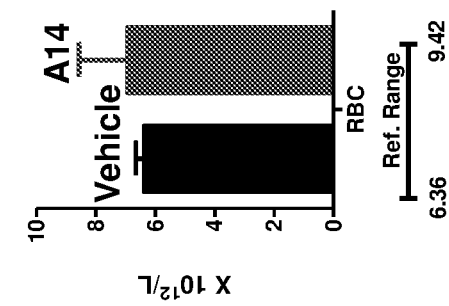

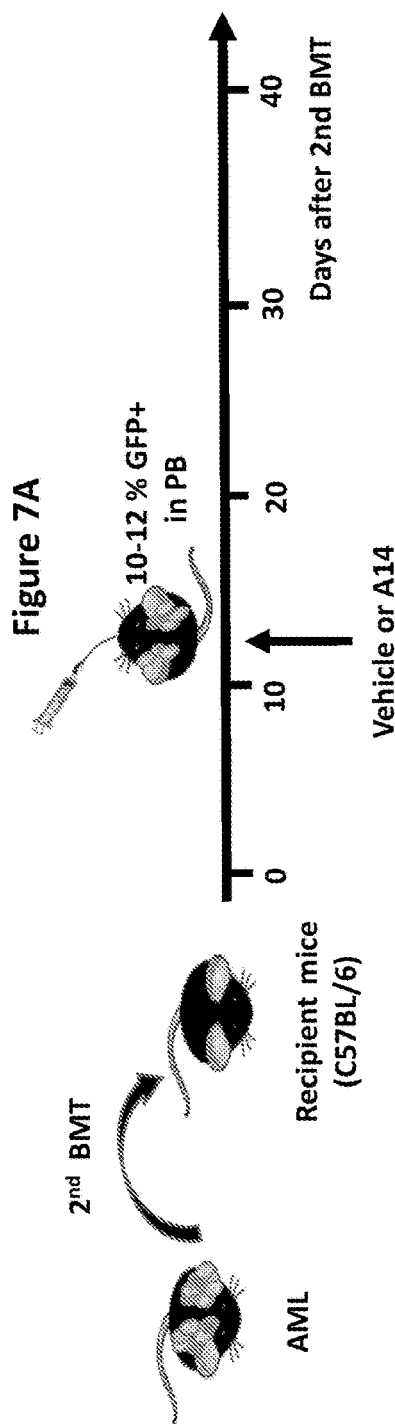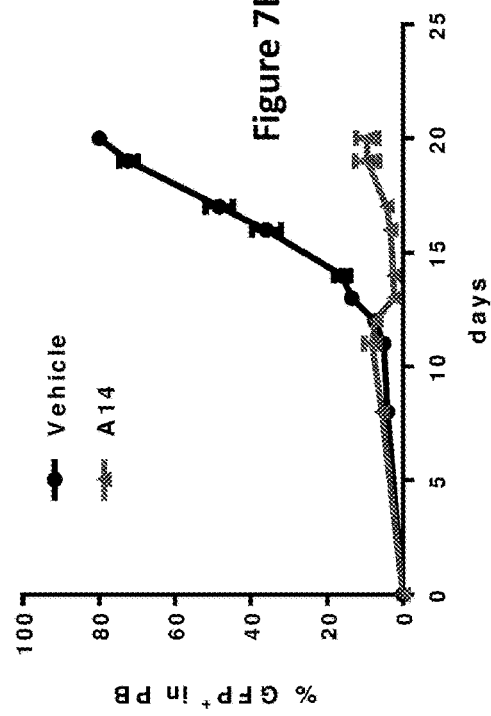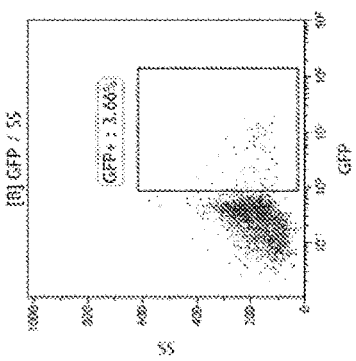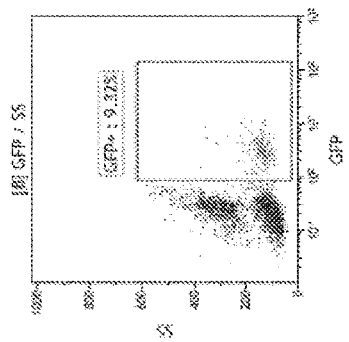

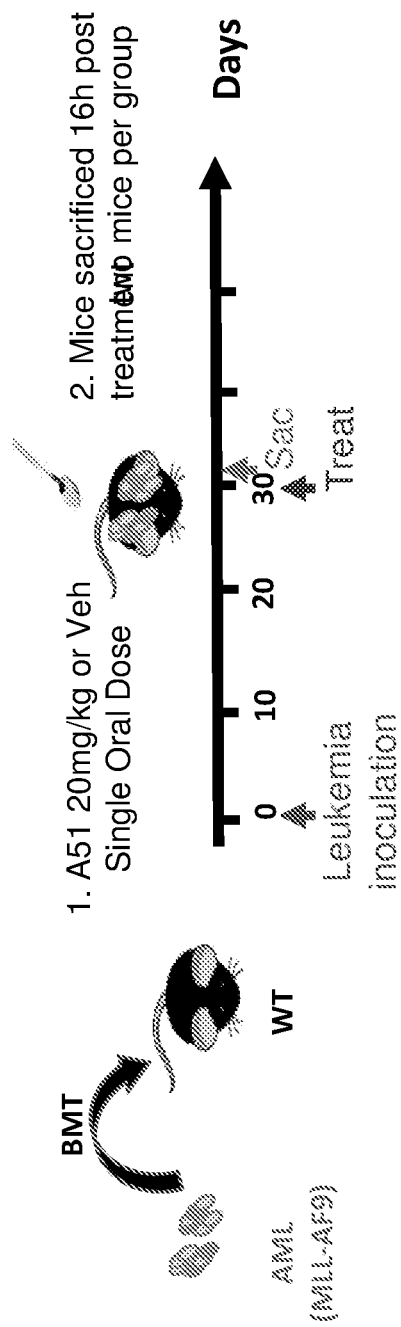
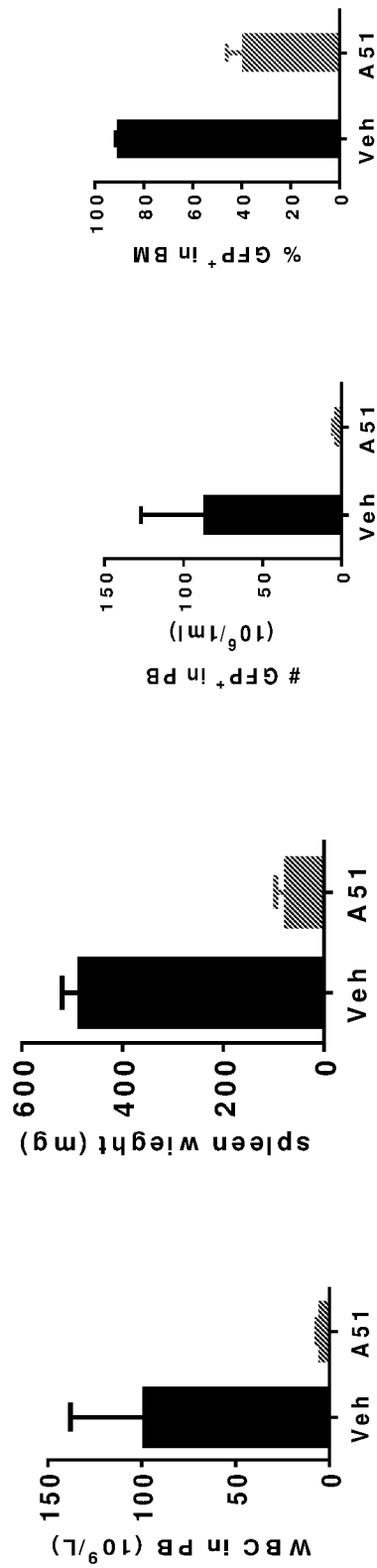
Figure 11A
Figure 11B
Figure 11C
Figure 11D
Figure 11E

PYRAZOLE PYRIMIDINE DERIVATIVE AND USES THEREOF

CROSS REFERENCE TO RELATED APPLICATIONS

This application is a continuation of U.S. application Ser. No. 15/748,536; which is a National Stage of International Application No. PCT/IL2016/050852, filed Aug. 4, 2016; which claims the benefit of the priority of U.S. Provisional Application Nos. 62/200,846, filed Aug. 4, 2015, and 62/268,750, filed Dec. 17, 2015; the disclosure of each of which is incorporated herein by reference in its entirety.

TECHNOLOGICAL FIELD

The present invention provides pyrazole pyrimidine derivatives and uses thereof in methods of treating malignant disease and disorders and methods for treating inflammatory diseases and disorders.

BACKGROUND

The casein kinase 1 family (CK1, or CKI) are serine/threonine kinases with six members (isoforms) in humans: $\alpha$, $\gamma 1$, $\gamma 2$, $\gamma 3$, $\delta$ and $\epsilon$. They differ in length and sequence of the N-terminal (9-76 amino acids) and especially the C-terminal (24-200 amino acids) non-catalytic domain (Schittek and Sinnberg, Molecular Cancer 2014, 13:231).

CK1$\delta$ and CK1$\epsilon$ are 98% identical in their kinase domain and 53% identical in their C-terminal regulatory domain (Fish K J et al. J Biol Chem 1995, 270:14875-14883). Whereas, there is some redundancy with respect to CK1 substrate phosphorylation, most CK1 isoforms have distinct biological roles. The wide range of CK1 substrates shows that the CK1 family members are involved in multiple cellular processes, from regulation of membrane trafficking, cytokinesis, vesicular transport, ribosome biogenesis, DNA repair, signal transduction pathways, apoptosis and in the circadian rhythm (Knippschild U et al. Cell Signal 2005, 17:675-689; Cheong J K and Virshup D M. Int J Biochem Cell Biol 2011, 43:465-469; Zemp I, et al. J Cell Sci 2014, 127:1242-1253).

CK1$\alpha$ plays a role in the mitotic spindle formation during cell division and in DNA repair mechanisms and participates in RNA metabolism (Knippschild U et al. Cell Signal 2005, 17:675-689). It contributes to the activation of mTOR via sustained degradation of the endogenous mTOR inhibitor DEPTOR (Duan S et al. Mol Cell 2011, 44:317-324).

CK1$\alpha$ has a major role in regulation of the Wnt/$\beta$-catenin signaling pathway. The inventors of this application have shown that CK1$\alpha$ is a key component of the $\beta$-catenin destruction complex. When the Wnt receptors are not engaged, CK1$\alpha$ phosphorylates $\beta$-catenin at serine residue S45, which is necessary for the priming phosphorylation of another kinase, GSK3 (Amit et al. Genes Dev. 2002 16: 1066-1076).

$\beta$-catenin phosphorylation by GSK3 at residues T41, S37 and S33, generates a ubiquitination degron, recruiting the E3 SCF-$\beta$-TrCP, leading to the ubiquitination and degradation of $\beta$-catenin (Clevers H and Nusse R Cell 2012, 149: 1192-1205). The inventors have further shown that inducible ablation of CK1$\alpha$ in the mouse gut epithelium triggers a massive epithelial Wnt response, which surprisingly did not alter intestinal homeostasis, with only little enhanced proliferation and no tumorigenesis (Elyada et al. Nature 2011, 470: 409-413). This is dissimilar to the consequences of acute ablation of other components of the $\beta$-catenin destruction complex, such as APC, which results in loss of homeostasis and tumorigenesis (O. J. Sansom, O. J. et al. Genes Dev. 2004, 18:1385-1390).

The inventors of the present application have found that the reason for homeostasis maintenance following CK1$\alpha$ ablation is that parallel to Wnt activation, CK1$\alpha$ ablation induces several tumor-suppressor pathways, among which are DNA damage response (DDR), cellular senescence and p53 pathway activation (Elyada E et al. Nature 2011, 470: 409-413, Pribluda A et al. Cancer Cell 2013, 24: 1-5).

Whereas the molecular mechanisms underlying the activation of these anti-neoplastic pathways are still elusive, the inventors have found that that CK1$\alpha$ ablation induces disproportionally minor DNA damage, with no signs of ATM activation, indicating that CK1$\alpha$-induced DDR and p53 activation likely entail uncommon molecular mechanisms (Burstain I et al, unpublished). In addition, the inventors have found that CK1$\alpha$ ablation results in the induction of a new type of an inflammatory response, denoted parainflammation, which is confined to the epithelium, with no common signs of inflammatory response (inflammatory cell infiltration, calor, rubor, tumor and dolor) (Pribluda A et al. Cancer Cell 2013, 24: 1-5, Lasry A and Ben-Neriah Y 2015, Trends in Immunology, Vol. 36: 217-228). Parainflammation cooperates with WT p53 activation in suppressing tumorigenesis, yet switches to a tumor promoting mechanism in the absence of functional p53 Pribluda A et al. Cancer Cell 2013, 24: 1-5, Aran et al., Genome Biol. 2016 Jul. 8; 17(1):145).

Whereas it is already established that CK1$\alpha$ is a major regulator of p53, the inventors have also found that the combined ablation of CK1$\delta$ and CK1$\epsilon$ in the gut epithelium also results in p53 activation, which may synergize with CK1$\alpha$-induced p53 activation.

IRAK1 was identified as a therapeutic target for MDS, and certain subsets of AML and triple negative breast cancer (Garrett W. Rhyasen et al, 2013, Cancer Cell 24, 90-104, Rhyasen G W, Bolanos L, Starczynowski D T, 2013, Exp Hematol. 41:1005-7, Zhen Ning Wee et al, 2015, NATURE COMMUNICATIONS, 6:8746). IRAK1 mRNA is over-expressed in ~20-30% of MDS patients and the IRAK1 protein is dramatically over-expressed and is hyperactivated in a majority of MDS marrow sample examined. IRAK1 is a serine/threonine kinase that mediates signals elicited from Toll-like receptor (TLR) and Interleukin-1 Receptor (IL1R). Following receptor activation, IRAK1 becomes phosphorylated which then leads to recruitment of TRAF6, resulting in TRAF6 activation of NF-$\kappa$B and JNK pathways. The molecular source of IRAK1 overexpression and/or hyper-activation in MDS (or AML) is not conclusive. It is thought that over-expression of TLR or necessary cofactors in MDS clones may result in chronic IRAK1 activation even in the absence of infection. Small molecule inhibitors targeting IRAK1 (IRAK1/4 Inhibitor, Amgen Inc.) have been originally developed for autoimmune and inflammatory diseases. Given that IRAK1 is hyperactivated (i.e., phosphorylated) in MDS but not normal marrow cells, Starczynowski and colleagues showed that IRAK-Inhibitor treatment (IRAK1/4, Amgen) and the knockdown of IRAK1 resulted in dramatic impairment of MDS cell proliferation, progenitor function, and viability in vitro and in vivo. Yu and colleagues showed that IRAK1 overexpression confers triple negative breast cancer cells (TNBC) growth advantage through NF-$\kappa$B-related cytokine secretion and metastatic TNBC cells exhibit gain of IRAK1 dependency, resulting in high susceptibility to genetic and pharmacologic inhibition of IRAK1. Paclitaxel treatment of TNBC cells induces strong IRAK1 phosphorylation, an increase in inflammatory cytokine expression, enrichment of cancer stem cells and acquired resistance to paclitaxel treatment. Pharmacologic inhibition of IRAK1 was able to reverse paclitaxel resistance by triggering massive apoptosis. IRAK1 was also found to be a DEK transcriptional target and is essential for head and neck cancer cell survival (Adams A K et al. Oncotarget. 2015, 22; 6(41): 43395-43407) and also as potential target in the treatment of inflammatory- and immune-related disorders (Bahia M S et al. Cell Signal. 2015 June; 27(6):1039-55).

The inventors have thus found that compounds of the invention are able to inhibit IRAK1, an important upstream regulator of the NF-kB pathway which plays an important role in hematological malignancies.

GENERAL DESCRIPTION

The present invention provides a compound having the general formula (I), including any stereoisomer or salt thereof:

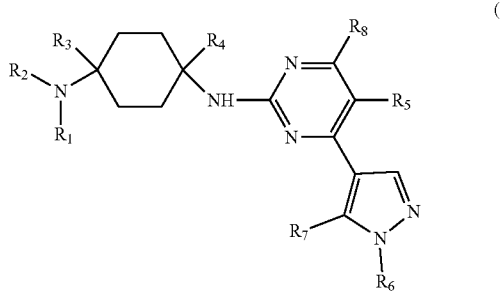

(I)

wherein $R_1$ and $R_2$ are each independently selected from H, straight or branched $C_1$-$C_8$ alkyl, straight or branched $C_1$-$C_5$ alkoxy, straight or branched $C_1$-$C_5$ acyl, $C_5$-$C_{15}$ aryl, $C_3$-$C_7$ heteroaryl each optionally substituted by at least one of halide, hydroxyl, ester, ether, $C_5$-$C_{15}$ aryl, $C_3$-$C_7$ heteroaryl, and amide; or $R_1$ and $R_2$ together with the nitrogen atom they are connected to form a 4-7 membered saturated, unsaturated or aromatic ring that may optionally include at least one of N, O, NH, C=N, C=O or $SO_2$ and can optionally be substituted with at least one of straight or branched $C_1$-$C_5$ alkyl, $C_5$-$C_{15}$ aryl, $C_3$-$C_7$ heteroaryl, hydroxyl, halide and cyano;

$R_3$ and $R_4$ are each independently selected from H, straight or branched $C_1$-$C_8$ alkyl optionally substituted by at least one of halide, hydroxyl, alkoxy, $C_5$-$C_{15}$ aryl, $C_3$-$C_7$ heteroaryl, ester and amide; or $R_1$ or $R_2$ together with $R_3$ and the carbon and nitrogen atom they are each connected to form a 4-7 membered saturated, unsaturated or aromatic ring that may optionally include at least one of N, NH, O, C=N, C=O, $SO_2$, and can optionally be substituted with at least one of straight or branched $C_1$-$C_5$ alkyl, $C_5$-$C_{15}$ aryl, $C_3$-$C_7$ heteroaryl, hydroxyl, carbonyl, and halide;

$R_5$ and $R_8$ are each independently selected from H, halide, straight or branched $C_1$-$C_8$ alkyl, straight or branched $C_2$-$C_8$ alkenyl, straight or branched $C_2$-$C_8$ alkynyl; optionally substituted by at least one halide;

$R_6$ is selected from straight or branched $C_1$-$C_8$ alkyl, straight or branched $C_2$-$C_8$ alkenyl, straight or branched $C_2$-$C_8$ alkynyl, $C_5$-$C_{10}$ cycloalkyl, saturated or unsaturated 4-6 membered heterocyclyle; optionally substituted by at least one of straight or branched $C_1$-$C_8$ alkyl, $C_3$-$C_7$ cycloalkyl, 4-6 membered heterocyclyle, $C_5$-$C_{15}$ aryl, $C_3$-$C_7$ heteroaryl, halide, hydroxyl, $C_1$-$C_5$ alkyl halide;

$R_7$ is selected from straight or branched $C_1$-$C_8$ alkyl, straight or branched $C_2$-$C_8$ alkenyl, straight or branched $C_2$-$C_8$ alkynyl; substituted by at least one $C_3$-$C_7$ cycloalkyl, 4-6 membered heterocyclyle, $C_5$-$C_{15}$ aryl, $C_3$-$C_7$ heteroaryl, halide, hydroxyl, $C_1$-$C_5$ alkyl halide.

The present invention provides a compound having the general formula (I), including any stereoisomer or salt thereof wherein:

$R_1$ and $R_2$ are each independently selected from H, straight or branched $C_1$-$C_8$ alkyl, straight or branched $C_2$-$C_8$ alkenyl, straight or branched $C_2$-$C_8$ alkynyl, straight or branched $C_1$-$C_5$ alkoxy, straight or branched $C_1$-$C_5$ acyl, $C_5$-$C_{15}$ aryl, $C_3$-$C_7$ heteroaryl each optionally substituted by at least one of halide, hydroxyl, ester, ether, $C_5$-$C_{15}$ aryl, $C_3$-$C_7$ heteroaryl and amide; or $R_1$ and $R_2$ together with the nitrogen atom they are connected to form a 4-7 membered saturated, unsaturated or aromatic ring that may optionally include at least one of N, O, NH, C=N, C=O or $SO_2$ and can optionally be substituted with at least one of straight or branched $C_1$-$C_5$ alkyl, straight or branched $C_2$-$C_5$ alkenyl, straight or branched $C_2$-$C_5$ alkynyl, $C_5$-$C_{15}$ aryl, $C_3$-$C_7$ heteroaryl, hydroxyl, halide and cyano;

$R_3$ and $R_4$ are each independently selected from H, straight or branched $C_1$-$C_8$ alkyl, straight or branched $C_2$-$C_8$ alkenyl, straight or branched $C_2$-$C_8$ alkynyl, optionally substituted by at least one of halide, hydroxyl, alkoxy, ester, $C_5$-$C_{15}$ aryl, $C_3$-$C_7$ heteroaryl and amide; or $R_1$ or $R_2$ together with $R_3$ and the carbon and nitrogen atom they are connected to form a 4-7 membered saturated, unsaturated or aromatic ring that may optionally include at least one of N, NH, O, C=N, C=O, $SO_2$, and can optionally be substituted with at least one of straight or branched $C_1$-$C_5$ alkyl, straight or branched $C_2$-$C_5$ alkenyl, straight or branched $C_2$-$C_5$ alkynyl, $C_5$-$C_{15}$ aryl, $C_3$-$C_7$ heteroaryl, hydroxyl, carbonyl, and halide;

$R_5$ and $R_8$ are each independently selected from H, halide, straight or branched $C_1$-$C_8$ alkyl, straight or branched $C_2$-$C_8$ alkenyl, straight or branched $C_2$-$C_8$ alkynyl, optionally substituted by at least one halide (in some embodiments $CF_3$);

$R_6$ is selected from straight or branched $C_1$-$C_8$ alkyl, straight or branched $C_2$-$C_8$ alkenyl, straight or branched $C_2$-$C_8$ alkynyl, $C_5$-$C_{10}$ cycloalkyl, saturated or unsaturated 4-6 membered heterocyclyle; optionally substituted by at least one of straight or branched $C_1$-$C_8$ alkyl, $C_3$-$C_7$ cycloalkyl, 4-6 membered heterocyclyle, $C_5$-$C_{15}$ aryl, $C_3$-$C_7$ heteroaryl, halide, hydroxyl, $C_1$-$C_5$ alkyl halid;

$R_7$ is selected from straight or branched $C_1$-$C_8$ alkyl, straight or branched $C_2$-$C_8$ alkenyl, straight or branched $C_2$-$C_8$ alkynyl; substituted by at least one $C_3$-$C_7$ cycloalkyl, 4-6 membered heterocyclyle, $C_5$-$C_{15}$ aryl, $C_3$-$C_7$ heteroaryl, halide, hydroxyl, $C_1$-$C_5$ alkyl halide.

In some embodiments, $R_1$ and $R_2$ are each independently selected from H, straight or branched $C_1$-$C_8$ alkyl optionally substituted by at least one of halide, hydroxyl, ester and amide.

In some embodiments, $R_1$ and $R_2$ are each independently selected from H, straight or branched $C_1$-$C_8$ alkoxy optionally substituted by at least one of halide, hydroxyl, ester and amide.

In some embodiments, $R_1$ and $R_2$ are each independently selected from H, $C_1$-$C_5$ acyl, optionally substituted by at least one of halide, hydroxyl, ester, ether and amide.

In other embodiments, $R_1$ and $R_2$ are each independently selected from H, $C_5$-$C_{15}$ aryl, optionally substituted by at least one of halide, hydroxyl, ester, ether and amide.

In some embodiments, at least one of $R_1$ and $R_2$ is H.

In some embodiments, $R_4$ is H. In some embodiments, $R_3$ and $R_4$ are H.

In some embodiments, $R_5$ is selected from H, Cl and straight or branched $C_1$-$C_4$ alkyl. In some embodiments, $R_5$ is H. In some embodiments, $R_8$ is selected from H, Cl and straight or branched $C_1$-$C_4$ alkyl. In some embodiments, $R_8$ is H. In some further embodiment one of $R_5$ or $R_8$ is H (i.e. only one of $R_5$ or $R_8$ is H, in other words one of $R_5$ or $R_8$ is different than H).

In some embodiments, $R_6$ is selected from straight or branched $C_1$-$C_8$ alkyl, $C_5$-$C_{10}$ cycloalkyl, saturated or unsaturated 4-6 membered heterocyclyle; and $R_7$ is selected from straight or branched $C_1$-$C_8$ alkyl, substituted by at least one $C_3$-$C_7$ cycloalkyl, 4-6 membered heterocyclyle, $C_5$-$C_{15}$ aryl, $C_3$-$C_7$ heteroaryl, halide, hydroxyl, $C_1$-$C_8$ alkyl halide.

In some embodiments, $R_6$ is selected from a straight or branched $C_1$-$C_8$ alkyl, $C_5$-$C_{10}$ cycloalkyl, 4-6 membered saturated heterocyclyle.

In some embodiments, $R_7$ is a straight or branched $C_1$-$C_8$ alkyl substituted by at least one of $C_3$-$C_7$ cycloalkyl and hydroxyl.

In some embodiments, $R_6$ is selected from straight or branched $C_1$-$C_8$ alkyl, saturated or unsaturated 4-6 membered heterocyclyle, each optionally substituted by at least one of straight or branched $C_1$-$C_8$ alkyl, $C_3$-$C_7$ cycloalkyl, halide, hydroxyl, $CF_3$.

In some embodiments, $R_7$ is a straight or branched $C_1$-$C_8$ alkyl substituted by at least one $C_3$-$C_7$ cycloalkyl.

In some embodiments, $R_1$ and $R_2$ together with the nitrogen atom they are connected to form a 4-7 membered saturated ring optionally including at least one of N or O, NH, C=N, C=O or $SO_2$ (i.e. in addition to the N atom $R_1$ and $R_2$ are connected to) and can optionally be substituted with at least one of straight or branched $C_1$-$C_5$ alkyl, hydroxyl, halide and cyano.

In some embodiments, $R_1$ and $R_2$ together with the nitrogen atom they are connected to form a 4-7 membered saturated ring.

In some embodiments, $R_1$ and $R_2$ together with the nitrogen atom they are connected to form a 4-7 membered saturated ring including at least one of N or O (in addition to the N atom $R_1$ and $R_2$ are connected to).

In further embodiments, $R_1$ and $R_2$ together with the nitrogen atom they are connected to form a 4-7 membered aromatic ring optionally including at least one of N or O (in addition to the N atom $R_1$ and $R_2$ are connected to).

In some embodiments, $R_1$ or $R_2$ together with $R_3$ and the carbon and nitrogen atom they are connected to form a 4-7 membered saturated ring that optionally includes at least one of N, NH, O, C=O, $SO_2$, and can optionally be substituted with at least one of straight or branched $C_1$-$C_5$ alkyl, hydroxyl, carbonyl, and halide.

In some embodiments, $R_1$ or $R_2$ together with $R_3$ and the carbon and nitrogen atom they are connected to form a 4-7 membered saturated ring that includes at least one of NH, O, or C=O.

In some embodiments, the compound of the invention is selected from the following:

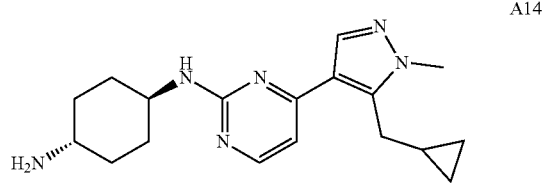 [SMILES: Cn1ncc(-c2nc(N[C@H]3CC[C@H](N)CC3)ncc2Cl)c1CC1CC1]

A14

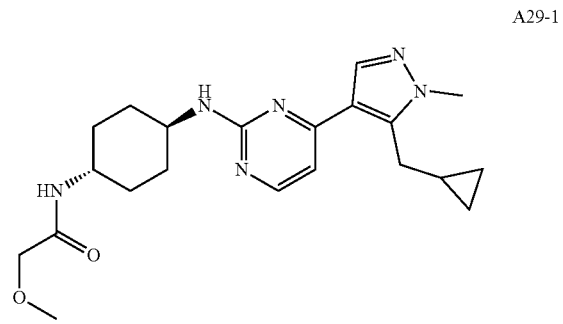

A29-1

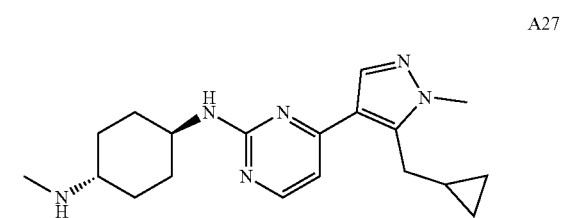

A27

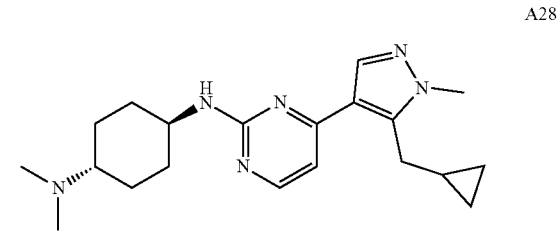

A28

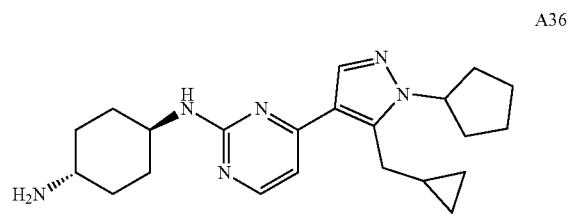

A36

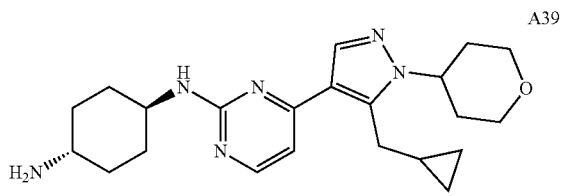

A39

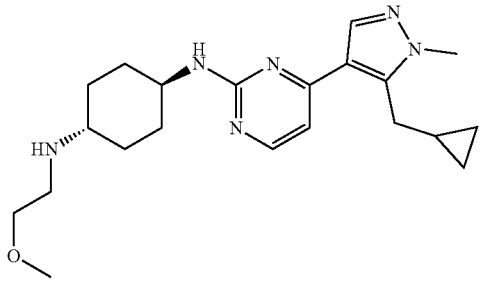 [SMILES: COCCN[C@H]1CC[C@H](Nc2nccc(-c3cnn(C)c3CC3CC3)n2)CC1]
A29
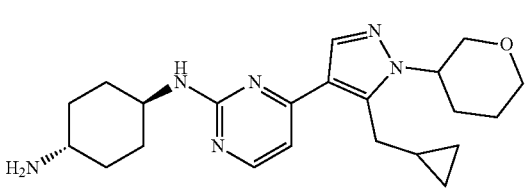
A38
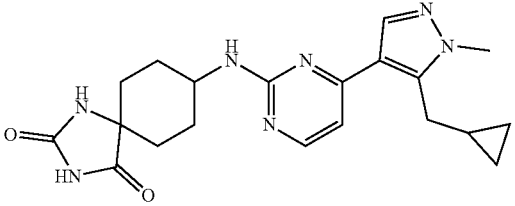 [SMILES: Cn1ncc(-c2ccnc(NC3CCC4(CC3)NC(=O)NC4=O)n2)c1CC1CC1]
A19-4
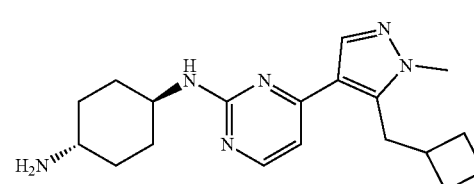
A45
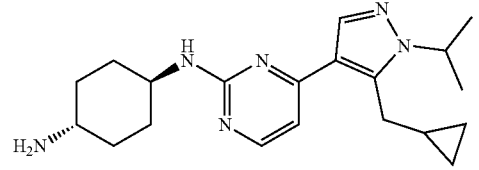
A35
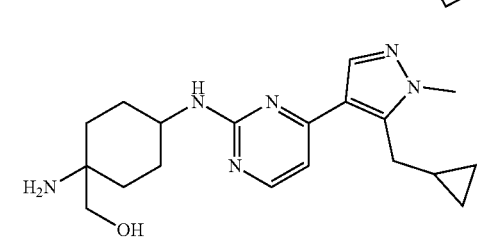
A19
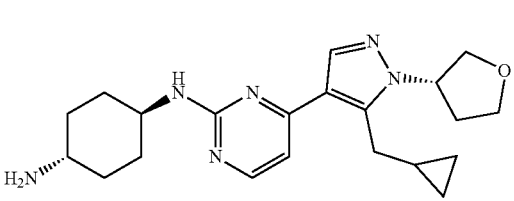
A41
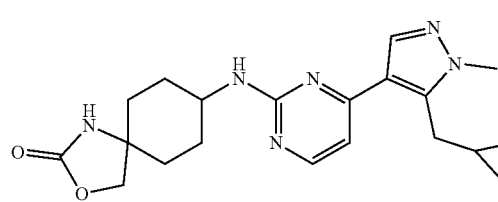
A26
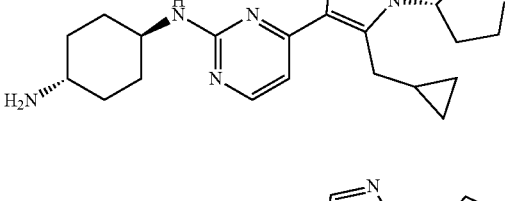
A42
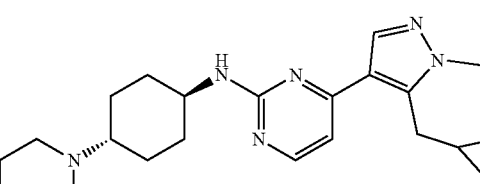
A47
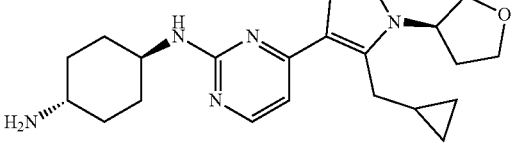
A43
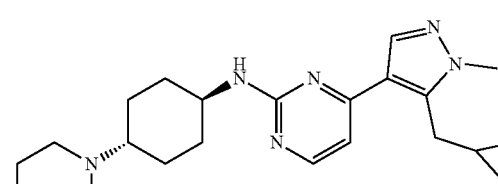
A48
A46
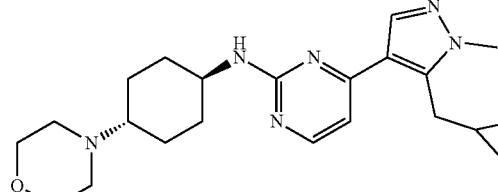
A49
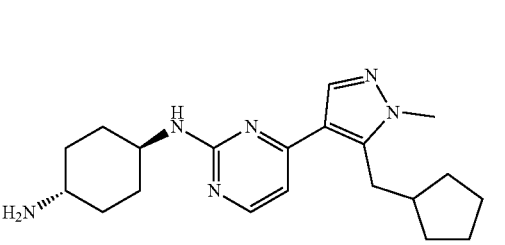

| | |
|---|---|
| 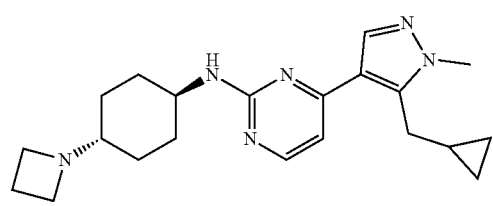 A50 | 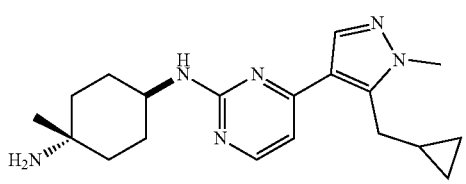 A30-1 |
| 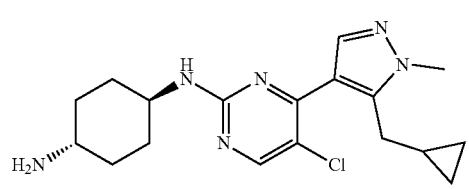 A51 | 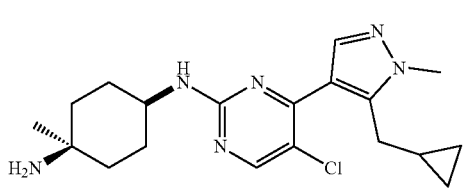 A30-2 |
| 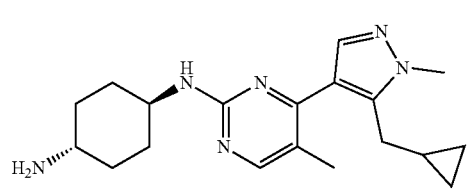 A52 | 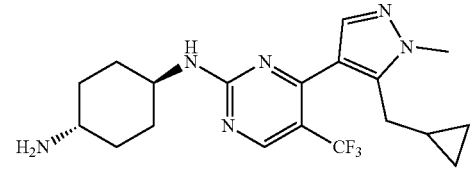 A60 |
| 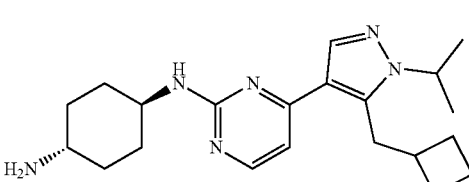 A53 | 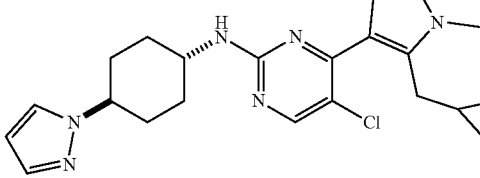 A64 |
| 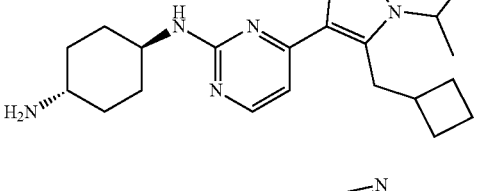 A58 | 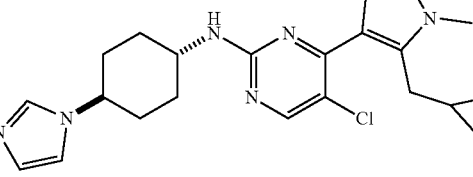 A65 |
| 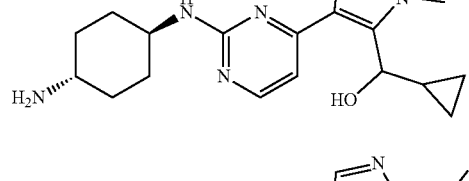 A59 | 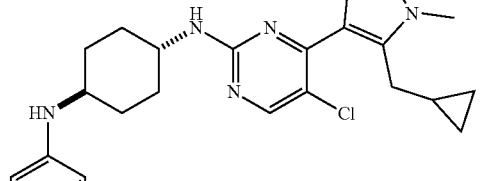 A68 |
| 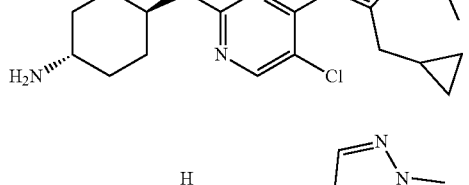 A56 | 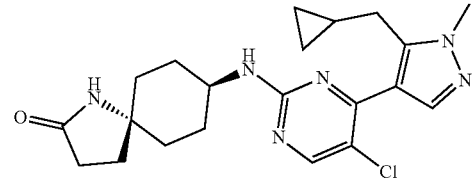 A71 |
| 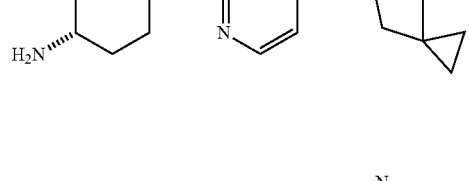 A57 | |

A74
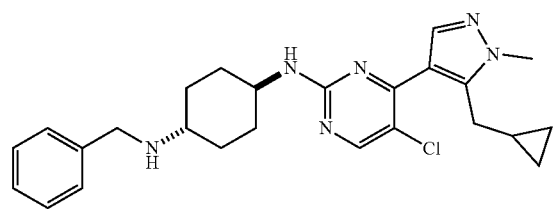
A75
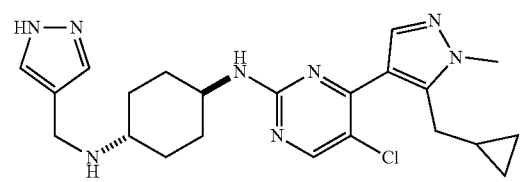
A76
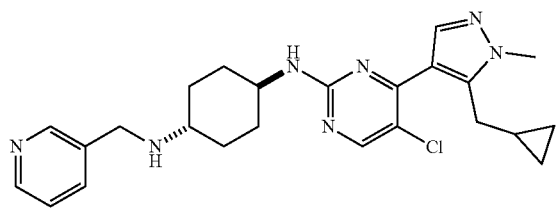
A80
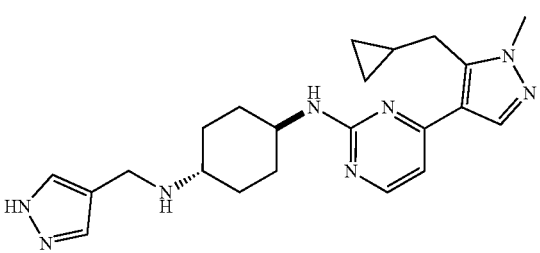
A81
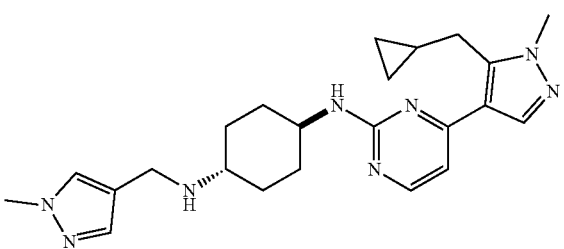
A82
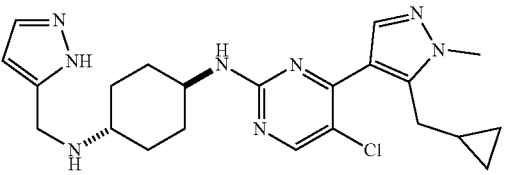
A83
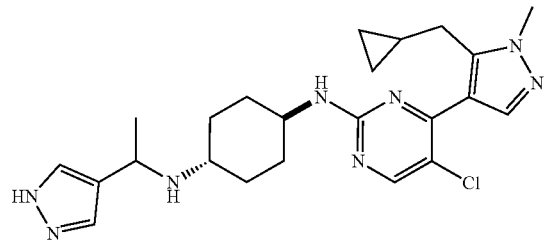
A87
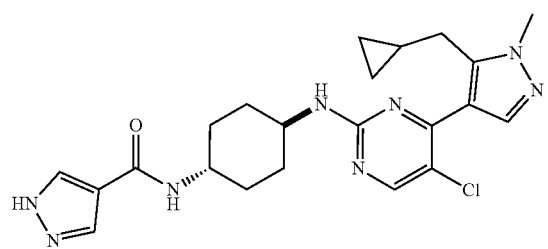
A91
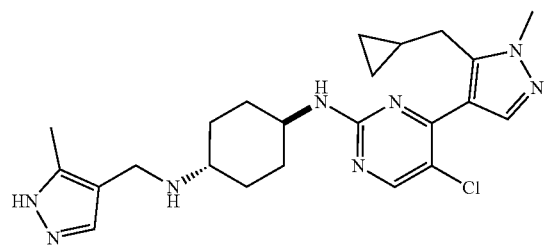
A94
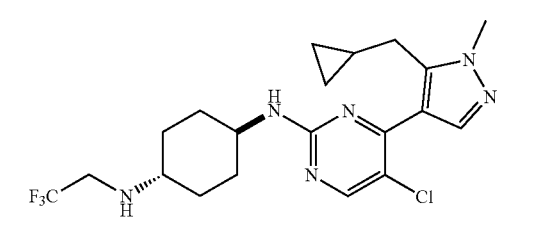
A95
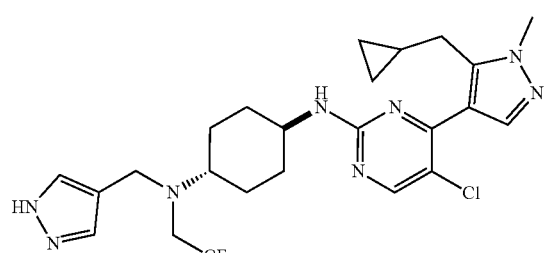
A96
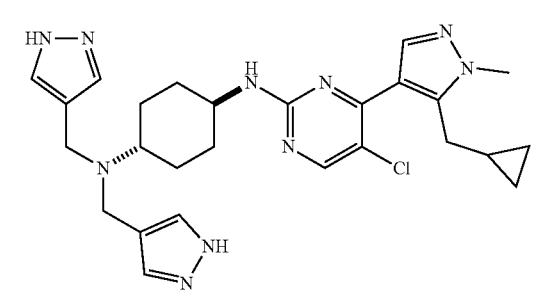

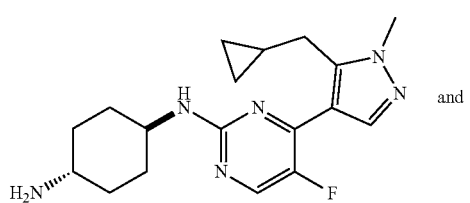

A86 and

A85

In some embodiments, the compound of the invention is:

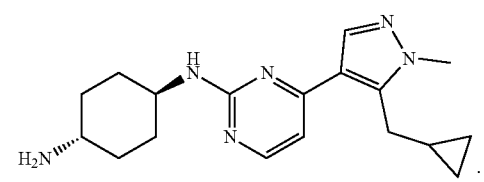

A14

In some other embodiments, the compound of the invention is:

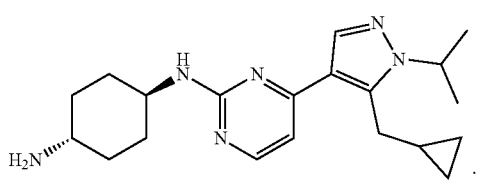

A35

In other embodiments, the compound of the invention is:

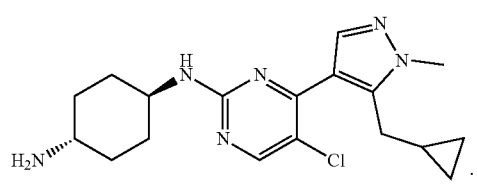

A51

The term "straight or branched $C_1$-$C_8$ alkyl" should be understood to encompass a hydrocarbon saturated chain, which can be straight or branched, comprising 1, 2, 3, 4, 5, 6, 7, or 8 carbon atoms.

The term "straight or branched $C_2$-$C_8$ alkenyl" or "straight or branched $C_2$-$C_5$ alkenyl" should be understood to encompass a hydrocarbon chain having at least one double bond between any two carbon atoms in the chain, which can be straight or branched, comprising 2, 3, 4, 5, 6, 7, or 8 carbon atoms or 2, 3, 4, 5 carbon atoms, respectively.

The term "straight or branched $C_2$-$C_8$ alkynyl" should be understood to encompass a hydrocarbon chain having at least one triple bond between any two carbon atoms in the chain, which can be straight or branched, comprising 2, 3, 4, 5, 6, 7, or 8 carbon atoms.

The term "straight or branched $C_1$-$C_5$ alkoxy" should be understood to encompass an —$OR_9$ moiety wherein $R_9$ is a straight or branched $C_1$-$C_5$ alkyl.

The term "halide" should be understood to encompass any halogen radical selected from —F, —Br, —Cl, —I.

The term "$C_1$-$C_5$ alkyl halide" should be understood to encompass any straight or branched alkyl chain having between 1 to 5 carbon atoms being substituted by at least one halogen radical selected from —F, —Br, —Cl, —I, at any point one the straight or branched chain. In some embodiments alkyl halide includes one halogen; in other embodiments alkyl halide includes two halogen atoms (the same or different); in other embodiments, alkyl halide includes three halogen atoms (the same or different) and so on.

The term "hydroxyl" should be understood to encompass —OH.

The term "ester" should be understood to encompass any of —C(=O)$OR_{10}$ or —OC(=O)$R_{10}$ wherein $R_{10}$ is a straight or branched $C_1$-$C_8$ alkyl.

The term "amide" should be understood to encompass any of —C(=O)$NR_{11}R_{12'}$, —$NR_{11}$C(=O)$R_{12'}$ wherein $R_{11}$ and $R_{12'}$ are each independently H or a straight or branched $C_1$-$C_8$ alkyl.

The term "ether" should be understood to encompass any of —$R_{13}OR_{14'}$ or —$OR_{15'}$ wherein $R_{13}$ is selected from a straight or branched $C_1$-$C_8$ alkylene and $R_{14'}$ and $R_{15'}$ are each independently selected from a straight or branched $C_1$-$C_8$ alkyl.

The term "straight or branched $C_1$-$C_5$ acyl" should be understood to encompass any —C(=O)$R_{16}$ wherein $R_{16}$ is $C_1$-$C_5$ straight or branched alkyl.

The term "$C_5$-$C_{15}$ aryl" should be understood to encompass any single or fused aromatic ring system comprising 5 to 7 carbon atoms. Examples include, but are not limited to phenyl, pentalenyl, naphtalenyl, anthracenyl, and any combinations thereof.

The term "$C_3$-$C_7$ heteroaryl" should be understood to encompass any single or fused aromatic ring system comprising 5 to 7 carbon atoms and at least one heteroatom selected from N, O and S. Examples include, but are not limited to furanyl, benzofuranyl, isobenzofuranyl, pyrrolynyl, indolynyl, isoindolinyl, thiophenyl, banzothiophenyl, banzo[c]thiophenyl, imidazolyl, benzimidazolyl, purinyl, pyrazolyl, indazolyl, oxazolyl, benzoxazolyl, isoxazolyl, benzisoxazolyl, thiasolyl, benzothiazolyl, pyridinyl, auinolinyl, isoquinolinyl, pyromodinyl, quinzolinyl, pyridazinyl, cinnolinyl and any combinations thereof.

When referring to the embodiment wherein $R_1$ and $R_2$ together with the nitrogen atom they are connected to form a 4-7 membered saturated, unsaturated or aromatic ring should be understood to relate to any ring that may be formed having 4, 5, 6, or 7 members including said nitrogen atom. Said ring can be saturated, i.e. having all sigma bonds, unsaturated, i.e. having at least one double or at least one triple bond or any combinations thereof or aromatic, i.e. a ring system that possess aromatic character, cyclically conjugated molecular ring system with a stability (due to delocalization) significantly greater than that of a hypothetical localized structure (e.g. Kekulé structure).

For example, said ring can be selected from piperidinyl, pyrrolidinyl, azetidinyl and so forth.

In some embodiments said ring may optionally include (within the ring members) at least one of N, O, NH, C=N, C=O or $SO_2$. In some further embodiments, said ring may be optionally substituted (on the ring system by substitution of an —H atom on said ring) with at least one of straight or branched $C_1$-$C_5$ alkyl, hydroxyl, halide and cyano (—CN).

When referring to the embodiments wherein $R_1$ or $R_2$ together with $R_3$ and the carbon and nitrogen atom they are connected to form a 4-7 membered saturated, unsaturated or aromatic ring should be understood to relate to any ring that may be formed having 4, 5, 6, or 7 members including said nitrogen atom. This ring forms a spiro bi-ring system with the cyclohexyl ring in the backbone of compound of formula I. Said ring can be saturated, i.e. having all sigma bonds, or unsaturated, i.e. having at least one double or at least one triple bond or any combinations thereof. In some embodiments, the ring is an aromatic ring In some embodiments, said ring optionally includes at least one of N, NH, O, C=N, C=O, $SO_2$ within the ring formation. In some further embodiments, said ring is optionally substituted (on the ring system by substitution of an —H atom on said ring) with at least one of straight or branched $C_1$-$C_5$ alkyl, hydroxyl, carbonyl (—C(=O)R wherein R is H or $C_1$-$C_5$ straight or branched alkyl), and halide.

The term "$C_5$-$C_{10}$ cycloalkyl" or the term "$C_3$-$C_7$ cycloalkyl" should be understood to encompass a saturated (i.e. the ring containing only sigma bonds between its members) hydrocarbon ring that comprises 5, 6, 7, 8, 9, or 10 carbon atoms or 3, 4, 5, 6, or 7 carbon atoms respectively.

The term "saturated, unsaturated or aromatic 4-6 membered heterocyclyle" should be understood to encompass a saturated (i.e. the ring containing only sigma bonds between its members), unsaturated or aromatic (i.e. the ring containing at least one double bond or at least one triple bond or any combinations thereof) ring containing 4, 5, or 6 members at least one of which is a heteroatom selected from N, O, S, P.

The term "optionally substituted" as used herein means that the groups in question are either unsubstituted or substituted with one or more of the substituents specified. When the groups in question are substituted with more than one substituent the substituents may be the same or different.

Certain of the compounds described herein may contain one or more chiral center, or may otherwise be capable of existing as two enantiomers or several diastereomers. Accordingly, the compounds of this invention include also mixtures of enantiomers as well as purified enantiomers or enantiomerically enriched mixtures. The compounds of this invention include also mixtures of diastereomers, as well as purified diastereomers or diastereomerically enriched mixtures.

The invention also includes any salt of a compound of formula (I), including any pharmaceutically acceptable salt, wherein a compound of the invention has a net charge (either positive or negative) and at least one counter ion (having a counter negative or positive charge) is added thereto to form said salt. The phrase "pharmaceutically acceptable salt(s)", as used herein, means those salts of compounds of the invention that are safe and effective for pharmaceutical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 *J. PHARM. SCI.* 1-19 (1977), incorporated herein by reference.

The invention further provides a composition comprising at least one compound as defined herein above and below (according to general formula I).

The present invention also relates to pharmaceutical compositions comprising a compound of the subject invention in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association compounds of the invention or combinations thereof with any auxiliary agent. The auxiliary agent(s), also named accessory ingredient(s), include those conventional in the art, such as carriers, fillers, binders, diluents, disintegrants, lubricants, colorants, flavouring agents, antioxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered.

The invention further provides a compound as defined herein above and below (according to general formula I), for use in therapy.

The term "treatment" or "therapy" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Med.* 39:221-229 which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. In some instances, hydrogels are biodegradable or biosorbable. For purposes of this invention, hydrogels made of polyethylene glycols, collagen, or poly(glycolic-co-L-lactic acid) may be useful. See, e.g., Phillips et al. (1984) *J. Pharmaceut. Sci.,* 73: 1718-1720.

The invention further provides a compound as defined herein above and below (according to general formula I), for use in the inhibition of and least one of Casein kinase I (CKI) and Interleukin-1 receptor-associated kinase 1 (IRAK1). In some embodiments, a compound as defined herein above and below (according to general formula I), is used in the inhibition of CKI and IRAK1. Under the above embodiments, the use of a compound of the invention as defined herein above and below (according to formula I) enables the treatment of diseases, disorders, symptoms and conditions associated with at least one of CKI and IRAK1 (or in some embodiments, both CKI and IRAK1). Under such aspects the invention provides treatment of diseases, disorders, symptoms and conditions associated with the inhibition of at least one of CKI and IRAK1 (or in some embodiments, both CKI and IRAK1).

In another one of its aspects the invention provides a compound as defined herein above and below (according to general formula I), for use in the inhibition of Interleukin-1 receptor-associated kinase 1 (IRAK1).

The invention further provides a compound as defined herein above and below (according to general formula I), for use in the inhibition of Casein kinase I (CKI).

The term "Casein kinase I" should be understood to encompass a protein kinases family that are serine/threonine-selective enzymes that function as regulators of signal transduction pathways in most eukaryotic cell types. CK1 isoforms are involved in Wnt signaling, circadian rhythms, nucleo-cytoplasmic shuttling of transcription factors, DNA repair, p53 activation and DNA transcription.

The term "Interleukin-1 receptor-associated kinase 1" should be understood to encompass an enzyme encoded by the IRAK1 gene which was found to be an important upstream regulator of the NF-kB pathway involved in disease pathways of hematological malignancies, such as multiple myeloma, MDS, leukemia and lymphoma, breast cancer, head and neck cancer, inflammatory and immune related disorders and others.

When referring to the "inhibition" of said enzyme, it should be understood to encompass any qualitative or quantitative decrease in the activity of said enzyme due to direct or indirect binding of at least one compound of the invention to said enzyme.

The invention further provides a compound as defined herein above and below (according to general formula I), for use in the treatment of a condition, symptom or disease associated with a malignant condition.

In some embodiments, said malignant condition is cancer. In other embodiments, said cancer has either WT, or mutant p53 (mutations that deactivate p53 typical of cancer conditions). In further embodiments, said cancer is selected from leukemia, malignant melanoma, breast cancer, prostate cancer and colorectal cancer. In some embodiments, said cancer has WT p53.

The invention further provides a compound as defined herein above and below, for use in the treatment of cancer having WT p53, wherein said WT p53 is a biomarker for the said compound efficacy. Thus, under this aspect WT p53 serves as a measurable indicator to the efficacy of cancer treatment of the compound or composition comprising a compound of the invention. The invention further provides a method of treating cancer having WT p53 in a subject in need thereof, wherein said WT p53 is a biomarker for the said compound efficacy In some embodiments, said use further comprises an induction of cancer immunotherapy response. Thus, in some embodiments of the invention a compound or a composition comprising a compound of the invention provides both treatment of cancer (anti-tumor, anti-malignant activity) and cancer immunotherapy response.

In some embodiments, said malignant condition is selected from hematological malignancies (Multiple Myeloma, Myelodysplastic Syndrome (MDS), Acute Myeloid Leukemia (AML), Melanoma and ER-negative breast cancer, Diffuse Large B cell lymphoma (DLBCL), Chronic Myelogenous Leukemia (CML), Chronic lymphocytic leukemia (CLL), head and neck cancer, and any combinations thereof.

In another one of its aspects the invention provides a compound as defined herein above and below for use in inducing anti-tumor response. In some embodiments, said anti-tumor response comprises cancer immunotherapy response.

The term "induced anti-tumor response" should be understood to encompass any qualitative or quantitative chemotherapy of cancerous tumors.

The term "cancer immunotherapy response" should be understood to encompass any qualitative or quantitative cancer immunotherapy induction of the subject's own immune system to fight the cancerous cells. Typically, immunotherapies can be categorized as active, passive or hybrid (active and passive), and are designed to exploit the fact that cancer cells often have molecules on their surface that can be detected by the immune system of a subject, known as tumour-associated antigens (TAAs); they are often proteins or other macromolecules (e.g. carbohydrates). Active immunotherapy directs the immune system to attack tumor cells by targeting TAAs. Passive immunotherapies enhance existing anti-tumor responses.

In some embodiments, said cancer immunotherapy response relates to the change in the expression of an immune checkpoint molecules on tumor cell, on an antigen presenting cell, on a T cell or on a Natural Killer (NK) cell.

In some embodiments, said cancer immunotherapy response relates to the reduction in the expression of an immune checkpoint molecule on tumor cell that induces suppression of the anti-tumor activity of a T cell.

In some embodiments, said cancer immunotherapy response relates to the reduction in the expression of the checkpoint protein PD-L1. In some other embodiments, said immunotherapy response relates to the inhibition of PD-L1. In some further aspects, a compound of the invention is used in a method of inhibiting PD-L1.

The invention further provides a compound as defined herein above and below (according to general formula I), for use in the treatment of an inflammatory and immune related disorder including a condition, symptom or disease associated therewith.

When referring to "inflammatory and immune related disorders" it should be understood to relate to any type of disorder (including conditions, symptoms and diseases associated therewith) that are treatable with Interleukin-1 receptor associated kinase inhibitors. It has been shown for example that IRAK1 is an indispensable element of IL-Rs and TLR pathways that can regulate the abnormal levels of cytokines, and therefore can be employed to manage immune- and inflammation-related disorders such as for example rheumatoid arthritis, inflammatory bowel disease, psoriasis, gout, asthma and cancer (Bahia M S et al. *Cell Signal*. 2015 June; 27(6):1039-55).

The invention further provides a method of treating a condition, symptom or disease associated with a malignant condition in a subject in need thereof, said method comprising the step of administering to said subject at least one compound as defined herein above and below (according to general formula I).

The invention further provides a method of inhibiting at least one of Casein kinase I (CKI) and Interleukin-1 receptor-associated kinase 1 (IRAK1) in a subject in need thereof comprising the step of administrating to said subject at least one compound as defined herein above and below (according to general formula I).

In another one of its aspects the invention provides a method of inhibiting Interleukin-1 receptor-associated kinase 1 (IRAK1) in a subject in need thereof comprising the step of administrating to said subject at least one compound as defined herein above and below (according to general formula I).

In some embodiments a method of the invention further comprising inducing cancer immunotherapy response in said subject.

In another one of its aspects the invention provides a method for inducing an cancer immunotherapy response in a subject in need thereof, said method comprising the step of administering to said subject at least one compound as disclosed herein above and below.

The invention further provides a method of treating an inflammatory and immune related disorder including a condition, symptom or disease associated therewith; said method comprises administering to a subject in need thereof a compound as defined herein above and below (according to general formula I).

The invention also provides a method of inhibiting Casein kinase I in a subject in need thereof comprising the step of administrating to said subject at least one compound as defined herein above and below (according to general formula I).

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1B compounds A30-1, A30-2, A51, A60, A64, A65)—screen in RKO colorectal cell line. RKO cells were incubated for 16 hours at 37° C. with indicated concentrations of the compounds and analyzed by Western Blot. Shown are β-catenin and p53 stabilization and phosphorylation of H2AX (γH2AX), a marker of DNA damage, indicative of CKIα kinase inhibition. Note that whereas β-catenin and p53 stabilization, and H2AX phosphorylation is a common effect of most compounds, some compounds do not stabilize β-catenin, whereas close analogues (e.g., A19-4), only stabilize β-catenin. CKIα protein levels serves as a loading control.

FIG. 2A is a schematic representation of the experimental procedure; Incubation with A14 or DMSO for 8 hours. FIG. 2B shows a dramatic reduction of the leukemic cell number following A14 treatment—a dose response curve. FIG. 2C shows the increased percentage of apoptotic cells (Annexin5+/7AAD−) in a dose dependent manner. FIG. 2D shows the increased percentage of total death (7AAD+) cells in a dose dependent manner.

FIG. 3A is a schematic representation of the experimental procedure, inoculating BM cells from a CML blast crisis mouse (GFP+ cells) to normal C57Bl/6 mice and daily treatment (oral administration) with A14 or vehicle alone. FIG. 3B shows the percentage of GFP+ leukemia cells in peripheral blood at day 9 following treatment; A14 (N=6) compared to the vehicle treated mice (N=6). FIG. 3C shows the percentage of GFP+ leukemia cells in the bone marrow at day 9 following treatment: A14 (N=6) compared to the vehicle treated mice (N=6).

FIGS. 4A-4F show the complete blood count at day 9 following A14 treatment of CML blast crisis mice: FIG. 4A shows the absolute number of White blood cells (WBC) in peripheral blood ($10^9$/L) (N=5). FIG. 4B shows the absolute number of Lymphocytes (Lymph) in peripheral blood ($10^9$/L) (N=5). FIG. 4C shows the absolute number of Monocytes (Mono) in peripheral blood ($10^9$/L) (N=5). FIG. 4D shows the absolute number of Granulocytes (Gran) in peripheral blood ($10^9$/L). FIG. 4E shows the red blood counts (RBC, $10^{12}$/L). FIG. 4F shows the hemoglobin level (HGB, g/L).

FIGS. 7A-7D show the inhibitory effect of A14 on the progression of AML. FIG. 7A is a schematic representation of the experimental procedures. FIG. 7B demonstrates the percentage of GFP+ leukocytes in peripheral blood (PB) of A14 treated compared to vehicle treated mice. FIGS. 7C and 7D shows representative Flow Cytometry analysis plots of the GFP+ leukocytes in PB one day before (FIG. 7C) and three days (FIG. 7D) following A14 treatment.

FIG. 8A shows the absolute number of white blood cells (WBC) in peripheral blood ($10^9$/L). FIG. 8B shows the absolute number of lymphocytes (Lymph) in peripheral blood ($10^9$/L). FIG. 8C shows the absolute number of monocytes (Mono) in peripheral blood ($10^9$/L). FIG. 8D shows the absolute number of granulocytes (Gran) in peripheral blood ($10^9$/L). FIG. 8E shows the red blood counts (RBC, $10^{12}$/L). FIG. 8F shows the hemoglobin (g/L). FIG. 8G shows platelets (PLT) in peripheral blood ($10^9$/L).

FIGS. 11A-11E relate to the experimental results achieved from a single-dose treatment of CKI inhibitor A51 in AML mice. FIG. 11A schematically shows the preparation of AML mice and their treatment with A51 (20 mg/Kg) at day 30 from induction of the disease (Leukemia inoculation). FIGS. 11B-11E show the effect of A51 after 16 hrs from treatment (in comparison with treatment with vehicle alone) in reduction of the total leukemia cells in the blood: FIG. 11B shows the reduction in WBC in the peripheral blood (PB), FIG. 11C shows the shrinking of the leukemic spleen and FIGS. 11D and 11E show the reduction of proportion of leukemic blasts (GFP+ cells) in the peripheral blood (PB) and bone marrow (BM), respectively.

DETAILED DESCRIPTION OF EMBODIMENTS

Figure 1A:
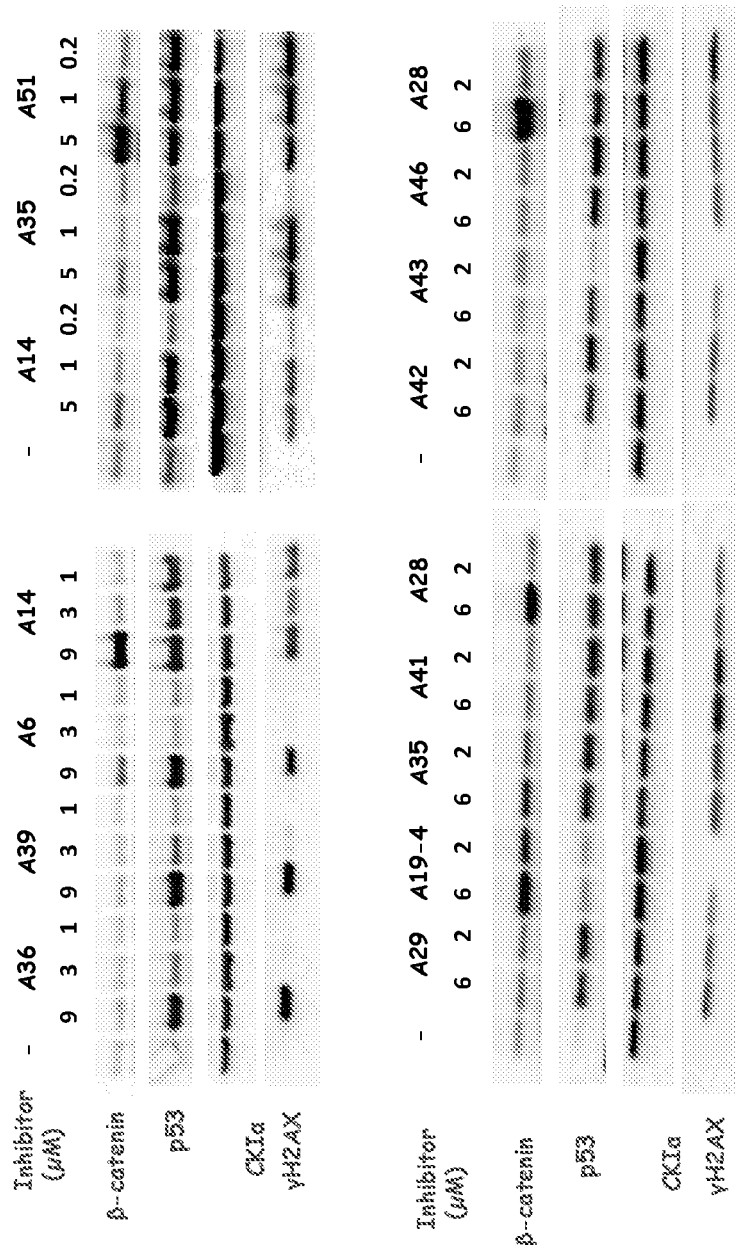
FIGS. 1A and 1B show a dose response of the indicated compounds of the invention (FIG. 1A compounds A36, A39, A6, A14, A35, A51, A29, A19-4, A41, A28, A42, A43, A46.

Preparation of (E)-1-cyclopropyl-4-(dimethyl-amino)-3-(2-(methylthio)pyrimidin-4-yl)but-3-en-2-one (Core A) and 4-(5-(cyclopropylmethyl)-1H-pyrazol-4-yl)-2-(methylthio)pyrimidine (Core B)

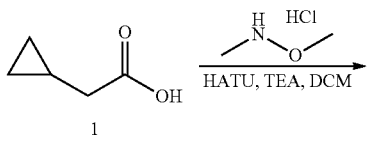

1

Step 1:

N, O-Dimethylhydroxylamine hydrochloride (25.14 g, 257.69 mmol, 1.72 eq), HATU (56.97 g, 149.82 mmol, 1.00 eq) and TEA (45.48 g, 449.46 mmol, 3.00 eq) were added to a solution of 2-cyclopropylacetic acid (15.00 g, 149.82 mmol, 1.00 eq) in DCM (500 mL) at 0° C., and then the mixture was stirred at 30° C. for 3 h. The resulting mixture was poured into water (500 mL). The aqueous washing phase was extracted with DCM (3*250 mL). The combined organic layers were dried over anhydrous $Na_2SO_4$, filtered and concentrated. The residue was purified by column chromatography ($SiO_2$, petroleum ether (PE):ethyl acetate (EA)=50:1 to 10:1) to give the desired compound 2 (13.20 g, 82.97 mmol, 55.4% yield) as colorless liquid.

$^1$H NMR ($CDCl_3$, 400 MHz) δ 3.65 (s, 3H), 3.17 (s, 3H), 2.33 (d, J=6.8 Hz, 2H), 1.09-1.06 (m, 1H), 0.54-0.50 (m, 2H), 0.16-0.14 (m, 2H).

Step 2:

To a solution of 4-methyl-2-methylsulfanyl-pyrimidine (9.00 g, 64.19 mmol, 1.00 eq) in THF (500 mL) was added LDA (2 M, 48.46 mL, 1.51 eq) at −78° C. After stirring for 1 h, a solution of compound 2 (13.79 g, 96.29 mmol, 1.50 eq) in THF (500 mL) was added drop wise at −78° C. and then the reaction mixture was stirred at −78° C. for 4 h. Quenched with saturated aq. $NH_4Cl$ (100 mL), the aqueous phase was extracted with ethyl acetate (3×50 mL). The combined organic layers were washed with brine, dried over anhydrous $Na_2SO_4$, filtered and concentrated. The residue was crystallized from petroleum ether/ethyl acetate to afford the desired compound 4 (13.60 g, 55.06 mmol, 85.8% yield) as a yellow solid.

LCMS: RT=0.629 min, m/z 223.0 $[M+H]^+$.

Step 3:

A solution of compound 4 (13.60 g, 61.18 mmol, 1.00 eq) in DMF-DMA (51.42 g, 2.45 mol, 40 eq) was stirred at 90° C. for 2 h. The solvent was removed in vacuum. The residue was purified by column chromatography on silica gel to give Core A (10.60 g, 36.30 mmol, 59.3% yield) as a yellow solid.

LCMS: RT=0.634 min, m/z 278.2 $[M+H]^+$ $^1$H NMR ($CDCl_3$, 400 MHz) δ 8.38 (d, J=6.8 Hz, 1H), 7.62 (s, 1H), 6.96 (s, 1H), 2.96-2.87 (m, 6H), 2.56 (s, 3H), 2.38 (d, J=8.8 Hz, 2H), 1.04-1.02 (m, 1H), 0.52-0.46 (m, 2H), 0.09-0.04 (m, 2H).

Step 4:

A solution of Core A (10.60 g, 38.21 mmol, 1.00 eq) and hydrazine hydrate (6.75 g, 114.63 mmol, 3.00 eq) in ethanol (200 mL) was stirred at 90° C. for 3 h. The solvent was removed in vacuum. The residue was purified by column chromatography on silca gel to afford Core B (9.00 g, 35.81 mmol, 93.7% yield) as a light yellow solid.

LCMS: RT=2.018 min, m/z 247.1 $[M+H]^+$ $^1$H NMR ($CDCl_3$, 400 MHz) δ 8.43 (d, J=5.2 Hz, 1H), 8.04 (s, 1H), 7.10 (d, J=5.2 Hz, 1H), 3.12 (d, J=7.2 Hz, 2H), 2.60 (s, 3H), 1.19-1.14 (m, 1H), 0.66 (q, J=5.2 Hz, 2H), 0.32 (q, J=5.2 Hz, 2H).

Preparation of 4-(5-(cyclopropylmethyl)-1-methyl-1H-pyrazol-4-yl)-2-(methylsulfonyl)pyrimidine (Core C)

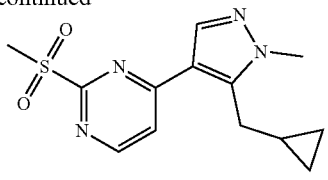

Core C

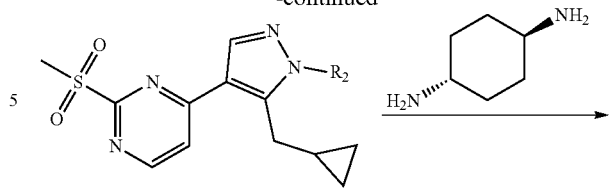

n_7

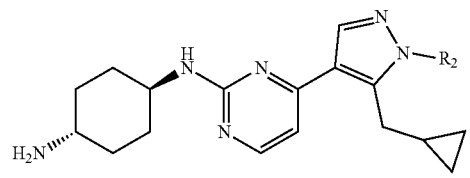

A-n

Step 1:

A solution of Core A (6.20 g, 22.35 mmol, 1.00 eq) and methylhydrazine (8.00 g, 69.46 mmol, 3.11 eq) in ethanol (100 mL) was stirred at 90° C. for 16 hrs. The solvent was removed in vacuum. The residue was purified by pre-HPLC (basic condition) to afford compound 5 (1.80 g, 6.84 mmol, 30.6% yield) as a yellow solid and the isomer 5A (2.00 g, 7.30 mmol, 32.6% yield) as a yellow oil.

Compound 5:

LCMS: RT=2.551 min, m/z 261.1 [M+H]$^+$ $^1$H NMR (CDCl$_3$, 400 MHz) δ 8.38 (d, J=5.2 Hz, 1H), 7.90 (s, 1H), 7.11 (d, J=5.2 Hz, 1H), 3.93 (s, 3H), 3.24 (d, J=6.4 Hz, 2H), 2.62 (s, 3H), 1.12-1.09 (m, 1H), 0.54-0.49 (m, 2H), 0.32-0.28 (m, 2H).

Regioisomer 5A:

LCMS: RT=2.486 min, m/z 261.1 [M+H]$^+$ $^1$H NMR (CDCl$_3$, 400 MHz) δ 8.41 (d, J=5.2 Hz, 1H), 7.90 (s, 1H), 7.04 (d, J=5.2 Hz, 1H), 3.92 (s, 3H), 2.96 (d, J=6.4 Hz, 2H), 2.61 (s, 3H), 1.20-1.17 (m, 1H), 0.50-0.45 (m, 2H), 0.26-0.22 (m, 2H).

Step 2:

To a solution of compound 1 (1.50 g, 5.76 mmol, 1.00 eq) in DCM (20 mL) was added m-CPBA (2.98 g, 17.28 mmol, 3.00 eq) at 0° C. and stirred at 30° C. for 2 hrs. The resulting mixture was washed with NaHSO$_3$ (2×100 mL), saturate aq. NaHCO$_3$ (100 mL) and brine, dried over anhydrous Na$_2$SO$_4$, filtered and concentrated. The residue was purified by column chromatography on silica gel (petroleum ether:ethyl acetate=10:1 to 1:1) to give the compound Core C (1.50 g, 5.08 mmol, 88.2% yield) as a yellow solid.

LCMS: RT=1.891 min, m/z 293.0 [M+H]$^+$ $^1$H NMR (CDCl$_3$, 400 MHz) δ 8.74 (d, J=5.6 Hz, 1H), 7.97 (s, 1H), 7.58 (d, J=5.6 Hz, 1H), 3.94 (s, 3H), 3.37 (s, 3H), 3.25 (d, J=6.8 Hz, 2H), 1.14-1.11 (m, 1H), 0.52-0.49 (m, 2H), 0.37-0.35 (m, 2H).

General procedures for the preparation of A-n:

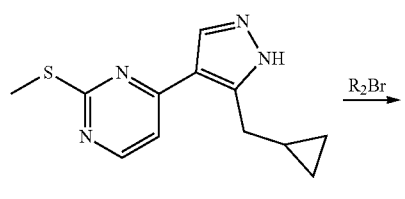

Core B

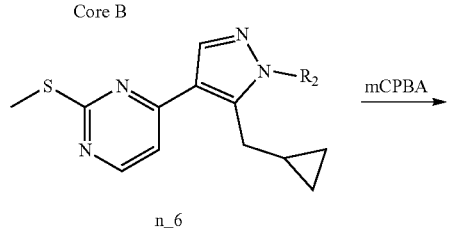

n_6

Method A: Preparation of Compound n_6

A solution of Core B (25 mmol, 1.00 eq) in DMF (50 mL) was cooled to 0° C., and NaH (1.50 eq) was added. After stirred at 0° C. for 1 h, RBr (1.60 eq) was added and the reaction mixture was stirred at 20° C. for 15 hrs. Water (10.00 mL) was added and extracted with ethyl acetate (3*10 mL). The combined organic layers were washed with water (10 mL) and brine (10 mL), dried over Na$_2$SO$_4$, filtered and concentrated to give the crude product, which was purified to give compound n_6.

Method B: Preparation of Compound n_7

To a solution of compound n_6 (10 mmol, 1.00 eq) in dichloromethane (30 mL) was added m-CPBA (3.00 eq) at 0° C. and the reaction mixture was stirred at 20-30° C. for 5 h. The resulting mixture was washed with NaHSO$_3$ (2×50.00 mL), saturate aq. NaHCO$_3$ (50 mL) and brine (10 mL), dried over anhydrous Na$_2$SO$_4$, filtered and concentrated to give compound n_7.

Method C: Preparation of Compound A-n

A mixture of compound n_7 (10 mmol, 1.0 eq), DIEA (10.00 eq) and trans-4-amino-cyclohexanol (1.0-3.0 eq) in DMSO (80 mL) was heated at 160° C. for 3 hrs. The reaction mixture was cooled to ambient temperature and poured into water (100 mL) and then extracted with dichloromethane (3×50 ml). The combined layers were washed with brine, dried over anhydrous Na$_2$SO$_4$, filtered and concentrated. The residue was purified by pre-HPLC (basic condition) to afford compound A-n.

Method D: Preparation of Compound A-n

The solution of compound n_7 (10 mmol, 1.00 eq) and trans-cyclohexane-1,4-diamine (2.0-4.0 eq) in dioxane (40 mL) was stirred at 130° C. for 2 h with microwave. The mixture was filtered and the filtrate was purified by pre-HPLC (basic condition) to give A-n.

Preparation of (1r, 4r)-N$^1$-(4-(5-(cyclopropylmethyl)-1-isopropyl-1H-pyrazol-4-yl)pyrimidin-2-yl)cyclohexane-1,4-diamine (A-35)

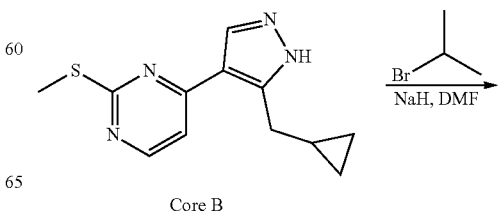

Core B

28

Preparation of (1R, 4R)—N$^1$-(4-(1-cyclopentyl-5-(cyclopropylmethyl)-1H-pyrazol-4-yl)pyrimidin-2-yl)cyclohexane-1,4-diamine (A-36)

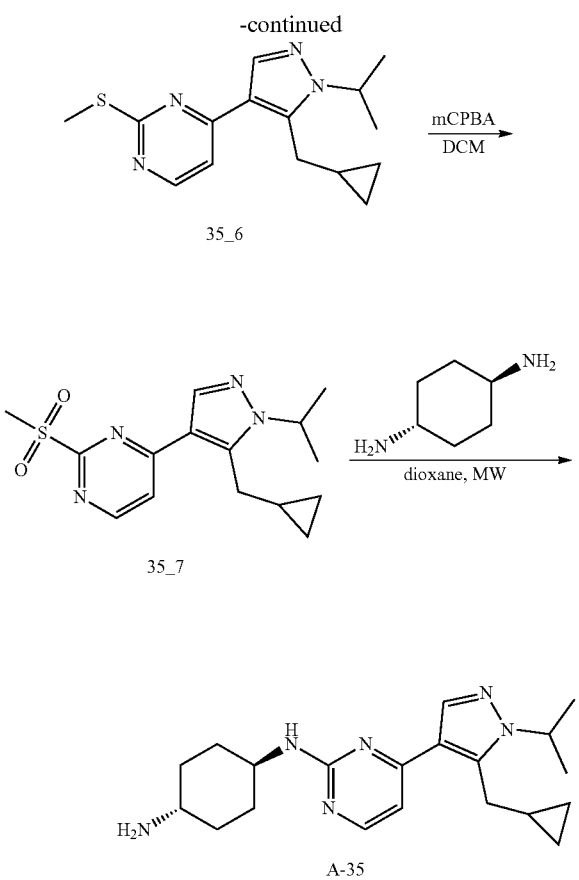

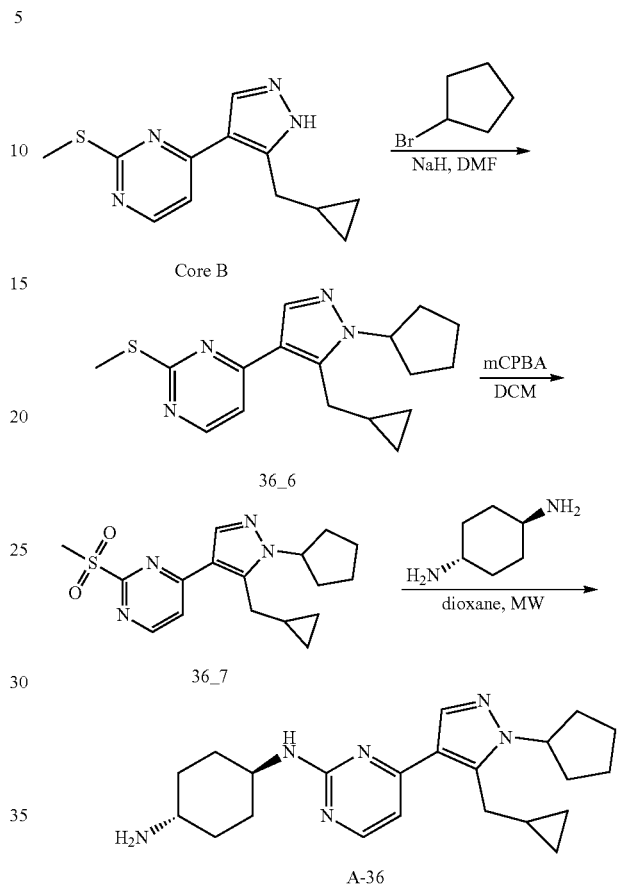

Step 1:

Compound 35_6 was synthesized according to the procedure described in method A and it was obtained as a yellow solid after HPLC (TFA condition) purification. Yield: 17.1%;

LCMS: RT=1.959 min, m/z 289.1 [M+H]$^+$ $^1$H NMR (CDCl$_3$, 400 MHz) δ 8.49-8.47 (d, J=2.8 Hz, 1H), 8.06 (s, 1H), 7.21-7.20 (d, J=5.6 Hz, 1H), 4.63-4.60 (t, J=6.6 Hz, 1H), 3.26-3.24 (d, J=6.4 Hz, 2H), 2.65 (s, 3H), 1.56 (s, 3H), 1.55 (s, 3H), 1.07-1.04 (m, 1H), 0.54-0.51 (m, 2H), 0.30-0.28 (m, 2H).

Step 2:

Compound 35_7 was synthesized according to the procedure described in method B and it was obtained as a yellow solid after purification through TLC. Yield: 57.8%;

LCMS: RT=0.711 min, m/z 321.1 [M+H]$^+$

Step 3:

Compound A-35 was synthesized according to the procedure described in method D with trans-cyclohexane-1,4-diamine (4.0 eq) and it was obtained as a white solid. Yield: 19.7%

LCMS: RT=1.223 min, m/z 355.3 [M+H]$^+$ $^1$H NMR (CDCl$_3$, 400 MHz) δ 8.17-8.16 (d, J=5.2 Hz, 1H), 7.89 (s, 1H), 6.72-6.71 (d, J=5.2 Hz, 1H), 4.85-4.83 (d, J=8.8 Hz, 1H), 4.60-4.53 (m, 1H), 3.23-3.22 (d, J=6.4 Hz, 2H), 2.20-2.18 (d, J=10 Hz, 2H), 2.02-1.99 (m, 2H), 1.54 (s, 3H), 1.52 (s, 3H), 1.40-1.27 (m, 4H), 1.08-1.06 (m, 1H), 0.52-0.48 (m, 2H), 0.28-0.26 (m, 2H).

Step 1:

Compound 36_6 was synthesized according to the procedure described in method A and it was obtained as a yellow oil after purification by prep_HPLC (TFA condition). Yield: 14.7%

LCMS: RT=2.228 min, m/z 315.2 [M+H]$^+$ $^1$H NMR (CDCl$_3$, 400 MHz) δ 8.31-8.30 (d, J=5.6 Hz, 1H), 7.84 (s, 1H), 7.03-7.01 (d, J=5.2 Hz, 1H), 4.67-4.63 (m, 1H), 3.20-3.18 (d, J=6.4 Hz, 2H), 2.52 (s, 3H), 2.05-2.02 (m, 7H), 1.65-1.62 (m, 2H), 0.98 (m, 1H), 0.43-0.39 (m, 2H), 0.23-0.20 (m, 2H).

Step 2:

Compound 36_7 was made according to the procedure described in method B and it was obtained as a yellow solid after purification through column chromatography. Yield: 66.6%

LCMS: RT=0.707 min, m/z 347.2 [M+H]$^+$

Step 3:

Compound A-36 was made according to the procedure described in method D with trans-cyclohexane-1, 4-diamine (2.0 eq) and it was obtained as a whit solid after purification by prep_HPLC (TFA condition). Yield: 41.35%

LCMS: RT=0.591 min, m/z 381.4 [M+H]$^+$ $^1$H NMR (CD$_3$OD, 400 MHz) δ 8.26 (s, 1H), 8.08-8.06 (d, J=6.4 Hz, 1H), 7.27-7.25 (d, J=6.8 Hz, 1H), 4.15 (s, 1H), 3.33 (s, 3H), 3.20 (s, 1H), 2.25-1.99 (m, 11H), 1.75 (m, 2H), 1.64-1.58 (m, 4H), 1.16 (m, 1H), 0.57-0.55 (m, 2H), 0.36-0.35 (m, 1H).

Preparation of (1R, 4R)—N¹-(4-(5-(cyclopropylmethyl)-1-(tetrahydro-2H-pyran-4-yl)-1H-pyrazol-4-yl)pyrimidin-2-yl)cyclohexane-1,4-diamine (A-39)

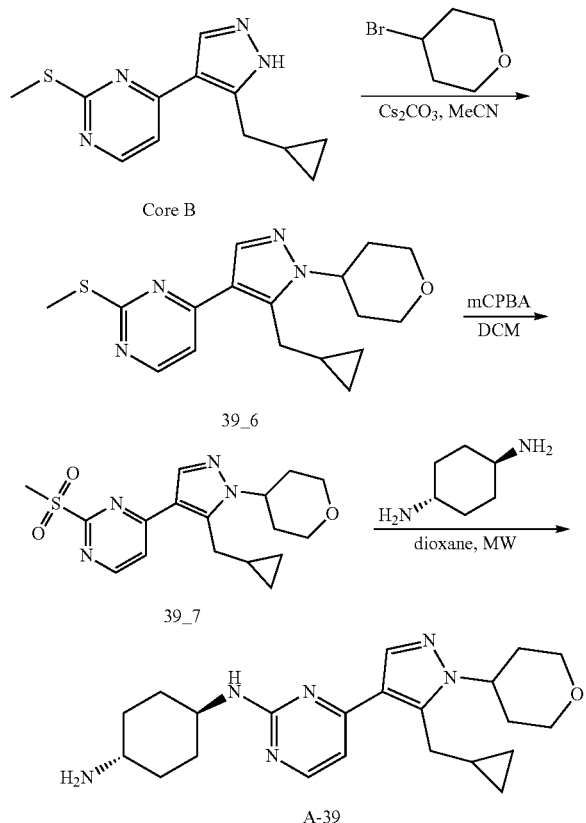

Step 1:
To a solution of Core B (700.00 mg, 2.84 mmol, 1.00 eq) in MeCN (14 mL) was added CS$_2$CO$_3$ (1.85 g, 5.68 mmol, 2.00 eq) at 0° C. After 30 min, 4-bromotetrahydropyran (703.03 mg, 4.26 mmol, 1.50 eq) was added. The mixture was stirred at 100° C. for 16 h in a sealed tube. The reaction mixture was filtered and the filtrate was concentrated. The crude product was purified by prep-HPLC (TFA) to give compound 39_6 (45.0 mg, 136.18 µmol, 4.8% yield) as a yellow solid.

LCMS: RT=0.702 min, m/z 331.1 [M+H]$^+$ $^1$H NMR (CDCl$_3$, 400 MHz) δ 8.42-8.40 (d, J=5.6 Hz, 1H), 7.94 (s, 1H), 7.11-7.10 (d, J=5.2 Hz, 1H), 4.37-4.33 (m, 1H), 4.19-4.15 (m, 1H), 3.59-3.54 (m, 2H), 3.28-3.26 (d, J=6.4 Hz, 2H), 2.6 (s, 3H), 2.44-2.40 (m, 2H), 1.87-1.84 (m, 2H), 1.05-1.02 (m, 1H), 0.55-0.50 (m, 2H), 0.33-0.30 (m, 2H).

Step 2:
Compound 39_7 was made according to the procedure described in method B and it was obtained as a yellow solid after prep TLC purification. Yield: 72.6%

LCMS: RT=0.607 min, m/z 363.1 [M+H]$^+$

Step 3:
Compound A-39 was made according to the procedure described in method C with trans-cyclohexane-1,4-diamine (3.0 eq) without DIEA and it was obtained as a yellow solid after purification through prep-HPLC (basic condition). Yield: 40.2%

LCMS: RT=1.104 min, m/z 397.4 [M+H]$^+$ $^1$H NMR (CDCl$_3$, 400 MHz) δ 8.17-8.16 (d, J=4.4 Hz, 1H), 7.89 (s, 1H), 6.72-6.70 (d, J=5.2 Hz, 1H), 5.12-5.07 (m, 1H), 4.37-4.34 (m, 1H), 4.18-4.15 (m, 2H), 3.84 (s, 1H), 3.59-3.53 (m, 2H), 3.26-3.25 (d, J=6.4 Hz, 2H), 2.77 (s, 1H), 2.44-2.40 (m, 2H), 2.16 (s, 2H), 1.93 (s, 2H), 1.87-1.83 (m, 2H), 1.32-1.27 (m, 4H), 1.05 (s, 1H), 0.54-0.49 (m, 2H), 0.29-0.27 (m, 2H).

Preparation of (1R, 4R)—N¹-(4-(5-(cyclopropylmethyl)-1-(oxetan-3-yl)-1H-pyrazol-4-yl)pyrimidin-2-yl)cyclohexane-1,4-diamine (A-43)

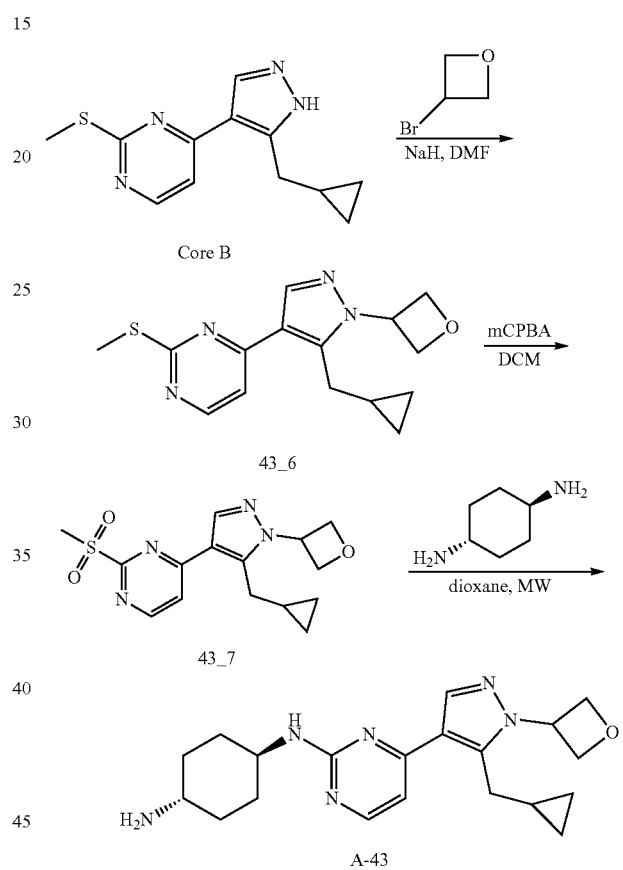

Step 1:
Compound 43_6 was synthesized according to the procedure described in method A and it was obtained as a yellow solid after purification by prep-HPLC (TFA condition). Yield: 17.9%

LCMS: RT=0.664 min, m/z 303.1 [M+H]

$^1$H NMR (CDCl$_3$, 400 MHz) δ 8.44-8.42 (d, J=5.2 Hz, 1H), 8.04 (s, 1H), 7.13-7.12 (d, J=5.6 Hz, 1H), 5.89-5.34 (m, 1H), 5.28-5.25 (t, J=6.6 Hz, 2H), 5.03-5.00 (t, J=7.0 Hz, 2H), 3.21-3.20 (d, J=6.4 Hz, 2H), 2.6 (s, 3H), 0.97-0.94 (m, 1H), 0.51-0.46 (m, 2H), 0.25-0.22 (m, 2H).

Step 2:
Compound 43_7 was synthesized according to the procedure described in method B and it was obtained as a yellow solid after prep TLC purification. Yield: 79.6%

LCMS: RT=0.566 min, m/z 335.1 [M+H]$^+$

Step 3:
Compound A-43 was synthesized according to the procedure described in method D with trans-cyclohexane-1, 4-diamine (3.0 eq) and it was obtained as a white gum after purification by prep-HPLC (TFA condition). Yield: 24.7%;

LCMS: RT=0.987 min, m/z 369.3 [M+H]+

¹H NMR (CD₃OD, 400 MHz) δ 8.40 (s, 1H), 8.13-8.11 (d, J=6.8 Hz, 1H), 7.31-7.29 (d, J=7.2 Hz, 1H), 5.83-5.80 (t, J=7.0 Hz, 1H), 5.15-5.12 (t, J=6.2 Hz, 2H), 5.06-5.03 (t, J=7.0 Hz, 2H), 4.12 (s, 1H), 3.28-3.26 (d, J=6.4 Hz, 2H), 3.19 (s, 1H), 2.23-2.17 (m, 4H), 1.62-1.60 (m, 4H), 1.06 (s, 1H), 0.53-0.52 (m, 2H), 0.28-0.27 (m, 2H).

Preparation of (R)-tetrahydrofuran-3-yl methanesulfonate (41_4)

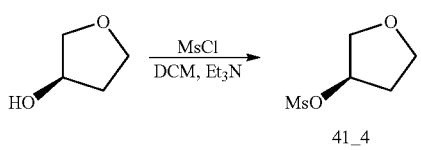

To a solution of (R)-tetrahydrofuran-3-ol (500.00 mg, 5.68 mmol, 1.00 eq) in DCM (5 mL) were added TEA (1.15 g, 11.36 mmol, 2.00 eq) and methanesulfonyl chloride (650.11 mg, 5.68 mmol, 1.00 eq) at 0° C. The mixture was stirred at 20° C. for 1 hr. The mixture was diluted with water (20 mL) and extracted with DCM (10 mL*2). The combined organic layers were concentrated to give 41_4 (900.00 mg, 5.42 mmol, 95.3% yield) as a colorless liquid.

¹H NMR (CDCl₃, 400 MHz) δ 5.33-5.30 (m, 1H), 4.06-3.90 (m, 4H), 3.05 (s, 3H), 2.28-2.23 (m, 2H).

Preparation of (1R, 4S)—N¹-(4-(5-(cyclopropylmethyl)-1-((S)-tetrahydrofuran-3-yl)-1H-pyrazol-4-yl)pyrimidin-2-yl)cyclohexane-1,4-diamine (A-41)

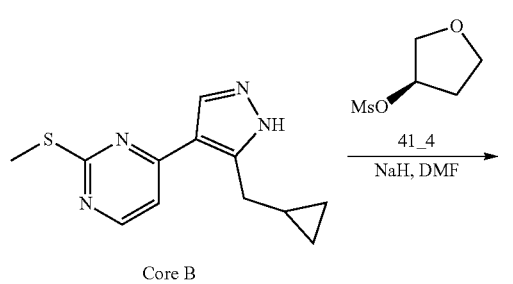

Core B

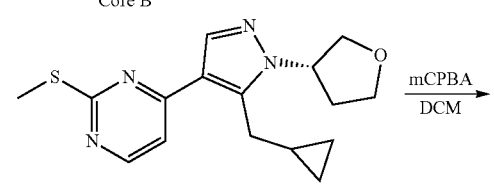

41_6

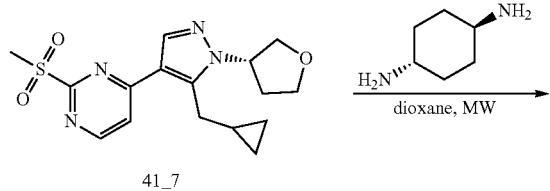

41_7

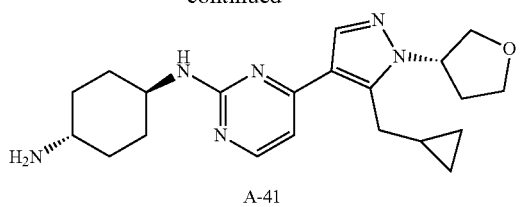

A-41

Step 1:

Compound 41_6 was synthesized according to the procedure described in method A and it was obtained as a yellow solid after purification by prep-HPLC (TFA condition). Yield: 13.1%

¹H NMR (CDCl₃, 400 MHz) δ 8.42-8.40 (d, J=4.4 Hz, 1H), 7.94 (s, 1H), 7.11-7.10 (d, J=7.2 Hz, 1H), 5.04-5.00 (m, 1H), 4.27-4.03 (m, 4H), 3.29-3.27 (d, J=8.4 Hz, 2H), 2.6 (s, 3H), 2.48-2.42 (m, 2H), 1.07-1.02 (m, 1H), 0.53-0.49 (m, 1H), 0.30-0.28 (m, 2H).

Step 2:

Compound 41_7 was synthesized according to the procedure described in method B and it was obtained as a yellow solid after prep TLC purification. Yield: 57.5%

LCMS: RT=0.585 min, m/z 349.2 [M+H]+

Step 3:

Compound A-41 was synthesized according to the procedure described in method D with trans-cyclohexane-1,4-diamine (4.0 eq) and it was obtained as a white gummy solid after purification by prep HPLC (TFA condition). Yield: 17.2%

LCMS: RT=0.969 min, m/z 383.3 [M+H]+

¹H NMR (CD₃OD, 400 MHz) δ 8.26 (s, 1H), 8.10-8.09 (d, J=6.8 Hz, 1H), 7.25-7.23 (d, J=6.8 Hz, 1H), 5.28-5.23 (m, 1H), 4.22-4.12 (m, 3H), 3.99-3.95 (m, 2H), 3.35-3.33 (d, J=6.8 Hz, 2H), 3.19 (s, 1H), 2.47-2.44 (m, 2H), 2.35-2.17 (m, 4H), 1.62-1.57 (m, 4H), 1.14 (s, 1H), 0.58-0.56 (m, 2H), 0.36 (m, 2H).

Preparation of (S)-tetrahydrofuran-3-yl methanesulfonate (42_4)

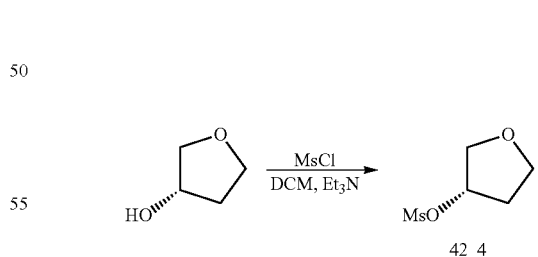

Compound 42_4 was made in the same way as 41_4 from (S)-tetrahydrofuran-3-ol and it was a colorless liquid. Yield: 90.0%

¹H NMR (CDCl₃, 400 MHz) δ 5.33-5.30 (m, 1H), 4.04-3.86 (m, 4H), 3.05 (s, 3H), 2.27-2.22 (m, 2H).

Preparation of (1R, 4R)—N¹-(4-(5-(cyclopropylmethyl)-1-((R)-tetrahydrofuran-3-yl)-1H-pyrazol-4-yl)pyrimidin-2-yl)cyclohexane-1,4-diamine (A-42)

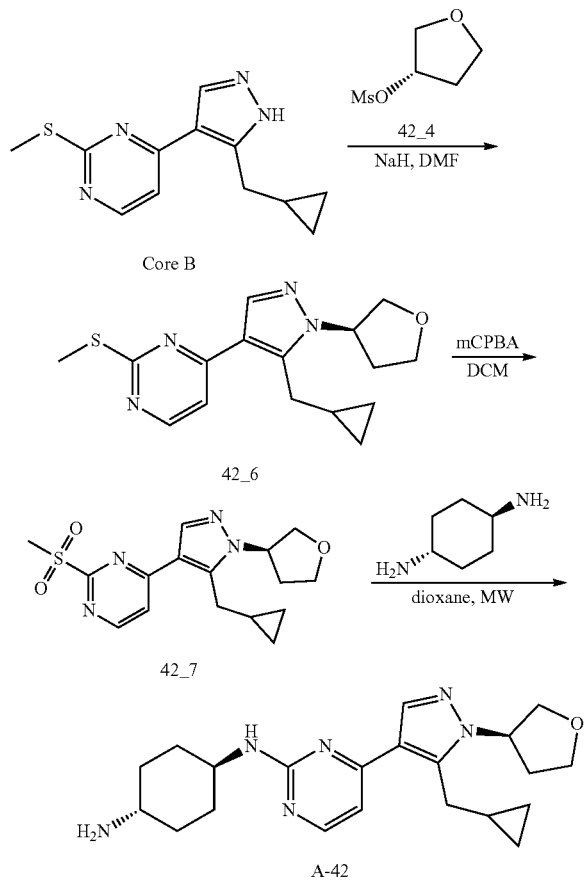

Step 1:

Compound 42_6 was synthesized according to the procedure described in method A and it was obtained as a yellow solid after purification by prep HPLC (TFA condition). Yield: 21.4%

LCMS: RT=0.692 min, m/z 317.1 [M+H]⁺

¹H NMR (CDCl₃, 400 MHz) δ 8.42-8.40 (d, J=4.4 Hz, 1H), 7.95 (s, 1H), 7.12-7.10 (d, J=7.2 Hz, 1H), 5.04-5.00 (m, 1H), 4.27-4.03 (m, 4H), 3.29-3.27 (d, J=8.4 Hz, 2H), 2.6 (s, 3H), 2.47-2.42 (m, 2H), 1.06-1.03 (m, 1H), 0.55-0.50 (m, 1H), 0.31-0.29 (m, 2H).

Step 2:

Compound 42_7 was synthesized according to the procedure described in method B and it was obtained as a yellow solid after prep TLC purification. Yield: 83.2%

LCMS: RT=0.587 min, m/z 349.1 [M+H]⁺

Step 3:

Compound A-42 was synthesized according to the procedure described in method D and it was obtained as a white gummy solid after purification by prep HPLC (TFA condition). Yield: 51.5%

LCMS: RT=1.078 min, m/z 383.3 [M+H]⁺

¹H NMR (CD₃OD, 400 MHz) δ 8.26 (s, 1H), 8.10-8.08 (d, J=6.8 Hz, 1H), 7.28-7.26 (d, J=6.8 Hz, 1H), 5.27-5.24 (m, 1H), 4.22-4.13 (m, 3H), 3.99-3.96 (m, 2H), 3.35-3.31 (t, J=6.8 Hz, 2H), 3.19 (s, 1H), 2.46-2.44 (m, 2H), 2.36-2.17 (m, 4H), 1.63-1.58 (m, 4H), 1.15 (s, 1H), 0.58-0.56 (m, 2H), 0.36 (m, 2H).

Preparation of (1R, 4R)—N¹-(4-(5-(cyclopropylmethyl)-1-(tetrahydro-2H-pyran-3-yl)-1H-pyrazol-4-yl)pyrimidin-2-yl)cyclohexane-1,4-diamine (A-38)

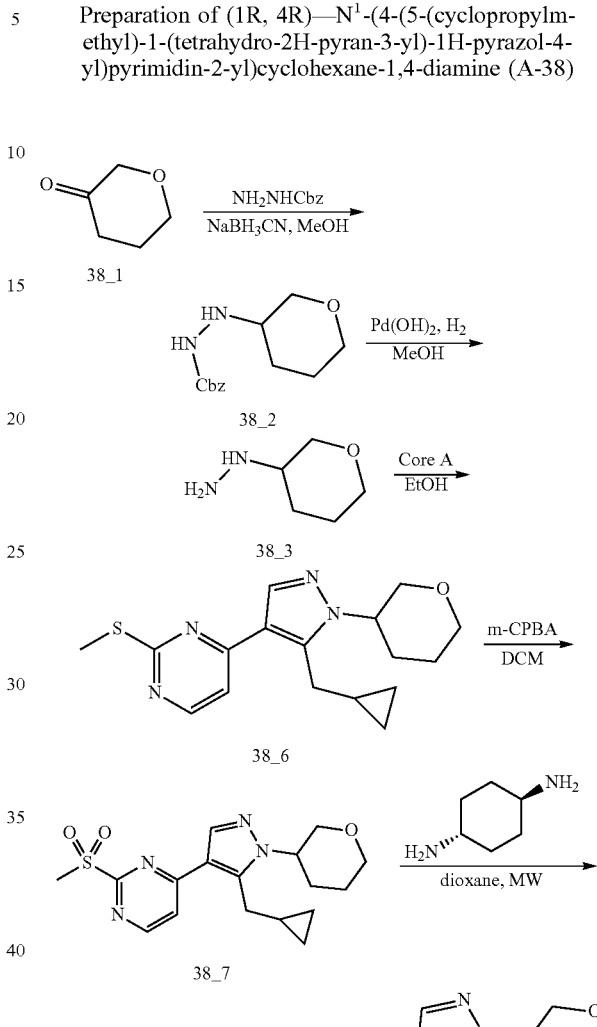

Step 1:

The mixture of 38_1 (1.20 g, 11.99 mmol, 1.40 eq) and benzyl N-aminocarbamate (1.42 g, 8.56 mmol, 1.00 eq) in MeOH (15 mL) was stirred at 30° C. for 2 h. NaBH₃CN (2.69 g, 42.82 mmol, 5.00 eq) was added. The resulting mixture was stirred at 30° C. for 16 h. The mixture was concentrated and diluted with water (50 mL) and EA (50 mL). The organic layer was concentrated and purified by column chromatography (PE:EA=10:1-2:1) to give 38_2 (1.50 g, 5.99 mmol, 70% yield) as a colorless oil.

LCMS: RT=0.568 min, m/z 273.2 [M+H]⁺

¹H NMR (CDCl₃, 400 MHz) δ 7.40-7.35 (m, 5H), 6.25 (s, 1H), 5.26-5.14 (m, 2H), 3.86-3.73 (m, 3H), 3.48-3.30 (m, 2H), 1.91-1.85 (m, 2H), 1.59-1.46 (m, 2H).

Step 2:

To a solution of 38_2 (1.60 g, 6.39 mmol, 1.00 eq) in MeOH (15 mL) was added Pd(OH)₂ (179.54 mg, 1.28 mmol, 0.20 eq). The mixture was stirred at 20° C. under H$_2$ (15 psi) for 16 h. The mixture was filtered and the filtrate was concentrated to give 38_3 (450 mg, crude) as a colorless oil, which was used in the next step directly without purification.

Step 3:

Compound 38_6 was made from Core A and compound 38_4 according to the same procedure as described for the synthesis of Core B and it was obtained as a yellow oil after purification by prep-HPLC (TFA condition). Yield: 40.3%

LCMS: RT=0.851 min, m/z 331.1 [M+H]$^+$ $^1$H NMR (CDCl$_3$, 400 MHz) δ 8.41-8.40 (d, J=5.2 Hz, 1H), 7.92 (s, 1H), 7.10-7.09 (d, J=5.2 Hz, 1H), 4.34-4.33 (m, 1H), 4.03-4.00 (m, 2H), 3.87-3.81 (t, J=10.8 Hz, 1H), 3.51-3.50 (m, 1H), 3.29-3.19 (m, 2H), 2.60 (s, 3H), 2.35 (m, 1H), 2.13 (m, 1H), 1.89-1.85 (m, 2H), 1.06-1.03 (m, 1H), 0.53-0.51 (m, 2H), 0.31 (m, 2H).

Step 4:

Compound 38_7 was synthesized according to the procedure described in method B and it was obtained as a yellow solid after prep TLC purification. Yield: 56.1%

LCMS: RT=0.739 min, m/z 363.1 [M+H]$^+$

Step 5:

Compound A-38 was synthesized according to the procedure described in method D with trans-cyclohexane-1,4-diamine (4.0 eq) and it was obtained as a yellow solid after purification by prep HPLC (basic condition). Yield: 40%

LCMS: RT=1.154 min, m/z 397.3 [M+H]$^+$ $^1$H NMR (CDCl$_3$, 400 MHz) δ 8.18-8.17 (d, J=5.2 Hz, 1H), 7.86 (s, 1H), 6.70-6.69 (d, J=5.2 Hz, 1H), 4.88-4.86 (m, 1H), 4.32-4.29 (m, 1H), 4.02-4.00 (t, J=5.6 Hz, 2H), 3.86-3.81 (m, 2H), 3.51-3.49 (t, J=3.00 Hz, 1H), 3.27-3.19 (m, 2H), 2.81 (s, 1H), 2.34-2.31 (m, 1H), 2.19-2.16 (m, 3H), 2.00-1.97 (m, 4H), 1.38-1.27 (m, 4H), 1.06 (s, 1H), 0.52-0.50 (m, 2H), 0.28 (m, 2H)

General Procedure for the Synthesis of A-n

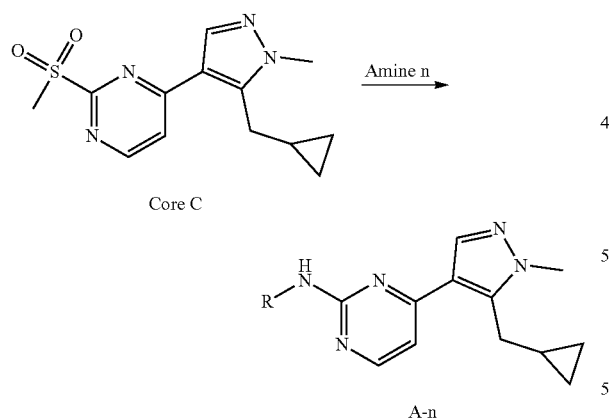

Method E

The reaction mixture of Core C (1.00 eq) and amine n (4.00 eq) in DMSO (8 mL) was stirred at 160° C. for 3 h. The reaction mixture was cooled to rt and poured onto ice-H$_2$O (20 mL). The aqueous layer was extracted with EA (50 mL*3). The combined organic layers were washed with brine (50 mL*3), dried over Na$_2$SO$_4$, filtered and concentrated. The residue was purified by column chromatography to give A-n.

Method F

The reaction mixture of Core C (1.00 eq), TBAF (2.00 eq), K$_2$CO$_3$ (4.00 eq) and amine n (4.00 eq) in DMSO (10 mL) was stirred at 160° C. for 3 h. The reaction mixture was cooled to 15° C. and poured into H$_2$O (20 mL). The aqueous layer was extracted EA (20 mL*3). The combined organic layers were washed with brine (20 mL*3), dried over Na$_2$SO$_4$, filtered and concentrated. The residue was purified by Pre-HPLC (HCl condition) to give A-n.

Method G

The reaction mixture of amine n (1.20 eq) and Core C (1.00 eq) in dioxane (3 mL) was stirred at 130° C. under microwave for 1.5 h. The reaction mixture was poured into H$_2$O (20 mL). The aqueous layer was extracted EA (20 mL*3). The combined organic layers were washed with brine (20 mL*3), dried over Na$_2$SO$_4$, filtered and concentrated. The residue was purified by Pre-HPLC (basic condition) to give A-n.

Preparation of (1R, 4R)—N$^1$-(4-(5-(cyclopropylmethyl)-1-methyl-1H-pyrazol-4-yl)pyrimidin-2-yl) cyclohexane-1,4-diamine (A-14) and (1r, 4r)-N$^1$-(4-(5-(cyclopropylmethyl)-1-methyl-1H-pyrazol-4-yl) pyrimidin-2-yl)-N4,N4-dimethylcyclohexane-1,4-diamine (A-28)

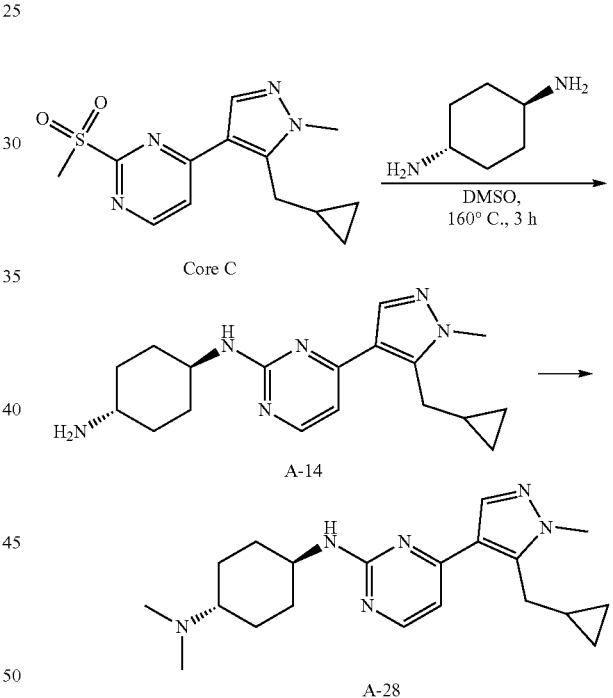

Step 1:

Compound A-14 was prepared according to the procedure described in method G and it was obtained as a yellow solid. Yield: 38.4%

LCMS: RT=2.043 min, m/z 327.2 [M+H]$^+$.

$^1$H NMR (CDCl$_3$, 400 MHz) δ 8.17 (d, J=5.3 Hz, 1H), 7.83 (s, 1H), 6.70 (d, J=5.3 Hz, 1H), 4.91 (s, 1H), 3.93-3.85 (m, 4H), 3.21 (d, J=6.3 Hz, 2H), 2.74 (s, 1H), 2.16 (d, J=4.0 Hz, 2H), 1.94 (d, J=6.7 Hz, 2H), 1.30-1.25 (m, 4H), 1.11-1.10 (m, 1H), 0.50-0.46 (m, 1H), 0.27-0.24 (m, 1H)

Step 2:

To a mixture of A-14 (18.52 mg, 122.53 μmol, 1.00 eq) in EtOH (500 μL) was added 2,3-dihydrobenzotriazol-1-yl-methanol (18.52 mg, 122.53 μmol, 1.00 eq) in one portion at 0° C. The mixture was stirred at 15° C. for 1 hr and NaBH₄ (9.27 mg, 245.06 μmol, 2.00 eq) was added. The resulting mixture was stirred at 15° C. for 1 h, and poured into H₂O (10 mL). The aqueous layer was extracted DCM (20 mL*3). The combined organic layer was washed with brine, dried over NaSO₄ and concentrated. The residue was purified by prep HPLC (basic condition) to give A-28 (5.00 mg, 14.10 μmol, 11.5% yield, 100% purity) as a white solid.

LCMS: RT=2.535 min, m/z 355.2 [M+H]⁺

¹H NMR (CDCl₃, 400 MHz) δ 8.10 (d, J=5.2 Hz, 1H), 7.76 (s, 1H), 6.63 (d, J=5.2 Hz, 1H), 4.78 (d, J=3.6 Hz, 1H), 3.81 (s, 3H), 3.77-3.71 (m, 1H), 3.13 (d, J=6.4 Hz, 2H), 2.27 (s, 6H), 2.17 (d, J=12.4 Hz, 2H), 1.93 (d, J=11.6 Hz, 2H), 1.36-1.31 (m, 2H), 1.23-1.17 (m, 2H), 1.04-1.02 (m, 1H), 0.44-0.39 (m, 2H), 0.20-0.18 (m, 2H).

Preparation of 8-amino-1,3-diazaspiro[4.5]decane-2,4-dione hydrochloride (amine-19)

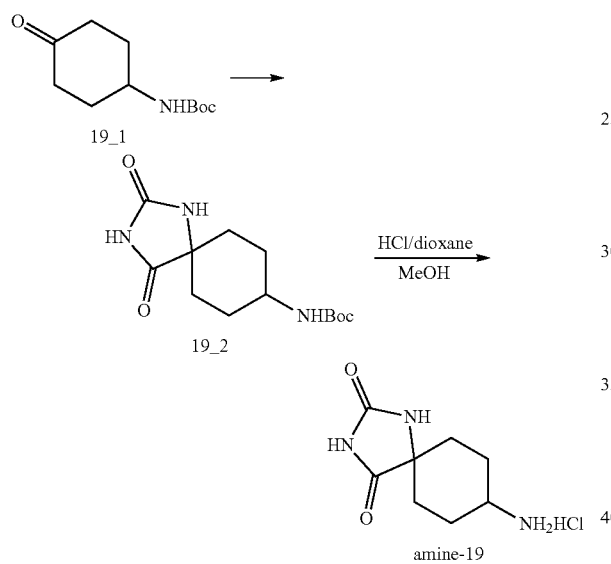

Step 1:

A solution of NaCN (2.75 g, 56.02 mmol, 2.39 eq) in H₂O (10 mL) was added to the mixture of compound 19_1 (5.00 g, 23.44 mmol, 1.00 eq) and (NH₄)₂CO₃ (4.96 g, 51.57 mmol, 2.20 eq) in EtOH (25 mL) and H₂O (25 mL). The reaction mixture was stirred at 10° C. for 16 hours and then at 70° C. for another 24 hours. TLC (PE:EA=3:1) showed that reactant was consumed (Rf=0.55) and a major spot formed (Rf=0.25). The reaction mixture was allowed to cool down and filtered. The filter cake was washed with H₂O (100 mL) and dried. Compound 19_2 (4.00 g, 14.12 mmol, 60.2% yield) was obtained as a white solid.

¹H NMR (DMSO-d6, 400 MHz) δ 10.51 (s, 1H), 8.48 (s, 1H), 6.70-6.72 (d, J=8.0 Hz, 1H), 3.16 (s, 1H), 1.79-1.76 (m, 2H), 1.65-1.64 (d, J=4.0 Hz, 2H), 1.62-1.52 (m, 2H), 1.60-1.59 (m, 1H), 1.37 (s, 11H).

Step 2:

To the mixture of compound 19_2 (1.00 g, 3.53 mmol, 1.00 eq) in MeOH (10 mL) was added HCl/dioxane (4 M, 10 mL, 11.33 eq) at 0° C. and the reaction mixture was stirred at 10° C. for 16 hour. LCMS showed the consumption of reactant. The reaction mixture was concentrated to give Amine-19 (700.00 mg, 3.19 mmol, 90.3% yield, HCl) as a white solid.

¹H NMR (DMSO-d6, 400 MHz) δ 8.52 (s, 1H), 8.21 (s, 3H), 3.06 (s, 1H), 1.96-1.89 (m, 1H), 1.76-1.59 (m, 6H).

Preparation of 8-((4-(5-(cyclopropylmethyl)-1-methyl-1H-pyrazol-4-yl)pyrimidin-2-yl)amino)-1,3-diazaspiro[4.5]decane-2,4-dione (A19_4) and (1-amino-4-((4-(5-(cyclopropylmethyl)-1-methyl-1H-pyrazol-4-yl)pyrimidin-2-yl)amino)cyclohexyl)methanol (A-19)

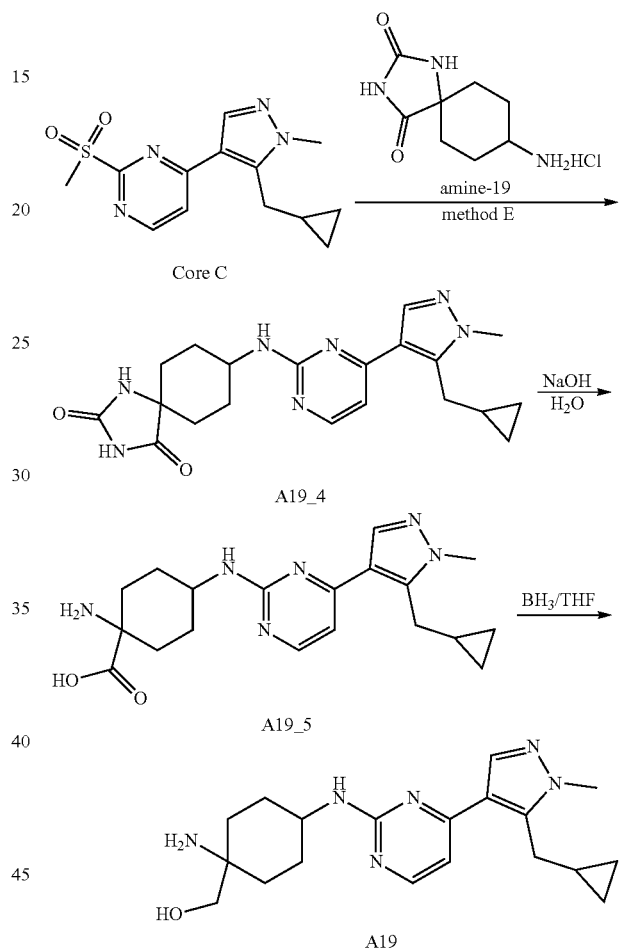

Step 1:

Compound A19_4 was prepared according to the procedure described in method E with amine-19 (4 eq) and DIEA (4 eq) and it was as a white solid after purification by prep HPLC (basic condition). Yield: 72.2%

LCMS: RT=0.573 min, m/z 397.2 [M+H]⁺

¹H NMR (CD₃OD, 400 MHz) δ 8.22 (s, 1H), 8.14-8.09 (m, 1H), 7.24 (d, J=5.2 Hz, 1H), 5.19 (d, J=6.8 Hz, 1H), 4.21 (s, 1H), 3.94 (s, 3H), 3.30 (d, J=6.8 Hz, 2H), 2.20 (d, J=6.0 Hz, 2H), 2.09-2.05 (t, 2H), 1.86 (d, J=14.8 Hz, 2H), 1.69-1.65 (m, 2H), 1.25-1.21 (m, 1H), 0.60 (d, J=7.6 Hz, 2H), 0.39-0.35 (m, 2H),

Step 2:

Compound A19_4 (95.00 mg, 240.23 μmol, 1.00 eq) was added to NaOH/H₂O (3 M, 640.60 μL, 8.00 eq) and the reaction mixture was stirred at 120° C. for 16 h. The reaction mixture was cooled to 15° C. and poured into H₂O (20 mL). The aqueous layer was adjusted to pH=7 with 2N HCl solution. The mixture was concentrated. The crude product was triturated with MeOH (50 mL*3). The filtrate was concentrated to give 19_5 (300.00 mg, crude) as a white solid.

LCMS: RT=1.148 min, m/z 371.2 [M+H]$^+$ $^1$H NMR (CD$_3$OD, 400 MHz) δ 8.15 (d, J=5.2 Hz, 1H), 7.95-7.93 (m, 1H), 6.89-6.85 (m, 1H), 4.03 (s, 1H), 3.91 (s, 3H), 3.28 (s, 2H), 2.32-2.25 (m, 2H), 2.16-2.13 (d, J=9.6 Hz, 2H), 1.99-1.95 (d, J=9.6 Hz, 2H), 1.57-1.54 (d, J=14 Hz, 2H), 1.37 (s, 1H), 0.51-0.48 (m, 2H), 0.31-0.27 (m, 2H), Step 3:

To the mixture of 19_5 (330.00 mg, 890.81 μmol, 1.00 eq) in THF (500 μL) was added BH$_3$ (1M, 7.13 mL, 8.00 eq) and the reaction mixture was stirred at 100° C. for 16 h. The reaction mixture was cooled to 15° C. and poured into MeOH (20 mL). The mixture was concentrated. The crude product was purified by Pre-HPLC (basic condition) to give A-19 (23.00 mg, 64.52 μmol, 7.2% yield, 100% purity) as a white solid.

LCMS: RT=1.060 min, m/z 357.2 [M+H]$^+$ $^1$H NMR (CD$_3$OD, 400 MHz) δ 8.12 (d, J=5.6 Hz, 1H), 7.93 (s, 1H), 6.85-6.82 (m, 1H), 3.88-3.80 (m, 4H), 3.28 (s, 2H), 3.39 (s, 2H), 3.27 (d, J=6.4 Hz, 2H), 2.03-1.94 (m, 3H), 1.68-1.58 (m, 6H), 1.13 (d, J=5.2 Hz, 1H), 0.50-0.47 (m, 2H), 0.30-0.28 (m, 2H).

Preparation of 8-((4-(5-(cyclopropylmethyl)-1-methyl-1H-pyrazol-4-yl)pyrimidin-2-yl)amino)-3-oxa-1-azaspiro[4,5]decan-2-one (A-26)

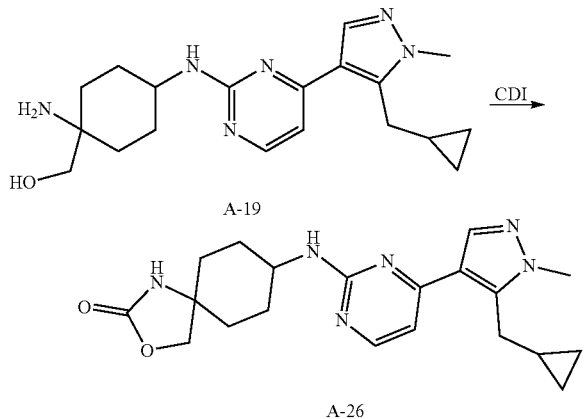

To the mixture of A-19 (20.00 mg, 56.11 μmol, 1.00 eq) in THF (500 μL) was added CDI (9.1 mg, 56.11 μmol, 1.00 eq) and the reaction mixture was stirred at 25° C. for 16 h. The reaction mixture was concentrated. The crude product was purified by prep HPLC (basic condition) to give A-26 (4.00 mg, 10.46 μmol, 18.6% yield, 100% purity) as a white solid.

LCMS: RT=2.210 min, m/z 383.2 [M+H]$^+$ $^1$H NMR (CDCl$_3$, 400 MHz) δ 8.19 (s, 1H), 7.84 (s, 1H), 6.74 (s, 1H), 5.97 (s, 1H), 5.02 (s, 1H), 4.15 (s, 1H), 3.89 (s, 4H), 3.17 (s, 2H), 2.16-2.13 (d, J=12.4 Hz, 2H), 1.98-1.95 (d, J=13.2 Hz, 2H), 1.72-1.68 (d, J=12.8 Hz, 2H), 1.48-1.45 (d, J=10.08 Hz, 2H), 1.10 (s, 1H), 0.49 (s, 2H), 0.24 (s, 2H).

Preparation of (1R, 4R)—N$^1$-(4-(5-(cyclopropylmethyl)-1-methyl-1H-pyrazol-4-yl)pyrimidin-2-yl)-N4-methylcyclohexane-1,4-diamine (A-27)

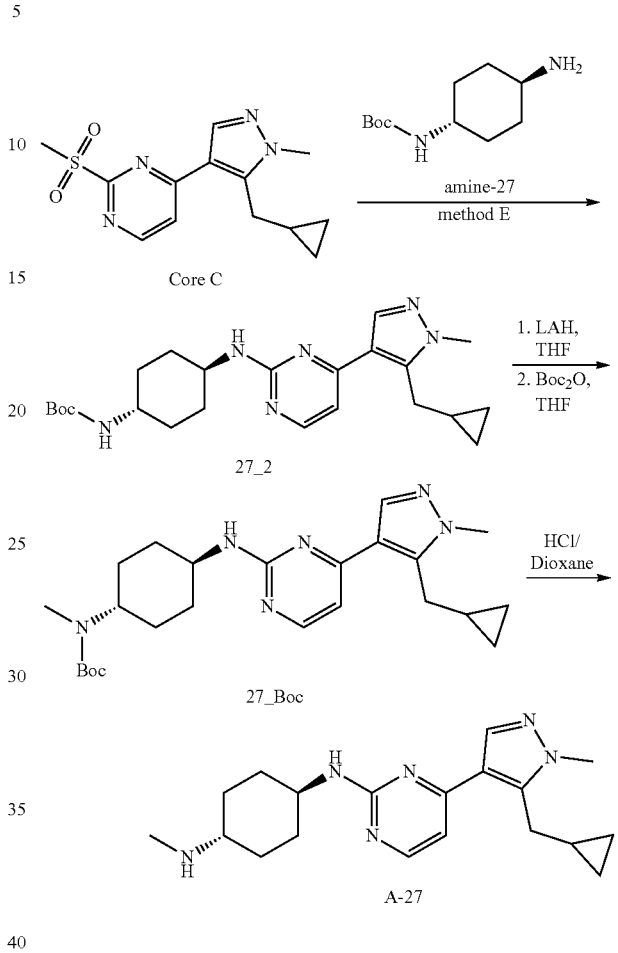

Step 1:

Compound 27_2 was made according to the procedure described in method E with amine-27 (1.0 eq) and DIEA (10 eq) at 160° C. for 6 h and it was obtained as a yellow solid after purification by prep HPLC (TFA). Yield: 41.1%

$^1$H NMR (CDCl$_3$, 400 MHz) δ 8.18 (d, J=5.2 Hz, 1H), 7.83 (s, 1H), 6.71 (d, J=5.6 Hz, 1H), 4.87 (s, 1H), 4.41 (s, 1H), 3.89-3.82 (m, 4H), 3.49 (s, 1H), 3.19 (d, J=6.3 Hz, 2H), 2.19-2.05 (m, 4H), 1.46 (s, 9H), 1.35-1.29 (m, 7H), 1.26 (m, 2H), 1.23 (m, 2H), 0.50-0.46 (m, 2H), 0.26-0.24 (m, 2H)

Step 2:

To a solution of 27_2 (100.00 mg, 234.44 μmol, 1.00 eq) in THF (4.00 mL) was added LiAlH$_4$ (26.69 mg, 703.32 μmol, 3.00 eq) at 0° C. The mixture was stirred at 70° C. for 3 h. The mixture was cooled to 0° C. and then quenched with aq. NH$_4$Cl (3 drops). The resulting solution was dried over Na$_2$SO$_4$ and then concentrated. The residue was failed to be purified by prep-HPLC. So A-27 (70 mg, crude) will be purified after protected with Boc group. To the solution of A-27 (crude) in THF (1 mL) was added (Boc$_2$)$_2$ (200 mg, 2 eq). After stirring for 1 hour at 20° C., the reaction mixture was purified by prep-TLC (EA) to get 27_Boc (30 mg, 29.13% yield total), which was used for next step directly.

Step 3:

To a solution of 27_Boc (30.00 mg, 68.09 μmol, 1.00 eq) in DCM (100 μL) was added HCl/dioxane (4 M, 85 μL, 5.00 eq) in one portion at 0° C. and the mixture was stirred at 15°

C. for 5 h. The reaction mixture was concentrated to give A-27 (12.00 mg, 30.88 μmol, 45.35% yield, 97% purity, HCl) as a light yellow solid. Yield: 45.4%

LCMS: RT=2.558 min, m/z 341.2 [M+H]+

¹H NMR (CD₃OD, 400 MHz) δ 8.26 (s, 1H), 8.14 (d, J=6.4 Hz, 1H), 7.31 (d, J=6.4 Hz, 1H), 4.19-4.12 (m, 1H), 3.95 (s, 3H), 3.71 (s, 2H), 3.17 (s, 1H), 2.76 (s, 3H), 2.31-2.20 (m, 4H), 1.65 (m, 4H), 1.21 (s, 1H), 0.51 (s, 2H), 0.37 (d, J=3.2 Hz, 2H).

Preparation of N-((1R,4R)-4-aminocyclohexyl)-2-methoxyacetamide hydrochloride (amine-29)

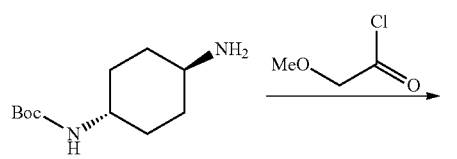

29_1

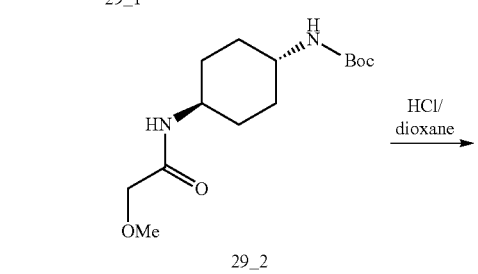

29_2

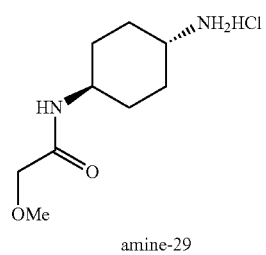

amine-29

Step 1:

To a mixture of 29_1 (658.25 mg, 3.07 mmol, 1.0 eq) and 2-methoxyacetyl chloride (500 mg, 4.61 mmol, 1.5 eq) in DCM (5 mL) was added DIEA (310.82 mg, 3.07 mmol, 1.00 eq) in at 0° C. Then the reaction mixture was stirred at 15° C. for 2 hours. The reaction mixture was concentrated under vacuum. The residue was purified by column chromatography to give 29_2 (490.00 mg, 1.71 mmol, 55.7% yield) as a white solid.

¹H NMR (CDCl₃, 400 MHz) δ 3.80 (s, 1H), 3.74-3.67 (m, 1H), 3.40 (s, 1H), 3.33 (s, 3H), 1.97-1.87 (m, 4H), 1.37 (s, 9H), 1.22-1.12 (m, 3H)

Step 2:

Compound 29-2 was deprotected in a similar manner as shown in step 3 of the synthesis of A27 and Amine-29 was obtained as a white solid. Yield: 91.9%

1H NMR (CD₃OD, 400 MHz) 4.05 (s, 1H), 374 (s, 2H), 3.70-3.69 (m, 1H), 3.36 (s, 3H), 3.28-3.27 (m, 1H), 3.09-3.07 (m, 1H), 2.07-2.04 (m, 2H), 1.94-1.92 (m, 2H), 1.56-1.40 (m, 4H)

Preparation of N-((1R, 4R)-4-((4-(5-(cyclopropylmethyl)-1-methyl-1H-pyrazol-4-yl)pyrimidin-2-yl)amino)cyclohexyl)-2-methoxyacetamide (A29_1)

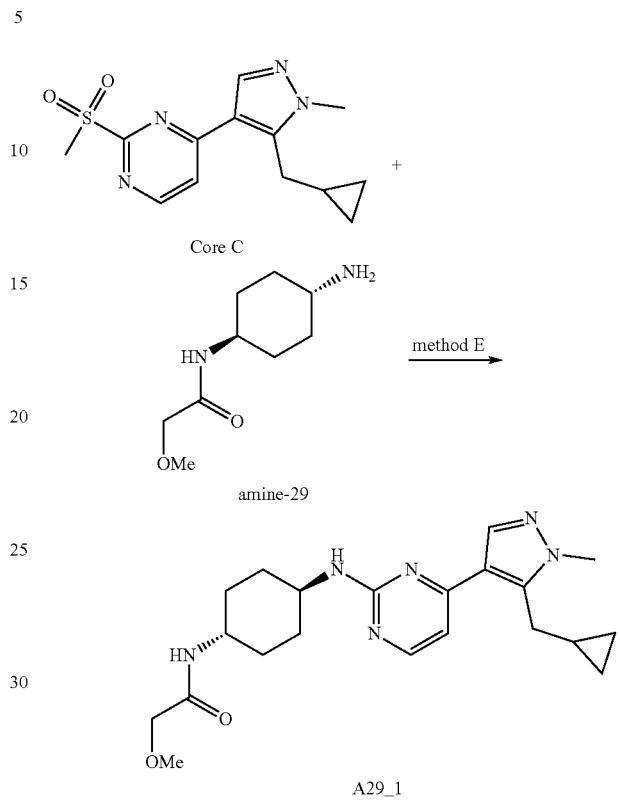

Compound A29_1 was made according to the procedure described in method E with amine-29 (1.0 eq) and DIEA (4 eq) and it was obtained as a light yellow solid after purification by prep HPLC (basic condition). Yield: 27.4%

LCMS: RT=2.535 min, m/z 355.2 [M+H]+

1H NMR (CDCl₃, 400 MHz) δ 8.20 (d, J=5.2 Hz, 1H), 7.85 (s, 1H), 6.73 (d, J=5.2 Hz, 1H), 6.40 (d, J=8.0 Hz, 1H), 4.92 (s, 1H), 3.91 (m, 7H), 3.45 (m, 3H), 3.27-3.20 (m, 2H), 2.21 (s, 2H), 2.10 (s, 2H), 1.45-1.36 (m, 4H), 1.13-1.12 (m, 1H), 0.53-0.48 (m, 2H), 0.28-0.26 (q, J=4.9 Hz, 2H)

Preparation of (1R, 4R)—N¹-(4-(5-(cyclopropylmethyl)-1-methyl-1H-pyrazol-4-yl)pyrimidin-2-yl)-N4-(2-methoxyethyl)cyclohexane-1,4-diamine (A-29)

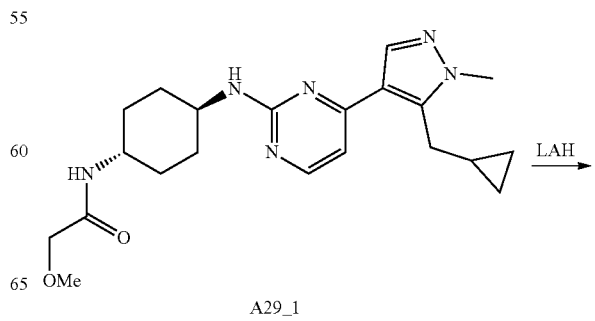

A29_1

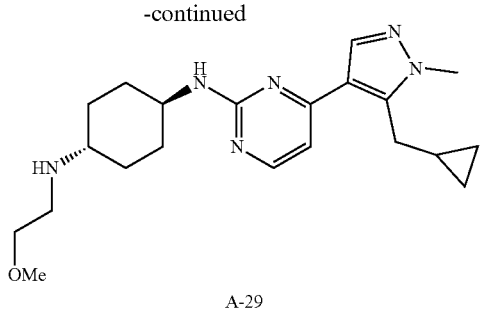

A-29

To a mixture of LAH (40.00 mg, 1.05 mmol, 10.50 eq) in THF (4 mL) was added a solution of A29_1 (40.00 mg, 100.38 µmol, 1.00 eq) in THF (1 mL) at 15° C. The mixture was stirred at 70° C. for 36 hr. The reaction mixture was cooled down and poured into H₂O (0.1 mL). 1N NaOH (0.1 mL) was added and filtered. The filtrate was concentrated. The crude product was purified by Pre-HPLC (basic condition) to give A-29 (4.00 mg, 9.88 µmol, 9.8% yield, 95.0% purity) as a yellow solid.

LCMS: RT=2.535 min, m/z 355.2 [M+H]⁺

¹H NMR (CDCl₃, 300 MHz) δ 8.17 (d, J=6.8 Hz, 1H), 7.82 (s, 1H), 6.76-6.69 (m, 1H), 4.88 (d, J=10.4 Hz, 1H), 3.89 (s, 4H), 3.54-3.50 (m, 2H), 3.38 (s, 3H), 3.22 (d, J=8.40 Hz, 2H) 2.84-2.81 (m, 2H), 2.49 (s, 1H) 2.19 (s, 2H), 2.01 (s, 1H) 1.38 (s, 4H), 1.07 (s, 1H) 0.49-0.43 (m, 2H), 0.25-0.20 (m, 2H)

Preparation of (1R,4R)-4-(piperidin-1-yl)cyclohexanamine hydrochloride

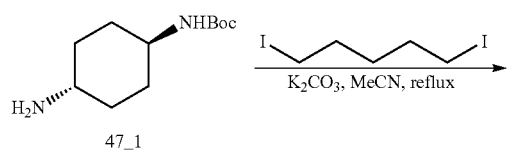

47_1

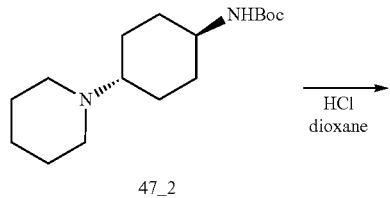

47_2

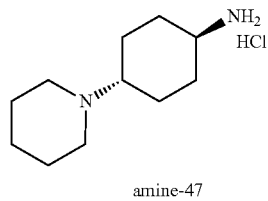

amine-47

Step 1:

A mixture of 47_1 (200.00 mg, 933.27 µmol, 1.00 eq), 1,5-diiodopentane (302.32 mg, 933.27 µmol, 1.00 eq) and K₂CO₃ (515.95 mg, 3.73 mmol, 4.00 eq) in MeCN (10 mL) was stirred at 90° C. for 16 hours. The mixture was filtered and the filtrate was concentrated to give 47_2 (300 mg, crude) as a white solid and it was used in next step directly.

Step 2:

Crude 47_2 was deprotected in a similar manner as shown in step 3 of the synthesis of A27 and amine-47 was obtained as a white solid.

¹H NMR (D₂O, 400 MHz) δ 3.55-3.10 (m, 6H), 2.16-2.08 (m, 4H), 1.59-1.41 (m, 10H).

Preparation of 4-(5-(cyclopropylmethyl)-1-methyl-1H-pyrazol-4-yl)-N-((1R,4R)-4-(piperidin-1-yl)cyclohexyl)pyrimidin-2-amine (A-47)

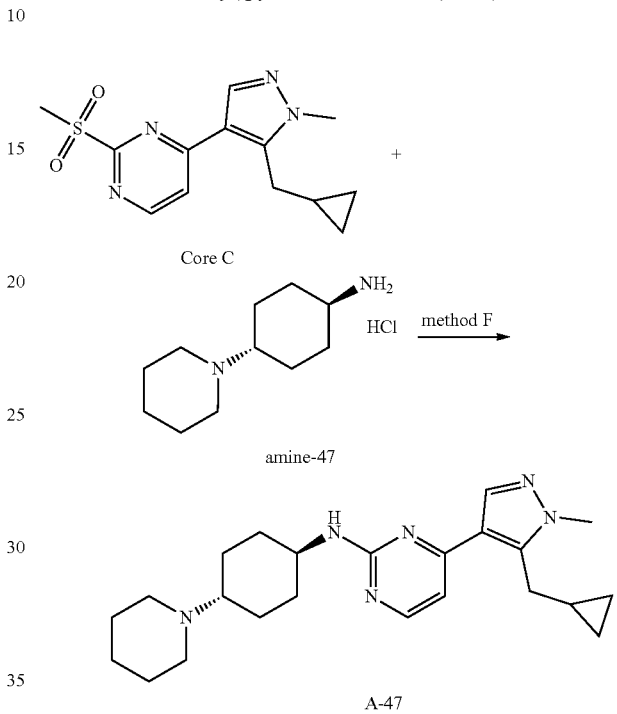

A-47

Compound A-47 was prepared according to the procedure described in method F with amine-47 and it was obtained as a white solid after purification by prep HPLC (HCl condition). Yield: 49.3%

LCMS: RT=1.530 min, m/z 395.2 [M+H]⁺

¹H NMR (CD₃OD, 400 MHz) δ 8.21 (s, 1H), 8.06 (d, J=6.8 Hz, 1H), 7.24-7.21 (m, 1H), 4.10 (s, 1H), 3.88 (s, 3H), 3.49 (d, J=11.2 Hz, 2H), 3.23 (s, 2H), 3.06-3.00 (m, 4H), 2.26 (d, J=10 Hz, 4H), 1.96-1.57 (m, 10H), 1.15 (s, 1H), 0.50 (s, 2H), 0.31-0.30 (m, 2H)

Preparation of (1R,4R)-4-morpholinocyclohexanamine hydrochloride (amine-48)

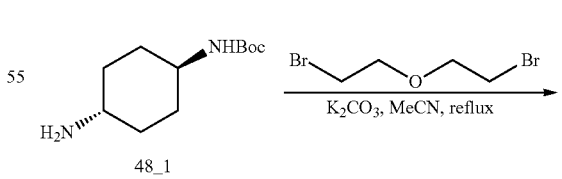

48_1

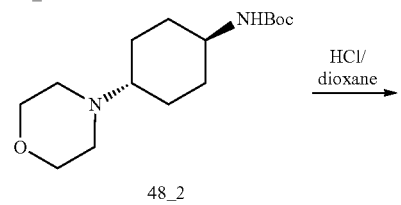

48_2

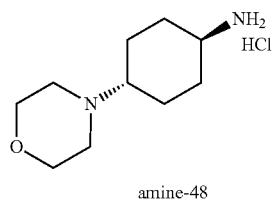

amine-48

Crude amine-48 was synthesized in a similar manner as described for the synthesis of amine-47 and it was obtained as a yellow solid.

$^1$H NMR (D20, 400 MHz) δ 3.87 (s, 4H), 3.24-3.11 (m, 6H), 2.20-2.12 (m, 4H), 1.59-1.39 (m, 5H).

Preparation of 4-(5-(cyclopropylmethyl)-1-methyl-1H-pyrazol-4-yl)-N-((1r, 4r)-4-morpholinocyclohexyl)pyrimidin-2-amine (A-48)

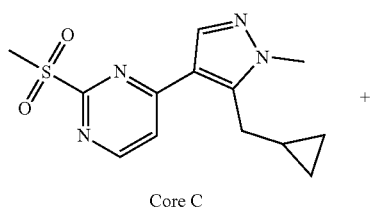

Core C

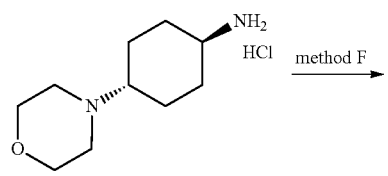

amine-48

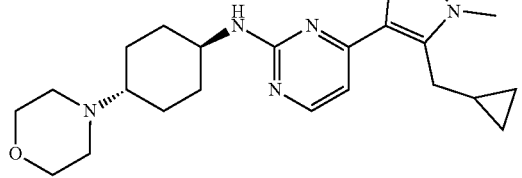

A-48

Compound A-48 was prepared according to the procedure described in method F with amine-48 with TBAF (1.0 eq) and it was obtained as a white solid after purification by prep HPLC (HCl condition). Yield: 51.2%

LCMS: RT=2.095 min, m/z 397.3 [M+H]$^+$ $^1$H NMR (CD$_3$OD, 400 MHz) δ 8.16 (s, 1H), 8.01 (s, 1H), 7.19 (s, 1H), 4.06-3.97 (m, 3H), 3.83-3.78 (m, 5H), 3.51-3.42 (m, 2H), 3.24 (s, 1H), 3.14-3.12 (m, 1H), 2.29-2.19 (m, 4H), 1.69-1.63 (m, 2H), 1.54-1.48 (m, 2H), 1.02 (s, 1H), 0.45 (s, 2H), 0.25 (s, 2H).

Preparation of (1R, 4R)-4-(pyrrolidin-1-yl)cyclohexanamine hydrochloride (amine-49)

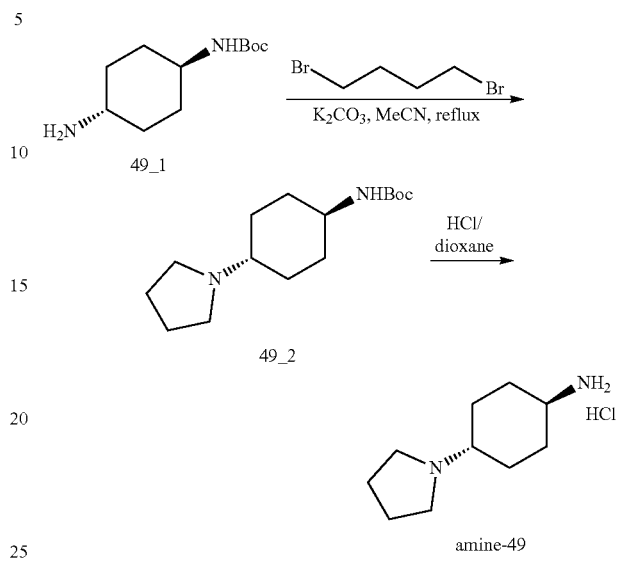

amine-49

Crude amine-49 was synthesized in a similar manner as described for the synthesis of amine-47 and it was obtained as a white solid.

$^1$H NMR (D20, 400 MHz) δ 3.55-3.53 (m, 3H), 3.13-2.99 (m, 4H), 2.21-2.09 (m, 2H), 2.06-1.99 (m, 7H), 1.49-1.40 (m, 4H).

Preparation of 4-(5-(cyclopropylmethyl)-1-methyl-1H-pyrazol-4-yl)-N-((1R, 4R)-4-(pyrrolidin-1-yl)cyclohexyl)pyrimidin-2-amine (A-49)

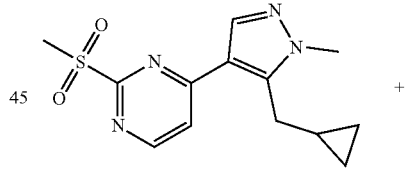

Core C

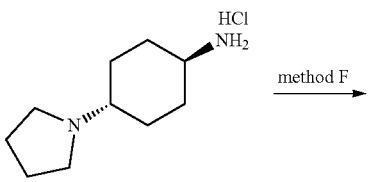

amine-49

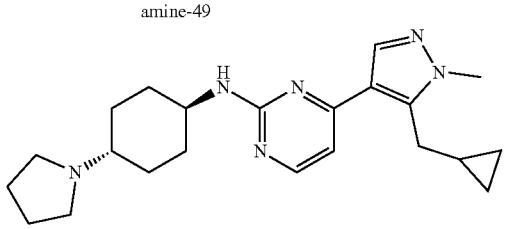

A-49

Compound A-49 was prepared according to the procedure described in method F with amine-49 and it was obtained as a white solid after purification by prep HPLC (HCl condition). Yield: 89.3%

LCMS: RT=2.607 min, m/z 381.3 [M+H]+

1H NMR (CDCl3, 400 MHz) δ 8.16 (s, 1H), 8.01 (s, 1H), 7.19 (s, 1H), 4.06 (s, 1H), 3.83 (s, 3H), 3.08 (s, 2H), 2.26-1.48 (m, 13H), 1.09 (s, 1H), 0.45 (s, 2H), 0.25 (s, 2H).

Preparation of (1R, 4R)-4-(azetidin-1-yl)cyclohexanamine hydrochloride (amine-50)

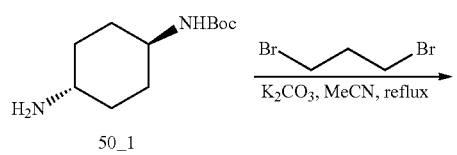

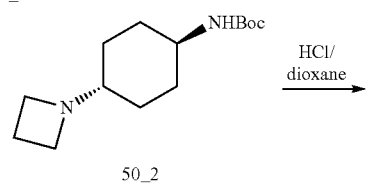

Crude amine-50 was synthesized in a similar manner as described for the synthesis of amine-47 and it was obtained as a white solid 1H NMR (CDCl3, 400 MHz) δ 4.15-4.08 (m, 2H), 3.65-3.12 (m, 1H), 2.28-2.03 (m, 6H), 1.50-1.42 (m, 4H), 1.26-1.20 (m, 1H).

Preparation of N-((1R, 4R)-4-(azetidin-1-yl)cyclohexyl)-4-(5-(cyclopropylmethyl)-1-methyl-1H-pyrazol-4-yl)pyrimidin-2-amine (A-50)

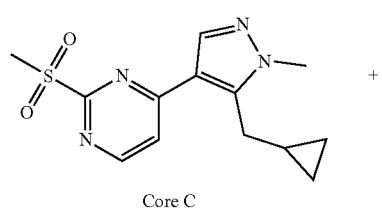

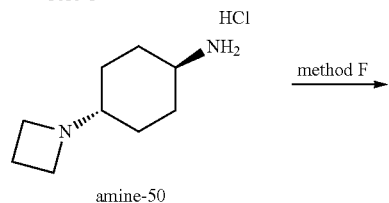

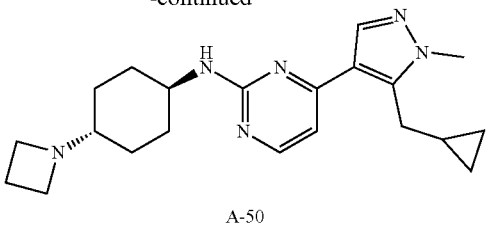

Compound A-50 was prepared according to the procedure described in method F with amine-50 and it was obtained as a white solid after purification by prep HPLC (Basic condition). Yield: 16%

LCMS: RT=2.494 min, m/z 367.3 [M+H]+

1H NMR (CDCl3, 400 MHz) δ 8.17 (d, J=6.8 Hz, 1H), 7.88 (s, 1H), 6.70 (d, J=6.8 Hz, 1H), 4.86 (d, J=11.6 Hz, 1H), 3.91 (m, 4H), 3.25-3.20 (m, 5H), 2.31-2.07 (m, 6H), 2.05-2.02 (m, 2H), 1.24-1.10 (m, 5H), 0.47-0.43 (m, 2H), 0.25-0.22 (s, 2H).

Preparation of (1R, 4R)—N1-(4-(5-(cyclobutylmethyl)-1-methyl-1H-pyrazol-4-yl)pyrimidin-2-yl)cyclohexane-1,4-diamine (A-45)

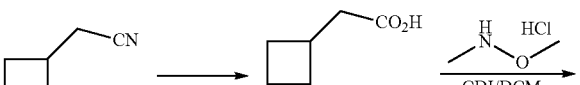

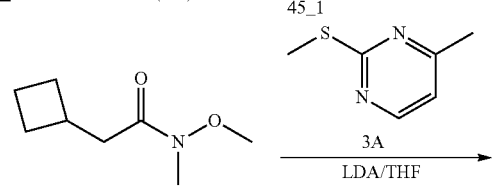

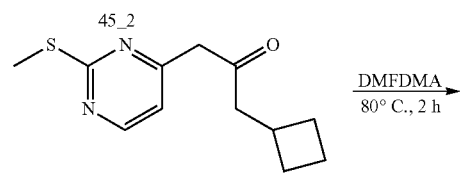

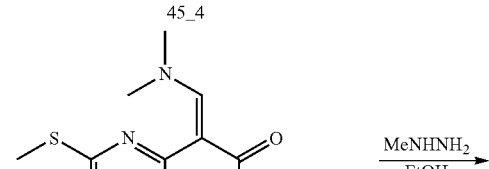

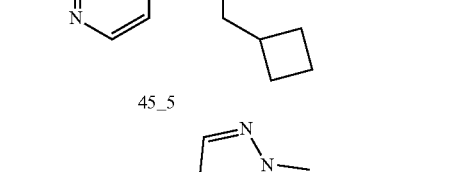

-continued

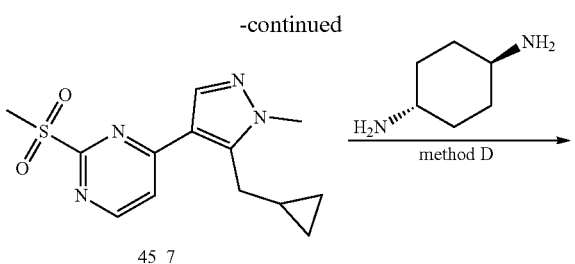

45_7

A_45

Step 1:

A solution of 2-cyclobutylacetonitrile (1.00 g, 10.51 mmol, 1.00 eq) in HCl (6 M, 10.00 mL, 5.71 eq) was stirred at 120° C. for 16 h. The mixture was diluted with water (50 mL) and extracted with EA (20 mL*2). The combined organic layer was washed with water (40 mL), dried and concentrated to give 45_1 (750 mg, 6.57 mmol, 62.5% yield) as a colorless liquid $^1$H NMR (CDCl3, 400 MHz) δ 2.72-2.68 (m, 1H), 2.47-2.45 (d, J=8.0 Hz, 2H), 2.17-2.15 (m, 2H), 1.90-1.88 (m, 2H), 1.75-1.70 (m, 2H).

Step 2-4:

Compound 45_5 was synthesized in a similar manner as described for the synthesis of Core A in scheme 1.1.

Compound 45_2 was obtained as a colorless liquid.

$^1$H NMR (CDCl$_3$, 400 MHz) δ 3.68 (s, 3H), 3.16 (s, 3H), 3.75-3.71 (m, 1H), 2.55-2.53 (m, 2H), 2.16-2.13 (m, 3H), 1.89-1.87 (m, 2H), 1.73-1.68 (m, 2H).

Compound 45_4 was obtained as a yellow oil

LCMS: RT=0.795 min, m/z 237.1 [M+H]$^+$

Compound 45_5 was obtained as a dark brown solid:

$^1$H NMR (CDCl$_3$, 400 MHz) δ 8.39-8.38 (d, J=4.8 Hz, 1H), 8.02 (s, 1H), 7.59 (s, 1H), 6.96-6.92 (m, 1H), 2.96 (s, 3H), 2.89 (m, 5H), 2.72-2.68 (m, 1H), 2.57 (s, 3H), 2.10-2.05 (m, 2H), 1.87-1.82 (m, 4H).

Step 5-6:

Compound 45_7 was synthesized in a similar manner as described for the synthesis of Core C in scheme 1.2.

Compound 45_6 was obtained as a yellow oil after purification by prep HPLC (TFA condition). Yield: 21.2%;

$^1$H NMR (CDCl$_3$, 400 MHz) δ 8.41-8.39 (d, J=7.2 Hz, 1H), 7.88 (s, 1H), 7.09-7.07 (d, J=6.8 Hz, 1H), 3.89 (s, 3H), 3.35-3.33 (d, J=9.6 Hz, 2H), 2.72-2.67 (m, 1H), 2.6 (s, 3H), 2.02-1.98 (m, 2H), 1.84-1.76 (m, 4H).

Compound 45_7 was obtained as a yellow oil after purification by pre-TLC. Yield: 86.6%;

LCMS: RT=0.706 min, m/z 307.2 [M+H]$^+$

Step 7:

Compound A-45 was made according to the procedure described in method D with trans-cyclohexane-1, 4-diamine (4.0 eq) and it was obtained as a yellow solid after purification by prep HPLC (basic condition). Yield: 21.9%;

LCMS: RT=0.539 min, m/z 341.3 [M+H]$^+$;

$^1$H NMR (CDCl$_3$, 400 MHz) δ 8.18-8.17 (d, J=5.2 Hz, 1H), 7.82 (s, 1H), 6.69-6.68 (d, J=5.2 Hz, 1H), 4.85-4.83 (d, J=8.0 Hz, 1H), 3.91-3.84 (m, 4H), 3.33-3.31 (d, J=7.6 Hz, 2H), 2.75-2.68 (m, 2H), 2.18-2.17 (m, 2H), 2.00-1.93 (m, 4H), 1.80-1.77 (m, 4H), 1.31-1.26 (m, 4H).

Preparation of (1R, 4R)—N$^1$-(4-(5-(cyclopentylmethyl)-1-methyl-1H-pyrazol-4-yl)pyrimidin-2-yl)cyclohexane-1,4-diamine (A-46)

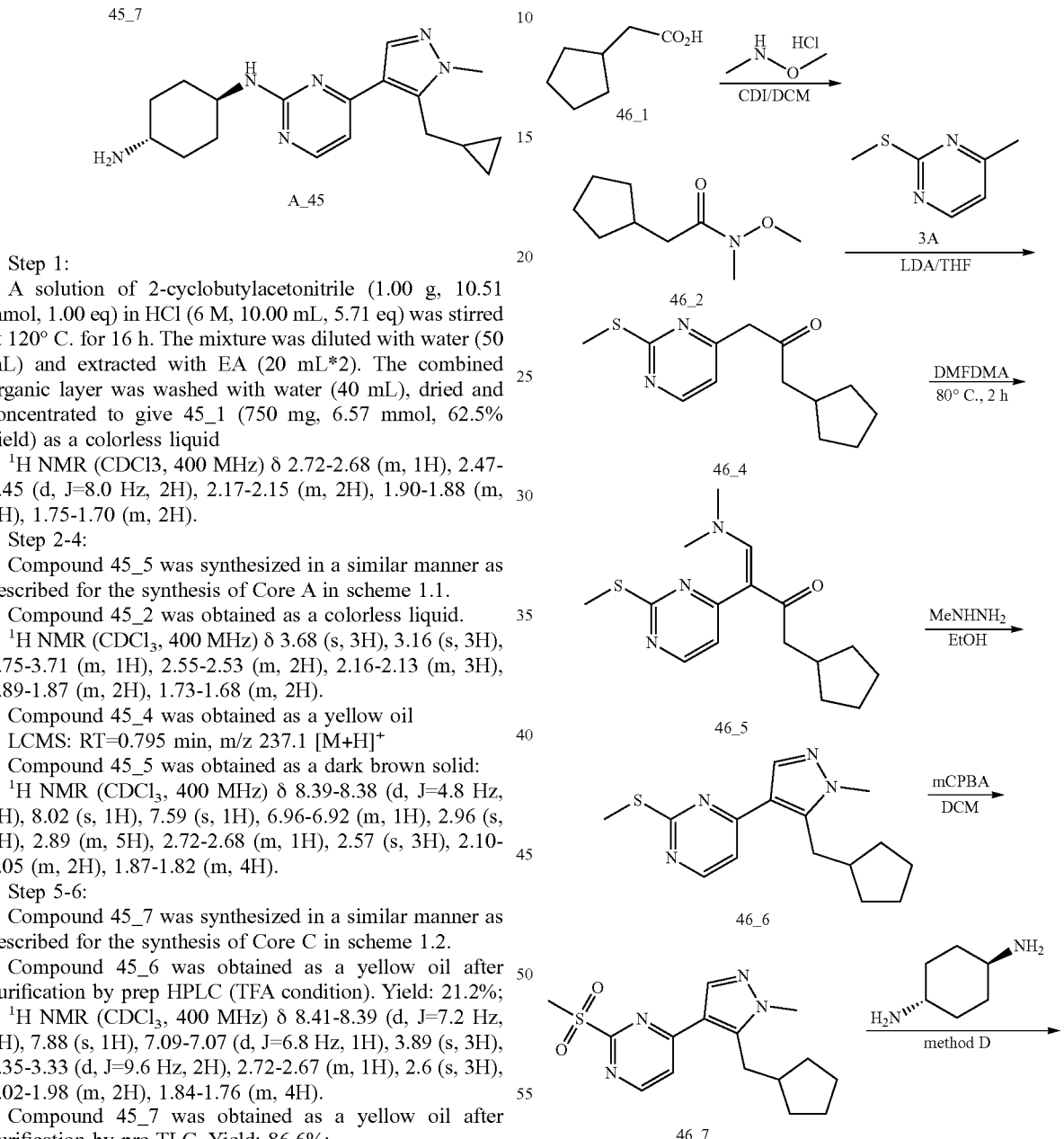

Compound A-46 was synthesized in a manner similar as described for the synthesis of compound A-45.

Compound 46_2 was obtained as a colorless oil.

¹H NMR (CDCl₃, 400 MHz) δ 3.64 (s, 3H), 3.14 (s, 3H), 2.41-2.40 (t, J=7.2 Hz, 2H), 2.26-2.25 (m, 1H), 1.82-1.80 (m, 2H), 1.59-1.51 (m, 4H), 1.15-1.13 (m, 2H).

Compound 46_5 was obtained as a yellow oil.

LCMS: RT=1.294 min, m/z 306.2 [M+H]⁺

Compound 46_6 was obtained as a yellow oil after purification by prep TLC. Yield: 26.5%

LCMS: RT=0.866 min, m/z 289.1 [M+H]⁺

¹H NMR (CDCl₃, 400 MHz) δ 8.42-8.41 (d, J=5.2 Hz, 1H), 7.90 (s, 1H), 7.10-7.09 (d, J=5.2 Hz, 1H), 3.90 (s, 3H), 3.26-3.24 (d, J=7.6 Hz, 2H), 2.61-2.60 (d, J=4.8 Hz, 3H), 2.21 (m, 1H), 1.72-1.67 (m, 4H), 1.27-1.26 (m, 2H), 1.25 (m, 3H).

Compound 46_7 was obtained as a white solid after purification by prep TLC. Yield: 44.0%

LCMS: RT=1.219 min, m/z 321.2 [M+H]⁺

Compound A-46 was obtained as a yellow solid after purification by prep HPLC (basic condition). Yield: 52.7%

LCMS: RT=2.381 min, m/z 355.2 [M+H]⁺

¹H NMR (CD₃OD, 400 MHz) δ 8.16 (s, 1H), 8.07-8.03 (t, J=8.0 Hz, 1H), 7.20-7.18 (d, J=6.8 Hz, 1H), 4.06-4.02 (m, 1H), 3.88 (s, 3H), 3.31-3.30 (m, 2H), 3.16 (s, 1H), 2.17-2.15 (m, 5H), 1.67 (m, 4H), 1.56 (m, 6H), 1.30-1.25 (m, 2H)

Preparation of (1R, 4R)—N¹-(5-chloro-4-(5-(cyclopropylmethyl)-1-methyl-1H-pyrazol-4-yl)pyrimidin-2-yl)cyclohexane-1,4-diamine (A-51)

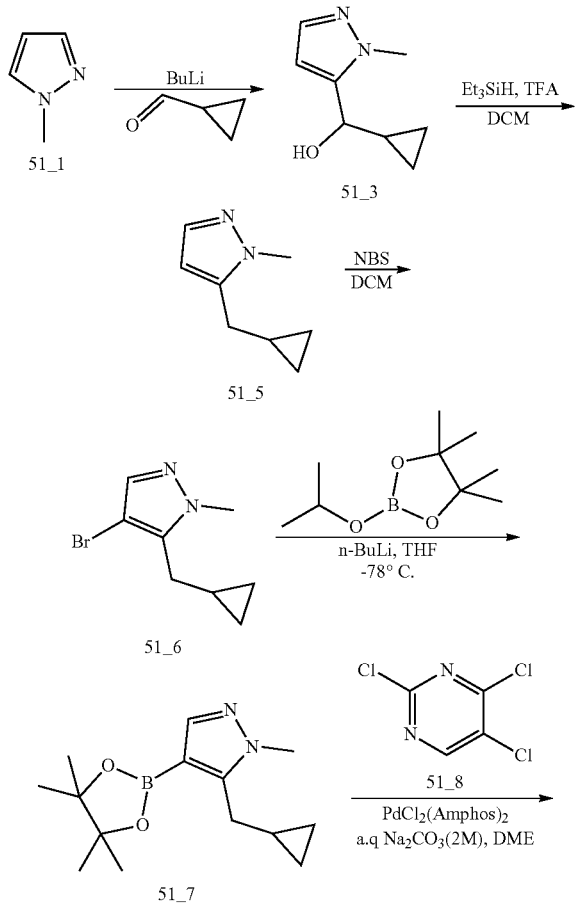

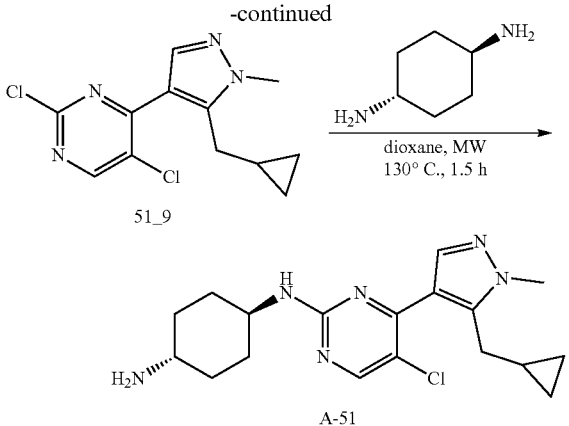

Step 1:

To a solution of compound N-methylpyrazole (51_1, 8.00 g, 97.44 mmol, 1.00 eq) in THF (160 mL) was added drop-wise n-BuLi (2.5 M, 46.77 mL, 1.20 eq) at −78° C. After the resulting mixture was stirred for 1 h at that temperature, the solution of cyclopropanecarbaldehyde (8.20 g, 116.93 mmol, 1.20 eq) in THF (80 mL) was added drop-wise. And then the reaction mixture was stirred at 20° C. for 16 h. TLC (PE:EA=2:1) showed reactant 1 (Rf=0.3) was consumed and product (Rf=0.05) was formed.

The mixture was poured into aqueous NH₄Cl (300 mL) and stirred for 10 min. The aqueous phase was extracted with ethyl acetate (100 mL*2). The combined organic phase was washed with brine (100 mL), dried over anhydrous Na₂SO₄, filtered and concentrated in vacuum. The residue was purified by column chromatography (SiO₂, PE:EA=8:1-0:1) to afford compound 51_3 (12.00 g, 78.85 mmol, 80.9% yield, 100% purity) as a colorless oil.

LCMS: RT=0.118 min, m/z 153.1 [M+H]⁺

Step 2:

The reaction mixture of compound 51_3 (9.00 g, 59.14 mmol, 1.00 eq), TFA (40.46 g, 354.84 mmol, 26.27 mL, 6.00 eq) and Et₃SiH (41.26 g, 354.84 mmol, 56.52 mL, 6.00 eq) in DCM (900 mL) was stirred at 40° C. for 36 h. The mixture was adjusted to pH=8 with aqueous NaHCO₃ and separated. The organic layer was concentrated and purified by prep HPLC (basic condition) to give compound 51_5 (2.10 g, 15.42 mmol, 26.1% yield) as a dark brown oil.

LCMS: RT=0.565 min, m/z 137.1 [M+H]⁺

Step 3:

To a solution of compound 51_5 (2.10 g, 15.42 mmol, 1.00 eq) in DCM (21 mL) was added NBS (3.02 g, 16.96 mmol, 1.10 eq) at 0° C. The mixture was stirred at 20° C. for 2 h. The mixture was concentrated and purified by column chromatography (SiO₂, PE:EA=20:1) to give compound 51_6 (3.00 g, 13.95 mmol, 90.5% yield) as a yellow oil.

LCMS: RT=0.784 min, m/z 217.1 [M+H]⁺

¹H NMR (CDCl3, 400 MHz) δ 7.39 (s, 1H), 3.87 (s, 3H), 2.65-2.63 (d, J=8.8 Hz, 2H), 0.98-0.94 (m, 1H), 0.55-0.51 (m, 2H), 0.29-0.25 (m, 2H).

Step 4:

To a solution of compound 51_6 (3.00 g, 13.95 mmol, 1.00 eq) in THF (60 mL) was added n-BuLi (2 M, 10.46 mL, 1.50 eq) drop-wise at −78° C. After stirring for 0.5 h at that temperature, a solution of 2-isopropoxy-4,4,5,5-tetramethyl-1,3,2-dioxaborolane (5.19 g, 27.90 mmol, 2.00 eq) in THF (6 mL) was added. The resulting mixture was warmed to 20° C. and stirred for 0.5 h. TLC (PE:EA=5:1) showed reactant (Rf=0.6) was consumed and product (Rf=0.5) was formed.

The mixture was quenched with saturated NH₄Cl (50 mL) and extracted with EA (100 mL). The organic layer was concentrated and purified by column chromatography (SiO₂, PE:EA=20:1-10:1) to give compound 51_7 (3.30 g, 11.40 mmol, 81.7% yield, 90.5% purity) as a colorless oil.

LCMS: RT=0.801 min, m/z 263.2 [M+H]⁺

¹H NMR (CDCl3, 400 MHz) δ 7.67 (s, 1H), 3.85 (s, 3H), 2.82-2.81 (d, J=6.8 Hz, 2H), 1.30 (s, 12H), 0.92-0.90 (m, 1H), 0.45-0.42 (m, 2H), 0.29-0.27 (m, 2H).

Step 5:

To a solution of compound 51_7 (500.00 mg, 1.91 mmol, 1.00 eq) in DME (10 mL) were added 2, 4, 5-trichloropyrimidine (51_8, 420.40 mg, 2.29 mmol, 1.20 eq), Na₂CO₃ (2 M, 2.10 mL, 2.20 eq) and catalyst PdCl₂(Amphos)₂ (67.62 mg, 95.50 µmol, 0.05 eq) under nitrogen. The resulting mixture was stirred at 85° C. for 2 hr under nitrogen. TLC (PE:EA=5:1) showed reactant (Rf=0.4) was consumed and product (Rf=0.5) was formed. The mixture was diluted with water (50 mL) and extracted with EA (50 ml). The organic layer was concentrated and purified by silica gel column (PE:EA=5:1) to afford compound 51_9 (350.0 mg, 1.05 mmol, 55% yield, 85% purity) as a yellow oil.

LCMS: RT=0.819 min, m/z 283.1 [M+H]⁺

Step 6:

The reaction mixture of compound 51_9 (300.00 mg, 1.06 mmol, 1.00 eq) and trans-cyclohexane-1, 4-diamine (484.17 mg, 4.24 mmol, 4.00 eq) in dioxane (4.5 mL) was stirred at 130° C. for 2 h under microwave. The mixture was filtered and concentrated. The crude was purified by prep-HPLC (HCl condition) to give A-51 (80.00 mg, 200.04 µmol, 18.9% yield, 99.3% purity, HCl) as a yellow solid.

LCMS: RT=2.817 min, m/z 361.1 [M+H]⁺

¹H NMR (DMSO-d₆, 400 MHz) δ 8.37 (s, 1H), 8.29 (s, 3H), 8.08 (s, 1H), 3.86 (s, 3H), 3.70-3.68 (m, 2H), 3.06-3.05 (d, J=6.4 Hz, 2H), 2.96 (s, 1H), 2.03-1.95 (m, 4H), 1.49-1.32 (m, 4H), 0.98 (s, 1H), 0.42-0.40 (m, 2H), 0.16 (m, 2H).

Preparation of (1R, 4R)—N¹-(4-(5-(cyclopropylmethyl)-1-methyl-1H-pyrazol-4-yl)-5-methylpyrimidin-2-yl)cyclohexane-1,4-diamine (A-52)

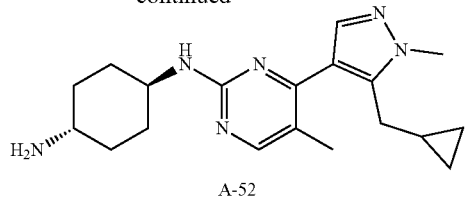

A-52

Step 1:

To a solution of compound 51_7 (500.00 mg, 1.91 mmol, 1.00 eq) in DME (10 mL) were added compound 52_8 (373.60 mg, 2.29 mmol, 1.20 eq), Na₂CO₃ (a.q) (2 M, 2.1 mL, 2.20 eq) and catalyst PdCl₂(Amphos)₂ (67.62 mg, 95.50 µmol, 0.05 eq) under nitrogen. The resulting mixture was stirred at 85° C. for 2 h under nitrogen. TLC (PE:EA=5:1) showed reactant (Rf=0.4) was consumed and product (Rf=0.25) was formed. The mixture was diluted with water (50 mL) and extracted with EA (50 mL). The organic layer was concentrated and purified by column chromatography (SiO₂, PE:EA=20:1-5:1) to give compound 52_9 (350.00 mg, 1.15 mmol, 60.3% yield, 86.5% purity) as a yellow oil.

LCMS: RT=0.761 min, m/z 263.2 [M+H]⁺

Step 2:

The reaction mixture of compound 52_9 (350.00 mg, 1.33 mmol, 1.00 eq) and trans-cyclohexane-1, 4-diamine (607.49 mg, 5.32 mmol, 4.00 eq) in dioxane (5 mL) was stirred at 130° C. for 2 h under microwave. TLC (PE:EA=1:1) showed reactant (Rf=0.6) was consumed and product (Rf=0.05) was formed. The mixture was filtered and concentrated. The crude was purified by prep-HPLC (HCl condition) and then prep-HPLC (basic condition) to give A-52 (30.0 mg, 88.00 µmol, 6.6% yield, 99.8% purity) as a yellow solid.

LCMS: RT=2.429 min, m/z 341.2 [M+H]⁺

¹H NMR (CDCl3, 400 MHz) 8.09 (s, 1H), 7.67 (s, 1H), 4.72-4.70 (d, J=8.4 Hz, 1H), 3.91 (s, 3H), 3.82-3.80 (m, 1H), 3.02-3.00 (d, J=6.4 Hz, 2H), 2.79-2.76 (m, 1H), 2.22 (s, 3H), 2.14-1.93 (m, 4H), 1.32-1.23 (m, 4H), 0.97 (m, 1H), 0.45-0.42 (m, 2H), 0.12-0.10 (m, 2H).

Preparation of (1R,4R)—N¹-(5-chloro-4-(5-(cyclopropylmethyl)-1-methyl-1H-pyrazol-4-yl) pyrimidin-2-yl)-4-methylcyclohexane-1,4-diamine (A-30_1) and (1S,4S)—N1-(5-chloro-4-(5-(cyclopropylmethyl)-1-methyl-1H-pyrazol-4-yl)pyrimidin-2-yl)-4-methylcyclohexane-1,4-diamine (A-30_2)

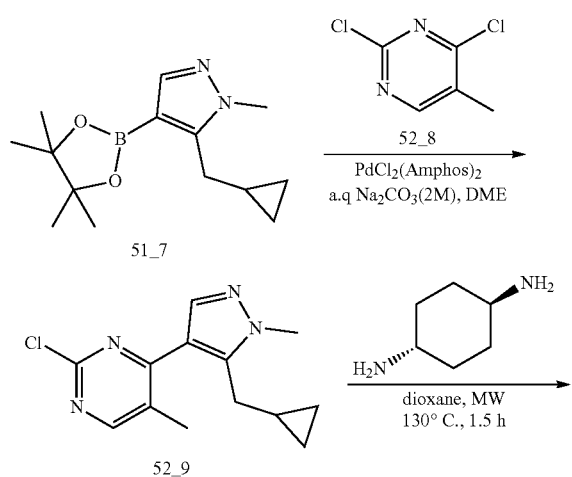

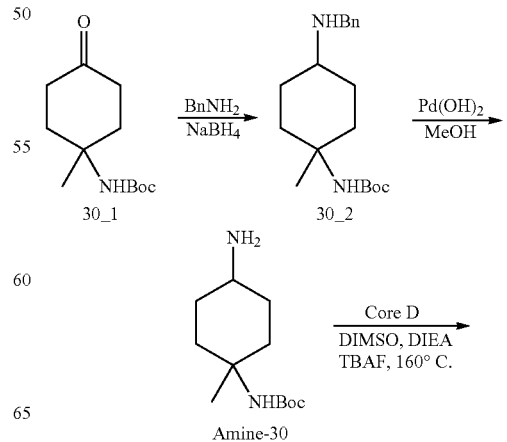

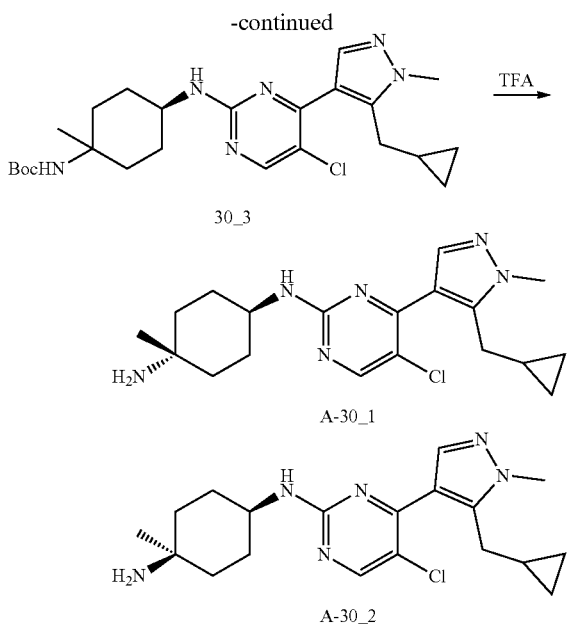

Step 1:

To a mixture of compound 30_1 (900.00 mg, 3.96 mmol, 1.00 eq) and BnNH₂ (424.26 mg, 3.96 mmol, 432.92 μL, 1.00 eq) in DCM (18.00 mL) were added AcOH (237.77 mg, 3.96 mmol, 226.45 μL, 1.00 eq) and NaBH(OAc)₃ (1.68 g, 7.92 mmol, 2.00 eq). The resulting mixture was stirred at 20° C. for 2 hours. The mixture was quenched with H₂O (50 mL) and separated. The organic layer was concentrated. The residue was purified by column chromatography on Al₂O₃ (DCM:MeOH=20:1) to give compound 30_2 (650.00 mg, 2.03 mmol, 51.3% yield, 99.6% purity) as a red oil.

LCMS: RT=1.520 min, m/z 319.2 [M+H]⁺

¹H NMR (CDCl3, 400 MHz) δ 7.33-7.31 (m, 5H), 4.43-4.35 (m, 1H), 3.81 (d, J=10.8 Hz, 2H), 2.62-2.50 (m, 1H), 2.12-2.09 (m, 1H), 1.82-1.79 (m, 4H), 1.43 (s, 9H), 1.38-1.27 (m, 7H).

Step 2:

To a solution of compound 30_2 (350.00 mg, 1.10 mmol, 1.00 eq) in MeOH (3.5 mL) was added Pd(OH)₂ (35.00 mg). The mixture was stirred at 20° C. for 16 hours under H₂ (16 psi). TLC (DCM:MeOH=10:1) showed reactant (Rf=0.6) consumed and product (Rf=0.3) formed. The mixture was filtered and the mother liquid was concentrated to give amine-30 (220.00 mg, 963.5 umol, 87.6% yield) as a red oil.

MS: m/z 229.2 [M+H]⁺

¹H NMR (CDCl3, 400 MHz) δ 4.43-4.33 (m, 1H), 3.82-2.66 (m, 1H), 2.08 (s, 1H), 1.79-1.66 (m, 4H), 1.43 (s, 9H), 1.33-1.27 (m, 7H).

Step 3:

To a solution of Amine-30 (300.00 mg, 917.99 μmol, 1.00 eq) and Core D (230.57 mg, 1.01 mmol, 1.10 eq) in DMSO (4 mL) were added DIEA (480.97 μL, 2.75 mmol, 3.00 eq) and TBAF (48.00 mg, 2.75 mmol, 0.20 eq). The mixture was stirred at 160° C. for 3 hours. The mixture was separated between EA (50 mL) and H₂O (50 mL). The organic layer was concentrated to give 30_3 (400.00 mg, crude) as a red oil.

LCMS: RT=1.081 min, m/z 475.2 [M+H]⁺

Step 4:

To a solution of 30_3 (400.00 mg, 842.05 μmol, 1.00 eq) in DCM (4 mL) was added TFA (800 μL) at 0° C. The resulting mixture was stirred at 20° C. for 1 hour. TLC (PE:EA=2:1) showed reactant (Rf=0.6) consumed and product (Rf=0.05) formed. The mixture was concentrated. The residue was purified by prep-HPLC (HCl condition) to give A-30_1 (55.00 mg, 127.60 μmol, 15.1% yield, 95.4% purity, HCl) and A-30_2 (40.00 mg, 95.31 μmol, 11.3% yield, 98.0% purity, HCl) as yellow solid.

LCMS(A-30_1): RT=2.495 min, m/z 375.2 [M+H]⁺

¹H NMR_Peak-1 (MeOD, 400 MHz) δ 8.49 (s, 1H), 8.45 (s, 1H), 4.10 (s, 1H), 3.96 (s, 3H), 3.23 (d, J=6.4 Hz, 2H), 2.11-2.10 (m, 2H), 2.07-1.94 (m, 2H), 1.84-1.74 (m, 4H), 1.47 (s, 3H), 1.09-1.08 (m, 1H), 0.55-0.51 (m, 2H), 0.28-0.27 (m, 2H).

LCMS(A-30_2): RT=2.527 min, m/z 375.2 [M+H]⁺

¹H NMR_Peak-2 (MeOD, 400 MHz) δ 8.47 (s, 2H), 4.19 (s, 1H), 3.96 (s, 3H), 3.19 (d, J=6.4 Hz, 2H), 2.05-2.1.99 (m, 2H), 1.87-1.78 (m, 2H), 1.42 (s, H), 1.08-1.07 (m, 1H), 0.54-0.52 (m, 2H), 0.30-0.28 (m, 2H).

Preparation of (1R,4R)—N¹-(4-(5-(cyclobutylmethyl)-1-isopropyl-1H-pyrazol-4-yl)pyrimidin-2-yl)cyclohexane-1,4-diamine (A53)

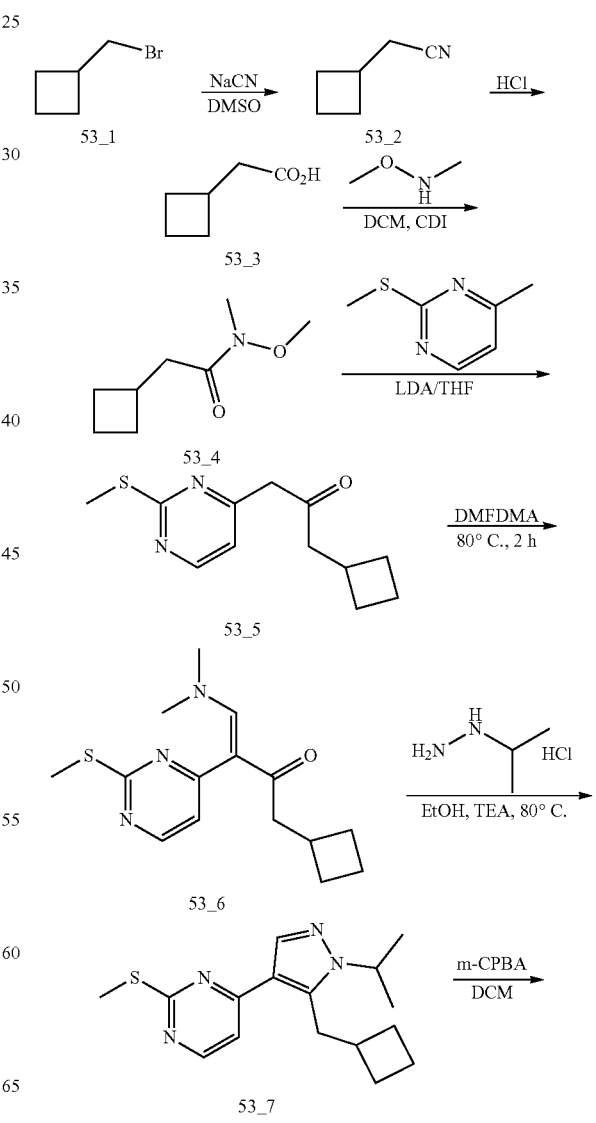

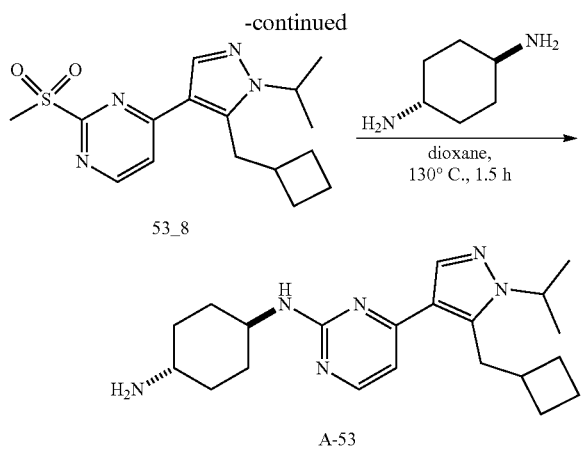

Step 1:

To a mixture of NaCN (13.81 g, 281.82 mmol, 1.40 eq) in DMSO (240 mL) was added 53_1 (30.00 g, 201.30 mmol, 22.56 mL, 1.00 eq) dropwise at 60° C. The mixture was kept at 75° C. for 16 hr. The mixture was cool down and diluted with water (500 mL). The solution was extracted with EtOAc (200 mL*3). The combined organic layers were washed with brine (100 mL*3) and dried. The organic layer was concentrated to give 53_2 (15.00 g, 157.66 mmol, 78.3% yield) as a light yellow liquid.

$^1$H NMR (CDCl3, 400 MHz) δ 2.64-2.63 (m, 1H), 2.42-2.41 (d, J=6.4 Hz, 2H), 2.20-2.17 (m, 2H), 1.90-1.83 (m, 4H).

Step 2:

A solution of 53_2 (15.00 g, 157.66 mmol, 1.00 eq) in HCl (6 M, 150 mL, 5.71 eq) was stirred at 120° C. for 16 hours. The mixture was diluted with water (500 mL) and extracted with EtOAc (200 mL*2). The combined organic layers were washed with water (400 mL). The organic layer was dried and concentrated to give 53_3 (16.00 g, 140.18 mmol, 88.9% yield) as a colorless liquid.

$^1$H NMR (CDCl3, 400 MHz) δ 2.69-2.68 (m, 1H), 2.47-2.45 (m, 2H), 2.17-2.15 (m, 2H), 1.89-1.87 (m, 2H), 1.75-1.70 (m, 2H).

Step 3:

To a solution of 53_3 (16.00 g, 140.18 mmol, 1.00 eq) and N-methoxymethanamine (20.51 g, 210.27 mmol, 1.50 eq, HCl) in DCM (160 mL) was added CDI (45.46 g, 280.36 mmol, 2.00 eq) at 0° C. in portions. The mixture was stirred at 20° C. for 16 hours. The mixture was diluted with water (50 mL) and extracted with DCM (30 mL*3). The combined organic layer was dried and concentrated to give crude product. The crude product was purified by silica gel column (PE:EA=50:1-10:1) to give 53_4 (12.00 g, 76.33 mmol, 54.4% yield) as a colorless liquid.

$^1$H NMR (CDCl3, 400 MHz) δ 3.68-3.67 (d, J=2.4 Hz, 3H), 3.16 (s, 3H), 2.77-2.73 (m, 1H), 2.54-2.53 (m, 2H), 2.16-2.13 (m, 2H), 1.88-1.86 (m, 2H), 1.73-1.72 (m, 2H), 1.70-1.68 (m, 2H).

Step 4:

To a solution of 53_4 (4.50 g, 32.09 mmol, 1.00 eq) in THF (225 mL) was added LDA (2 M, 24.07 mL, 1.50 eq) at −78° C. After stirred for 1 hr, a solution of 2-cyclobutyl-N-methoxy-N-methyl-acetamide (6.05 g, 38.51 mmol, 1.20 eq) in THF (120 mL) was added into it at −78° C. The resulting mixture was stirred at −78° C. for 4 hr, quenched with saturated NH4Cl (200 mL), and the aqueous phase was extracted with ethyl acetate (200 mL*3). The combined layers were washed with brine (200 mL), dried over anhydrous Na2SO4, filtered and concentrated to give 53_5 (10.00 g, crude) as a yellow oil.

LCMS: RT=0.788 min, m/z 237.1 [M+H]$^+$

Step 5:

The solution of 53_5 (10.00 g, 42.31 mmol, 1.00 eq) in DMF-DMA (201.68 g, 1.69 mol, 224.09 mL, 40.00 eq) was stirred at 90° C. for 2 hr. The mixture was concentrated to give crude product. The crude product was purified by silica gel column (DCM:MeOH=1:0-10:1) to give 53_6 (8.80 g, crude) as a black brown solid.

Step 6:

To a solution of 53_6 (800.00 mg, 2.75 mmol, 1.00 eq) in EtOH (12 mL) was added isopropylhydrazine (364.95 mg, 3.30 mmol, 1.20 eq, HCl) and TEA (333.93 mg, 3.30 mmol, 457.43 uL, 1.20 eq). The mixture was stirred at 90° C. for 1 hr. The mixture was concentrated. The crude was purified by pre-HPLC (TFA) to give 53_7 (600.00 mg, 1.88 mmol, 68.5% yield, 95% purity) as a yellow oil.

LCMS: RT=0.901 min, m/z 303.2 [M+H]$^+$

Step 7:

To a solution of 53_7 (600.00 mg, 1.98 mmol, 1.00 eq) in DCM (9 mL) was added m-CPBA (1.01 g, 4.96 mmol, 85% purity, 2.50 eq) at 0° C. The mixture was stirred at 20° C. for 3 hr. The reaction was quenched with saturated a.q NaS2O3 (50 mL) and extracted with DCM (20 mL*2). The combined organic layers were washed with a.q NaHCO3 (40 mL). The organic layer was dried and concentrated. The crude was purified by prep-TLC (DCM:MeOH=10:1)(Rf=0.6) to give 53_8 (500.00 mg, 1.50 mmol, 75.5% yield) as a yellow oil.

LCMS: RT=0.803 min, m/z 335.1 [M+H]$^+$

Step 8:

To a solution of 53_8 (500.00 mg, 1.50 mmol, 1.00 eq) in dioxane (7.5 mL) was added trans-cyclohexane-1,4-diamine (685.14 mg, 6.00 mmol, 4.00 eq). The mixture was stirred at 130° C. for 2 hr in the microwave. The mixture was filtered and concentrated. The crude was purified by prep HPLC (base) and prep HPLC(HCl) to give A-53 (250.00 mg, 615.9 μmol, 41% yield, 99.8% purity, HCl) as a yellow solid.

LCMS: RT=2.57 min, m/z 369.2 [M+H]$^+$ $^1$H NMR (DMSO, 400 MHz) δ 8.88-8.87 (m, 1H), 8.38-8.25 (m, 5H), 7.30-7.28 (m, 1H), 4.78-4.76 (m, 1H), 3.36-3.34 (m, 2H), 3.05 (s, 1H), 2.61 (s, 1H), 2.05 (m, 4H), 1.92-1.91 (m, 2H), 1.78 (m, 4H), 1.47-1.39 (m, 10H).

Preparation of (1R,4R)—N$^1$-(4-(1-methyl-5-((1-methylcyclopropyl)methyl)-1H-pyrazol-4-yl)pyrimidin-2-yl)cyclohexane-1,4-diamine (A56)

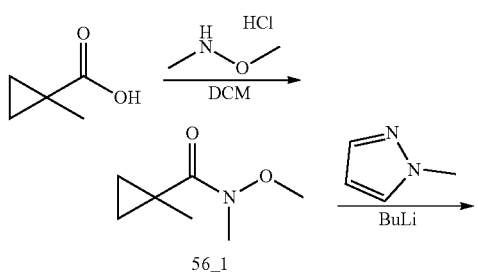

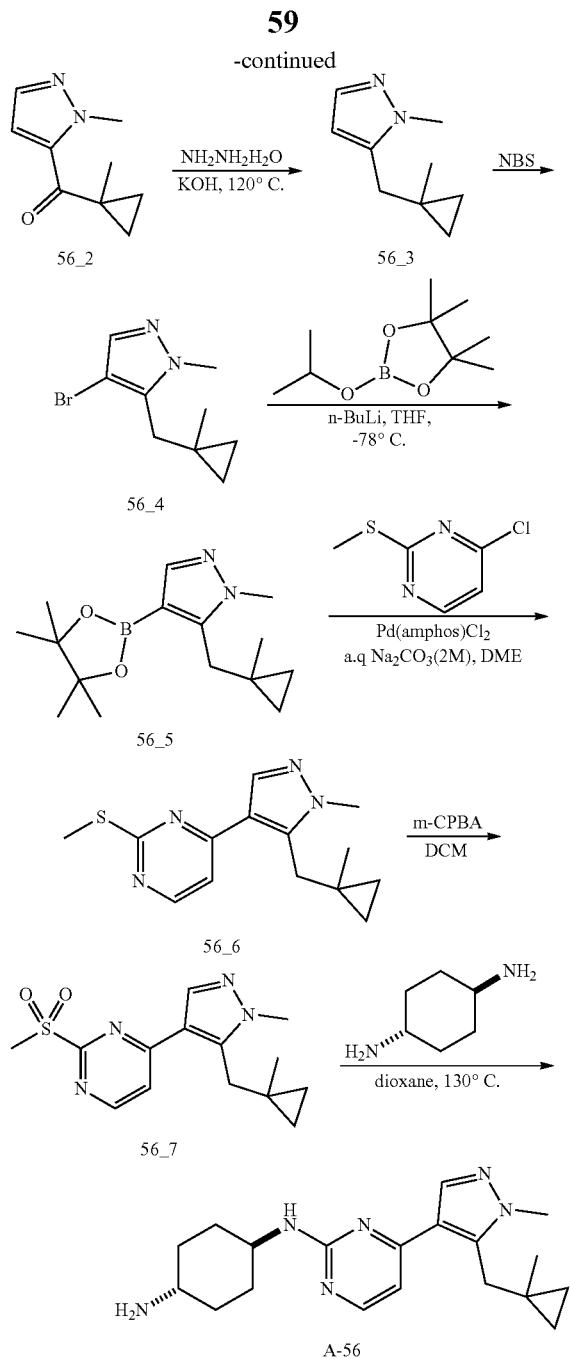

Step 1:

To a solution of 1-methylcyclopropane-1-carboxylic acid (4.00 g, 39.95 mmol, 1.00 eq) and CDI (7.13 g, 43.95 mmol, 1.10 eq) in DCM (40 mL) was added N-methoxymethanamine (4.68 g, 47.94 mmol, 1.20 eq, HCl) at 0° C. in portions. The mixture was stirred at 20° C. for 16 hr. The mixture was diluted with water (50 mL) and extracted with DCM (20 mL*3). The combined organic layers were dried and concentrated to give crude product. The crude product was purified by silica gel column (PE:EA=30:1-10:1) to give 56_1 (3.30 g, 23.05 mmol, 57.7% yield) as a colorless liquid.

$^1$H NMR (CDCl3, 400 MHz) δ 3.73 (s, 3H), 3.23 (s, 3H), 1.37 (s, 3H), 1.05-1.03 (m, 2H), 0.58-0.55 (m, 2H).

Step 2:

To a solution of 1-methylpyrazole (1.70 g, 20.71 mmol, 1.72 mL, 1.00 eq) in THF (35.00 mL) was added n-BuLi (2.5 M, 9.94 mL, 1.20 eq) at −78° C. Stirred for 1 hr. Compound 56_1 (3.26 g, 22.78 mmol, 1.10 eq) in THF (35 mL) was added to it at −78° C. The resulting mixture was stirred at 20° C. for 1 hr. The mixture was quenched with saturated NH4Cl (20 mL) and extracted with EtOAc (20 mL*2). The organic layer was concentrated and purified by silica gel column (PE:EA=1:0-20:1) to give 56_2 (2.50 g, 13.41 mmol, 64.8% yield, 88.1% purity) as a yellow oil.

LCMS: RT=0.609 min, m/z 165.1 [M+H]$^+$

Step 3:

The reaction mixture of 56_2 (2.00 g, 12.18 mmol, 1.00 eq) and KOH (2.73 g, 48.72 mmol, 4.00 eq) in NH2NH2.H2O (2.57 g, 48.72 mmol, 2.49 mL, 95% purity, 4.00 eq) and diglycol (40 mL) was heated to 110° C. for 1.5 hr, then at 200° C. for another 1 hour with Dean-Stark. The mixture was diluted with water (50 mL) and extracted with MTBE (50 mL*2). The combined organic layers were concentrated to give 56_3 (1.10 g, crude) as a colorless oil.

LCMS: RT=0.639 min, m/z 151.1 [M+H]$^+$

Step 4:

To a solution of 56_3 (1.10 g, 7.32 mmol, 1.00 eq) in DCM (11 mL) was added NBS (1.30 g, 7.32 mmol, 1.00 eq) at 0° C. The mixture was stirred at 20° C. for 1 hr. The mixture was concentrated. The crude was purified by silica gel column (PE:EA=1:0-50:1) to give 56_4 (1.45 g, 5.65 mmol, 77.1% yield, 89.2% purity) as a colorless oil.

LCMS: RT=0.835 min, m/z 229.0 [M+H]$^+$ $^1$H NMR (CDCl3, 400 MHz) δ 7.39 (s, 1H), 3.85 (s, 3H), 2.73 (s, 2H), 1.05 (s, 3H), 0.44-0.31 (m, 4H).

Step 5:

To a solution of 56_4 (1.45 g, 6.33 mmol, 1.00 eq) in THF (29 mL) was added n-BuLi (2 M, 4.75 mL, 1.50 eq) at −78° C. After 30 min, 2-isopropoxy-4,4,5,5-tetramethyl-1,3,2-dioxaborolane (2.36 g, 12.66 mmol, 2.59 mL, 2.00 eq) in THF (2.5 mL) was added to it. The resulting mixture was warmed to 20° C. and stirred for 0.5 hr. The mixture was quenched with saturated NH4Cl (50 mL) and extracted with EtOAc (100 mL). The organic layer was concentrated and purified by silica gel column (PE:EA=20:1-10:1) to give 56_5 (1.25 g, 4.11 mmol, 64.9% yield, 90.7% purity) as a colorless oil.

LCMS: RT=0.928 min, m/z 277.1 [M+H]$^+$

Step 6:

To a solution of 56_5 (500.00 mg, 1.81 mmol, 1.00 eq) in DME (10 mL) was added 4-chloro-2-methylsulfanyl-pyrimidine (290.79 mg, 1.81 mmol, 210.72 μL, 1.00 eq), NA2CO3 (2 M, 1.99 mL, 2.20 eq) and 4-ditert-butylphosphanyl-N,N-dimethyl-aniline;dichloropalladium (64.09 mg, 90.50 μmol, 64.09 μL, 0.05 eq) under nitrogen. The resulting mixture was stirred at 85° C. for 2 hr under nitrogen. The mixture was diluted with water (50 mL) and extracted with EtOAc (50 mL). The organic layer was concentrated and purified by silica gel column (PE:EA=5:1) to give 56_6 (350.00 mg, 1.14 mmol, 63% yield, 89% purity) as a yellow oil.

LCMS: RT=0.829 min, m/z 275.1 [M+H]$^+$

Step 7:

To a solution of 56_6 (350.00 mg, 1.28 mmol, 1.00 eq) in DCM (5.5 mL) was added MCPBA (690.28 mg, 3.20 mmol, 80% purity, 2.50 eq) at 0° C. The mixture was stirred at 20° C. for 2 hr. The mixture was quenched with aqueous Na2S2O3 (100 mL) and extracted with DCM (50 mL*2). The combined organic layers were concentrated and purified by silica gel column (PE:EA=1:1) to give 56_7 (200.00 mg, 617.72 μmol, 48.6% yield, 94.6% purity) as a yellow solid.

LCMS: RT=0.653 min, m/z 307.1 [M+H]⁺

Step 8:

The mixture of 56_7 (200.00 mg, 652.78 μmol, 1.00 eq) and trans-cyclohexane-1,4-diamine (298.17 mg, 2.61 mmol, 4.00 eq) in dioxane (3 mL) was stirred at 130° C. for 2 hr in the microwave. The mixture was filtered and concentrated. The crude was purified by prep-HPLC (base) to give A-56 (50.00 mg, 144.85 μmol, 22.2% yield, 98.6% purity) as a yellow solid.

LCMS: RT=1.999 min, m/z 341.2 [M+H]⁺

¹H NMR (CDCl3, 400 MHz) δ 8.18-8.17 (d, J=5.2 Hz, 1H), 7.82 (s, 1H), 6.69-6.67 (d, J=5.2 Hz, 1H), 4.87-4.85 (d, J=5.6 Hz, 1H), 3.88 (s, 3H), 3.84 (s, 1H), 3.38 (s, 2H), 2.75-2.73 (m, 1H), 2.17-2.16 (m, 2H), 1.94-1.92 (m, 2H), 1.31-1.27 (m, 4H), 1.08 (s, 3H), 0.31-0.25 (m, 4H).

Preparation of (1R,4R)—N¹-(4-(1-methyl-5-neopentyl-1H-pyrazol-4-yl)pyrimidin-2-yl)cyclohexane-1,4-diamine (A57)

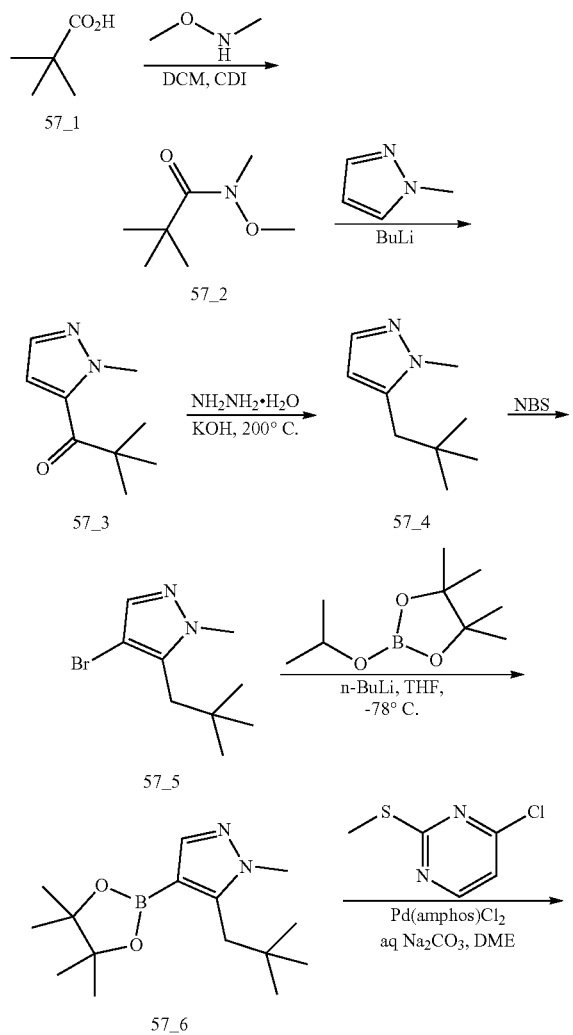

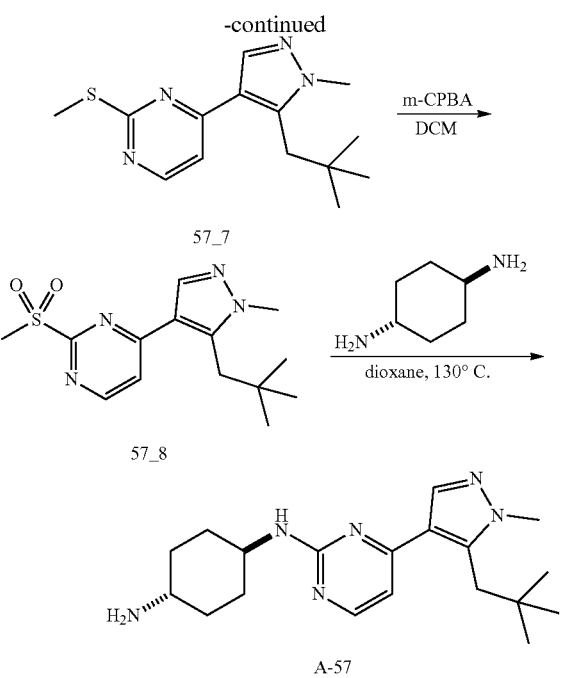

Compound A-57 was synthesized in a manner similar as described for the synthesis of compound A-56.

LCMS: RT=1.558 min, m/z 343.2 [M+H]⁺

¹H NMR (MeOD, 400 MHz) δ 8.20-8.13 (m, 2H), 7.29-7.27 (d, J=5.2 Hz, 1H), 4.12-4.09 (m, 1H), 3.92 (s, 3H), 3.34 (s, 1H), 3.21 (s, 1H), 2.20 (m, 4H), 1.63 (m, 4H), 0.98 (s, 9H).

Preparation of (4-(2-(((1R,4R)-4-aminocyclohexyl)amino)pyrimidin-4-yl)-1-methyl-1H-pyrazol-5-yl)(cyclopropyl)methanol (A58)

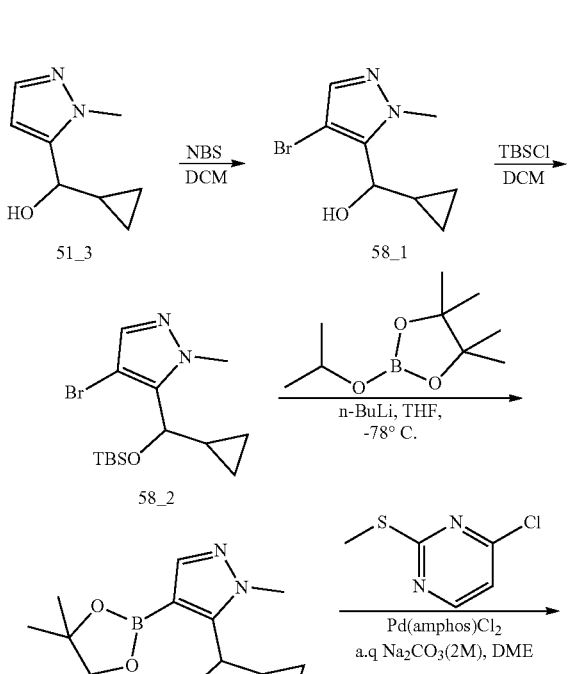

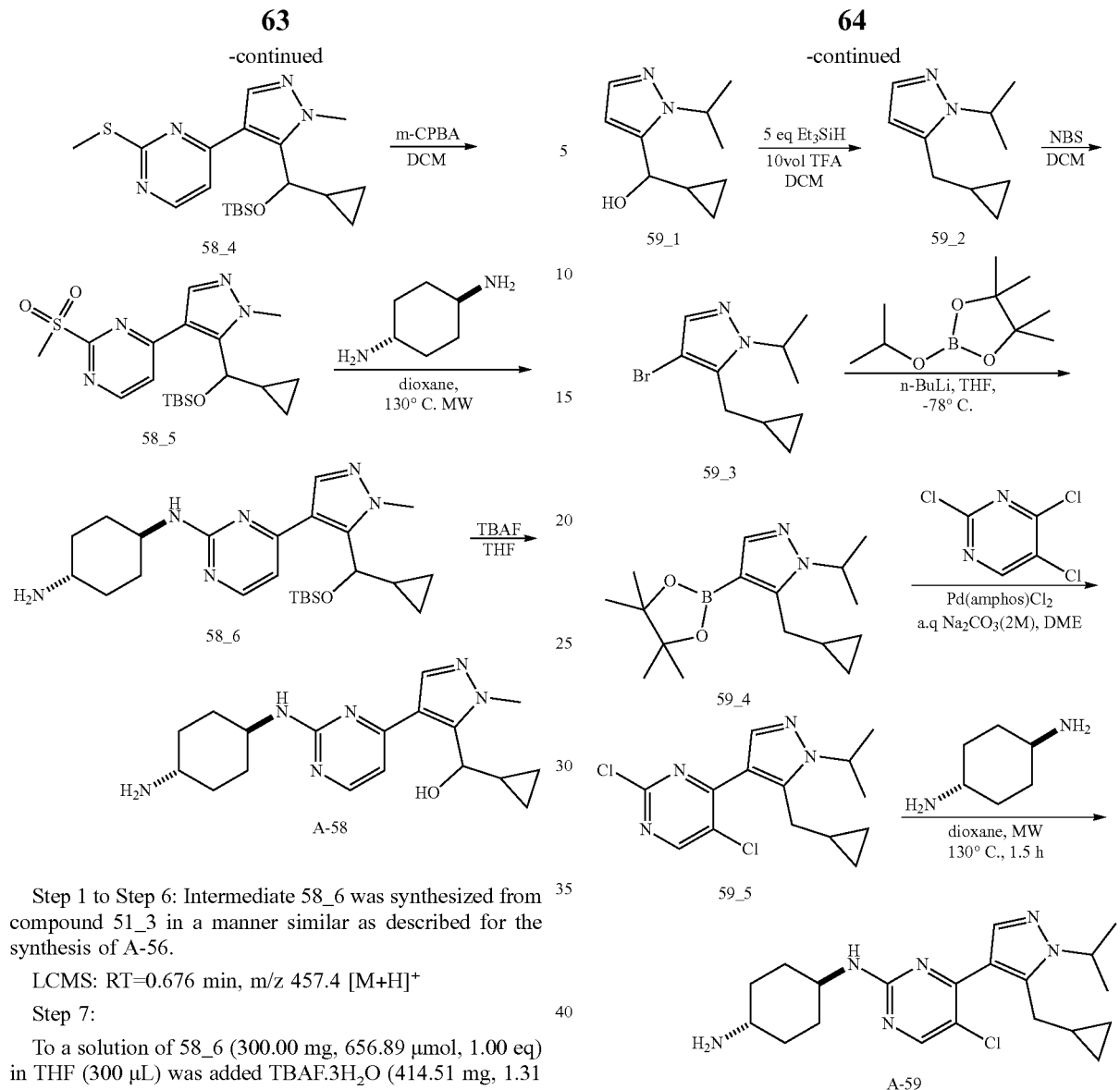

Step 1 to Step 6: Intermediate 58_6 was synthesized from compound 51_3 in a manner similar as described for the synthesis of A-56.

LCMS: RT=0.676 min, m/z 457.4 [M+H]$^+$

Step 7:

To a solution of 58_6 (300.00 mg, 656.89 μmol, 1.00 eq) in THF (300 μL) was added TBAF.3H$_2$O (414.51 mg, 1.31 mmol, 2.00 eq) at 20° C. The mixture was stirred for 30 min. The mixture was filtered and concentrated. The crude product was purified by prep-HPLC (base) to give A-58 (27.00 mg, 76.89 μmol, 11.7% yield, 97.5% purity) as a yellow solid.

LCMS: RT=2.29 min, m/z 343.2 [M+H]$^+$ $^1$H NMR (CDCl3, 400 MHz) δ 8.23-8.22 (d, J=5.2 Hz, 1H), 7.86 (s, 1H), 6.81-6.80 (d, J=5.2 Hz, 1H), 5.09 (s, 1H), 4.32-4.30 (m, 1H), 3.89 (s, 3H), 3.81-3.79 (m, 1H), 2.93-2.88 (m, 1H), 2.20-2.06 (m, 4H), 1.52-1.31 (m, 5H), 0.59-0.28 (m, 4H).

Preparation of (1R,4R)—N$^1$-(5-chloro-4-(5-(cyclopropylmethyl)-1-isopropyl-1H-pyrazol-4-yl)pyrimidin-2-yl)cyclohexane-1,4-diamine (A59)

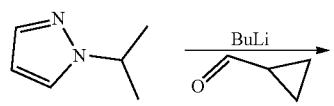

Compound A-59 was synthesized in a manner similar as described for the synthesis of compound A-51.

LCMS: RT=2.478 min, m/z 389.2 [M+H]$^+$ $^1$H NMR (MeOD, 400 MHz) δ 8.42-8.36 (m, 2H), 4.82-4.75 (m, 1H), 4.00 (s, 1H), 3.21-3.20 (s, 3H), 2.20-2.15 (m, 4H), 1.60-1.56 (m, 4H), 1.51 (s, 6H), 1.05 (s, 1H), 0.55-0.53 (m, 2H), 0.28 (m, 2H).

Preparation of (1R,4R)—N$^1$-(4-(5-(cyclopropylmethyl)-1-methyl-1H-pyrazol-4-yl)-5-(trifluoromethyl)pyrimidin-2-yl)cyclohexane-1,4-diamine (A60)

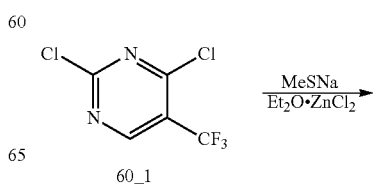

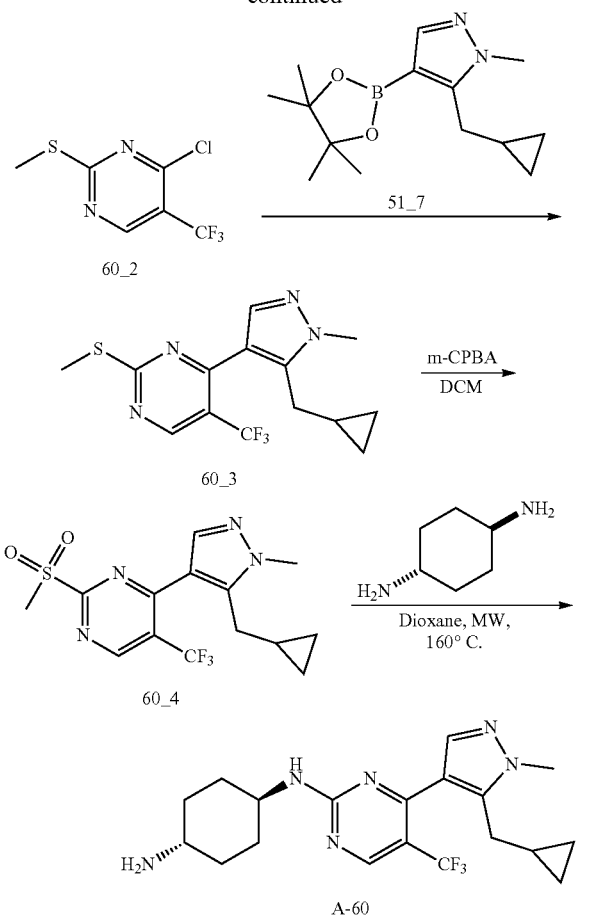

(300.00 mg, 611.96 umol, 27.9% yield, 66.9% purity) as a yellow solid.

LCMS: RT=0.927 min, m/z 329.0 [M+H]⁺

¹H NMR (CDCl3, 400 MHz) δ 8.75 (s, 1H), 7.75 (s, 1H), 3.94 (s, 3H), 2.95 (d, J=6.8 Hz, 2H), 2.57 (s, 3H), 0.98-0.94 (m, 1H), 0.48-0.44 (m, 2H), 0.17-0.13 (m, 2H).

Step 3:

To a solution of 60_3 (400.00 mg, 1.22 mmol, 1.00 eq) in DCM (7 mL) was added m-CPBA (657.92 mg, 3.05 mmol, 80% purity, 2.50 eq) at 0° C. The mixture was stirred at 20° C. for 1 hour. TLC (DCM:MeOH=20:1) showed reactant (Rf=0.6) consumed and product (Rf=0.5) formed. The mixture was quenched with a.q Na₂S2O3 (100 mL) and extracted with DCM (50 mL*2). The organic layer was concentrated and purified by silica gel column (PE:EA=1:1) to give 60_4 (300.00 mg, 738.23 umol, 60.5% yield, 88.7% purity) as a yellow solid.

LCMS: RT=0.72 min, m/z 361.0 [M+H]⁺

Step 4:

The mixture of 60_4 (200.00 mg, 555.02 μmol, 1.00 eq) and trans-cyclohexane-1, 4-diamine (253.51 mg, 2.22 mmol, 4.00 eq) in dioxane (3 mL) was stirred at 130° C. for 2 hours under microwave. The mixture was filtered and the filtrate was concentrated. The residue was purified by prep-HPLC (HCl condition) to give A-60 (80.00 mg, 185.66 μmol, 33.5% yield, 100% purity, HCl) as a yellow solid.

LCMS: RT=2.417 min, m/z 395.2 [M+H]⁺

¹H NMR (MeOH, 400 MHz) δ 8.66 (s, 1H), 7.90 (s, 1H), 4.15 (s, 1H), 3.97 (s, 3H), 3.20 (s, 1H), 3.10 (s, 2H), 2.18 (s, 4H), 1.62 (s, 4H), 1.05 (s, 1H), 0.53 (s, 2H), 0.25 (s, 2H).

Preparation of N-((1R,4R)-4-(1H-pyrazol-1-yl)cyclohexyl)-5-chloro-4-(5-(cyclopropylmethyl)-1-methyl-1H-pyrazol-4-yl)pyrimidin-2-amine (A64)

Step 1:

To a solution of 60_1 (2.00 g, 9.22 mmol, 1.00 eq) in THF (40 mL) was added ZnCl₂-Et₂O (1 M, 11.06 mL, 1.20 eq) at 0° C. under nitrogen protection. The mixture was stirred for 2 hours at 0° C. Methylsulfanylsodium (646.23 mg, 9.22 mmol, 587.48 μL, 1.00 eq) was added. The resulting mixture was stirred at 20° C. for 16 hours. TLC (pure PE) showed reactant 1 (Rf=0.5) consumed and product (Rf=0.3) formed. The mixture was quenched with 1M HCl (20 mL) and concentrated. The aqueous layer was extracted with DCM (20 mL*3). The combined organic layer was concentrated and purified by silica gel column (PE:EA=1:0-50:1) to give 60_2 (1.00 g, 1.97 mmol, 21.4% yield, 45.1% purity) as colorless oil.

LCMS: RT=0.794 min, m/z 228.9 [M+H]⁺

¹H NMR (CDCl3, 400 MHz) δ 8.67 (s, 1H), 2.62 (s, 3H).

Step 2:

To a solution of 51_7 (574.11 mg, 2.19 mmol, 1.00 eq) in THF (10 mL) were added 60_2 (500.00 mg, 2.19 mmol, 1.00 eq), K₃PO₄ (1 M, 4.38 mL, 2.00 eq) and Ad₂nBuP.Biphenyl (50.00 mg) under nitrogen. The resulting mixture was stirred at 85° C. for 2 hours under nitrogen. TLC (PE:EA=1:1) showed reactant (Rf=0.6) consumed and product (R=0.5) formed. The mixture was concentrated and diluted with H₂O (50 mL). The aqueous layer was extracted with EA (20 mL*2). The organic layer was concentrated. The residue was purified by silica gel column (PE:EA=20:1-5:1) to give 60_3

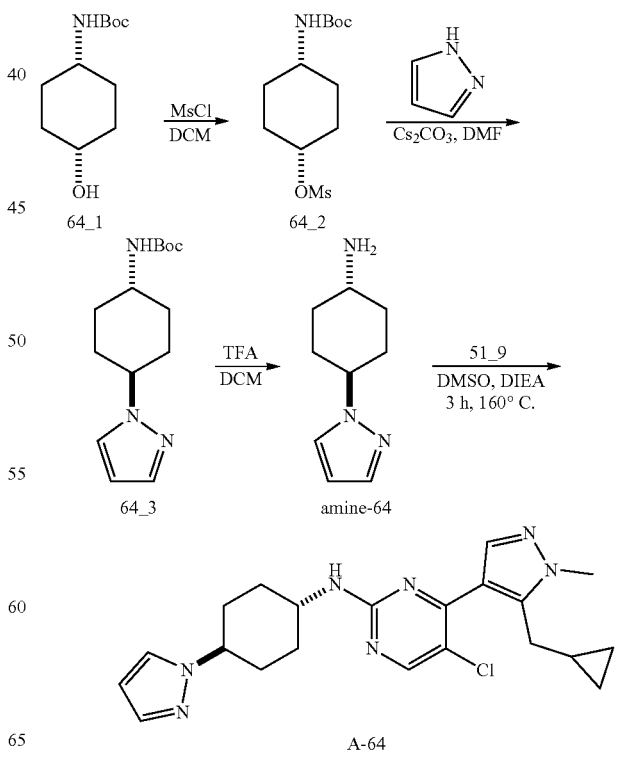

Step 1:

To a solution of 64_1 (2.00 g, 9.29 mmol, 1.00 eq) in DCM (20 mL) were added TEA (1.88 g, 18.58 mmol, 2.58 mL, 2.00 eq) and methanesulfonyl chloride (1.06 g, 9.29 mmol, 719.03 μL, 1.00 eq) at 0° C. The mixture was stirred at 20° C. for 2 hours. The mixture was diluted with H₂O (30 mL) and extracted with DCM (20 mL*2). The combined organic layers were dried and concentrated to give 64_2 (2.50 g, 8.52 mmol, 91.7% yield) as a white solid.

¹H NMR (CDCl3, 400 MHz) δ 4.88 (s, 1H), 4.48 (s, 1H), 3.52 (s, 1H), 3.01 (s, 3H), 2.07-2.03 (m, 2H), 1.83-1.82 (m, 2H), 1.73-1.70 (m, 2H), 1.61-1.55 (m, 7H), 1.448 (s, 9H).

Step 2:

To a solution of 1H-pyrazole (195.25 mg, 2.87 mmol, 1.20 eq) in MeCN (7.00 mL) were added Cs₂CO₃ (1.56 g, 4.78 mmol, 2.00 eq) and 64_2 (700.00 mg, 2.39 mmol, 1.00 eq). The mixture was stirred at 100° C. for 2 hours. The mixture was diluted with H₂O (20 mL) and extracted with EtOAc (10 mL*3). The combined organic layers were washed with brine (20 mL) and concentrated. The residue was purified by pre-HPLC (basic condition) to give 64_3 (200.00 mg, 732.25 μmol, 30.6% yield, 97.1% purity) as a yellow solid.

MS: m/z RT=0.888 min, 266.0 [M+H]⁺

Step 3:

To a solution of 64_3 (180.00 mg, 678.35 μmol, 1.00 eq) in DCM (2 mL) was added TFA (400.00 μL) at 0° C. The mixture was stirred at 20° C. for 1 hour. The mixture was diluted with H₂O (30 mL) and extracted with DCM (10 mL*2). The aqueous layer was lyophilized to give amine-64 (180.00 mg, 633.91 μmol, 93.5% yield, 98.3% purity, TFA) as colorless oil.

LCMS: RT=0.272 min, m/z 166.2 [M+H]⁺

Step 4:

To a solution of 51_9 (100.00 mg, 353.16 μmol, 1.00 eq) in DMSO (1.5 mL) were added amine-64 (95.48 mg, 529.74 μmol, 1.50 eq) and DIEA (182.57 mg, 1.41 mmol, 246.71 μL, 4.00 eq). The resulting mixture was stirred at 160° C. for 3 hours, filtered and the mother liquid was concentrated. The residue was purified by pre-HPLC (basic condition) and then prep-HPLC (HCl condition) to give A-64 (10.00 mg, 23.42 μmol, 6.6% yield, 100% purity) as a yellow solid.

LCMS: RT=1.981 m/z 412.2[M+H]⁺

¹H NMR (MeOD, 400 MHz) δ 8.41-8.37 (m, 2H), 7.83 (s, 1H), 7.67 (s, 1H), 6.39 (s, 1H), 4.36 (s, 1H), 4.12-4.08 (m, 1H), 3.95 (s, 3H), 3.25-3.23 (d, J=6.4 Hz, 2H), 2.26-2.23 (m, 4H), 2.05-2.02 (m, 2H), 1.99-1.96 (m, 2H), 1.73-1.67 (m, 2H), 1.09 (s, 1H), 0.55-0.50 (m, 2H), 0.27-0.26 (m, 2H).

Preparation of N-((1R,4R)-4-(1H-imidazol-1-yl) cyclohexyl)-5-chloro-4-(5-(cyclopropylmethyl)-1-methyl-1H-pyrazol-4-yl)pyrimidin-2-amine (A-65)

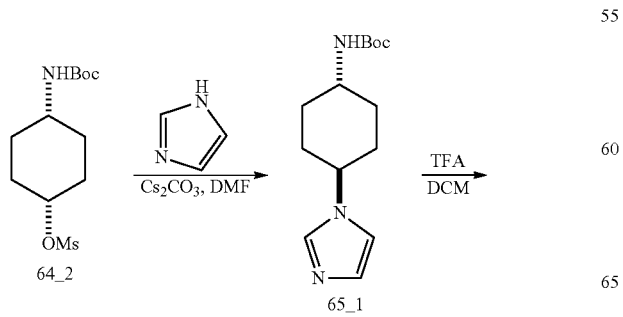

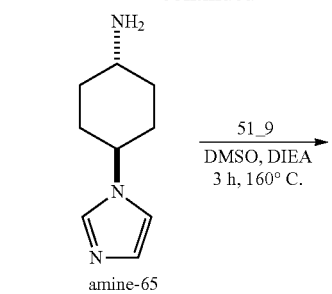

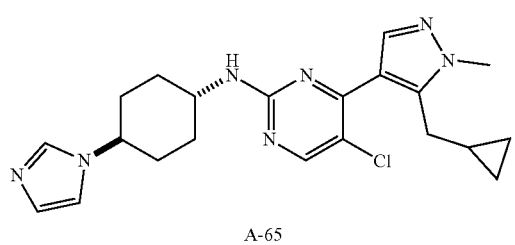

Compound A-65 was synthesized in a manner similar as described for the synthesis of compound A-64 as a yellow solid.

LCMS: RT=1.461 min, m/z 412.2 [M+H]⁺

¹H NMR (MeOD, 400 MHz) δ 9.10 (s, 1H), 8.42 (s, 1H), 7.81 (s, 1H), 7.62 (s, 1H), 4.55-4.49 (m, 1H), 4.13 (s, 1H), 3.96 (s, 3H), 3.25-3.24 (d, J=6.4 Hz, 2H), 2.36-2.28 (m, 4H), 2.08-1.98 (m, 2H), 1.80-1.74 (m, 2H), 1.09 (s, 1H), 0.53-0.51 (m, 2H), 0.27-0.26 (m, 2H).

Preparation of (1R,4R)—N¹-(5-chloro-4-(5-(cyclopropylmethyl)-1-methyl-1H-pyrazol-4-yl)pyrimidin-2-yl)-N⁴-phenylcyclohexane-1,4-diamine (A-68)

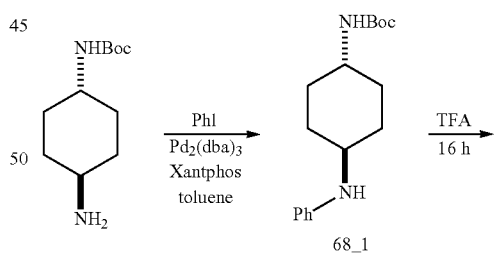

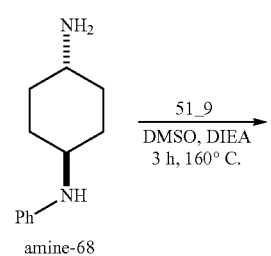

-continued

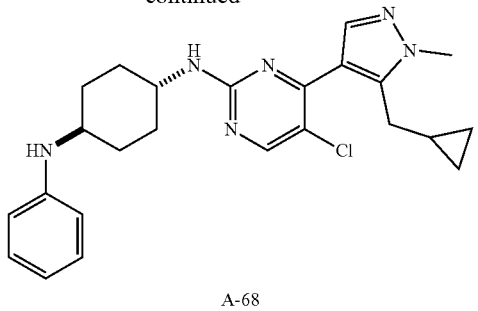

A-68

Step 1:
To a solution of tert-butyl ((1R,4R)-4-aminocyclohexyl)carbamate (500.00 mg, 2.33 mmol, 1.00 eq) and iodobenzene (713.01 mg, 3.49 mmol, 389.63 uL, 1.50 eq) in THF (15 mL) were added t-BuOK (784.35 mg, 6.99 mmol, 3.00 eq) and RuPhos Indoline (100.00 mg). The resulting mixture was stirred at 80° C. for 12 hours under nitrogen. The mixture was filtered and the mother liquid was concentrated. The residue was purified by silica gel column (PE:EA=10:1-4:1) to give 68_1 (300.00 mg, 869.39 μmol, 37.3% yield, 84.1% purity) as a white solid.

LCMS: RT=1.024 min, m/z 291.0 [M+H]+

Step 2 and step 3: Compound A-68 was synthesized in a manner similar as described for the synthesis of compound A-64 as a yellow solid.

LCMS: RT=1.194 min, m/z 437.2 [M+H]+

$^1$H NMR (MeOD, 400 MHz) δ 8.29 (s, 1H), 8.03 (s, 1H), 7.75-7.34 (m, 5H), 3.86 (s, 3H), 3.05 (d, J=6.4 Hz, 2H), 2.00-1.97 (m, 4H), 1.55 (s, 2H), 1.37-1.29 (m, 2H), 0.97 (s, 1H), 0.39 (s, 2H), 0.14 (s, 2H).

Preparation of (5R,8R)-8-((5-chloro-4-(5-(cyclopropylmethyl)-1-methyl-1H-pyrazol-4-yl)pyrimidin-2-yl)amino)-1-azaspiro[4,5]decan-2-one (A-71)

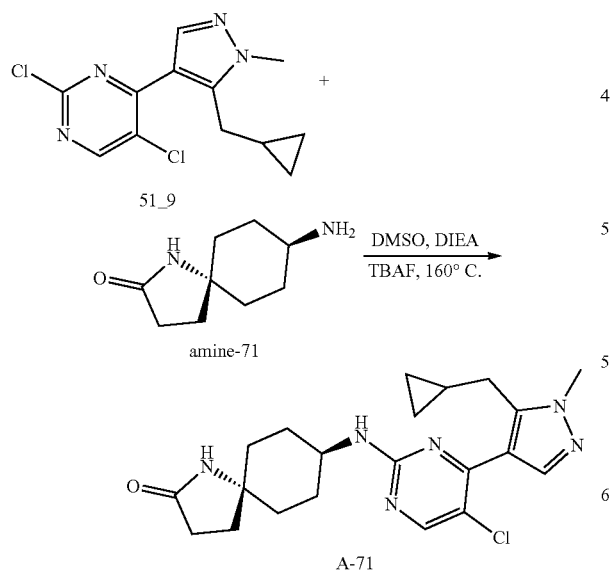

To a solution of amine-71 (180.00 mg, 879.34 μmol, 1.00 eq, HCl) and 51_9 (248.99 mg, 879.34 μmol, 1.00 eq) in DMSO (2.7 mL) were added DIEA (614.30 μL, 3.52 mmol, 4.00 eq) and TBAF (1 M, 175.87 μL, 0.20 eq). The mixture was stirred at 160° C. for 3 hours. The mixture was cooled down and filtered. The solid were washed with MeOH (10 mL) at room temperature and then EtOAc (3 mL) at 50° C. to give A-71 (40.00 mg, 90.39 μmol, 11.4% yield, 93.7% purity) as a white solid.

LCMS: RT=2.836 min, m/z 415.2 [M+H]+

$^1$H NMR (DMSO, 400 MHz) δ 8.26 (s, 1H), 8.00 (s, 1H), 7.72 (s, 1H), 7.20 (s, 1H), 3.85 (s, 3H), 3.70-3.68 (m, 1H), 3.06 (d, J=6.4 Hz, 2H), 2.19-2.15 (m, 2H), 1.86-1.80 (m, 5H), 1.64-1.60 (m, 3H), 1.49-1.41 (m, 5H), 0.97 (s, 1H), 0.40 (s, 2H), 0.13 (s, 2H).

Preparation of (1R,4R)—N$^1$-benzyl-N$^4$-(5-chloro-4-(5-(cyclopropylmethyl)-1-methyl-1H-pyrazol-4-yl)pyrimidin-2-yl)cyclohexane-1,4-diamine (A-74)

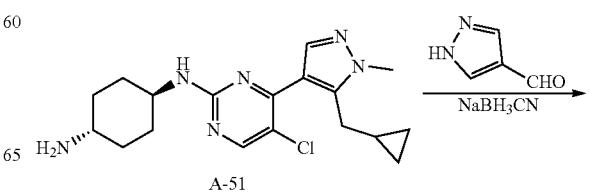

To a solution of A-51 (200.00 mg, 554.20 μmol, 1.00 eq) and benzaldehyde (58.81 mg, 554.20 umol, 56.01 μL, 1.00 eq) were added AcOH (33.28 mg, 554.20 μmol, 31.70 μL, 1.00 eq) and NaBH$_3$CN (69.65 mg, 1.11 mmol, 2.00 eq). The mixture was stirred at 15° C. for 16 hours. The mixture was quenched with aqueous NaHCO$_3$ (1 mL) and concentrated. The residue was purified by prep-HPLC (column: Phenomenex Gemini 150*25 mm*10 um; mobile phase: [water (0.05% ammonia hydroxide v/v)-ACN]; B %: 55%-85%, 12 min) to give A-74 (100.00 mg, 217.80 μmol, 39.3% yield, 98.2% purity) as a pink solid.

LCMS: RT=2.74 min, m/z 451.2 [M+H]+

$^1$H NMR (CDCl3, 400 MHz) δ 8.20-8.13 (m, 2H), 7.34-7.33 (m, 5H), 4.87 (d, J=8.4 Hz, 1H), 3.91 (s, 3H), 3.84 (s, 3H), 3.07-3.06 (m, 2H), 2.58-2.52 (m, 1H), 2.16-2.02 (m, 4H), 1.32-1.22 (m, 4H), 1.01-0.99 (m, 1H), 0.49-0.45 (m, 2H), 0.18-0.16 (m, 2H).

Preparation of (1R,4R)—N$^1$-((1H-pyrazol-4-yl)methyl)-N$^4$-(5-chloro-4-(5-(cyclopropylmethyl)-1-methyl-1H-pyrazol-4-yl)pyrimidin-2-yl)cyclohexane-1,4-diamine (A-75)

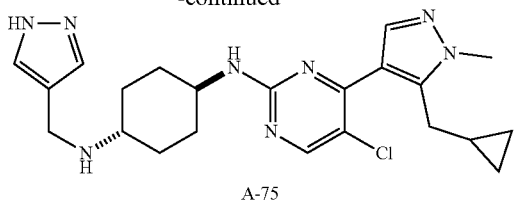

A-75

To a solution of A-51 (200.00 mg, 554.20 μmol, 1.00 eq) and 1H-pyrazole-4-carbaldehyde (53.25 mg, 554.20 μmol, 1.00 eq) were added AcOH (34.86 μL, 609.62 umol, 1.10 eq) and NaBH₃CN (69.65 mg, 1.11 mmol, 2.00 eq). The mixture was stirred at 15° C. for 16 hours. The mixture was quenched with aqueous NaHCO₃ (1 mL) and concentrated. The residue was purified by prep-HPLC (column: Phenomenex Gemini 150*25 mm*10 um; mobile phase: [water (0.05% ammonia hydroxide v/v)-ACN]; B %: 39%-39%, 12 min) to give A-75 (4.00 mg, 9.04 μmol, 1.6% yield, 99.7% purity) as a yellow solid.

LCMS: RT=2.95 min, m/z 441.2 [M+H]⁺

¹H NMR (CDCl3, 400 MHz) δ 8.21-8.12 (m, 2H), 7.61 (s, 2H), 4.90 (d, J=8.4 Hz, 1H), 3.91 (s, 3H), 3.85-3.80 (m, 3H), 3.06-3.05 (m, 2H), 2.70 (m, 1H), 2.19-2.07 (m, 4H), 1.42-1.23 (m, 4H), 1.09 (m, 1H), 0.50-0.45 (m, 2H), 0.18-0.14 (m, 2H).

Preparation of (1R,4R)—N¹-(5-chloro-4-(5-(cyclopropylmethyl)-1-methyl-1H-pyrazol-4-yl) pyrimidin-2-yl)-N⁴-(pyridin-3-ylmethyl)cyclohexane-1,4-diamine (A-76)

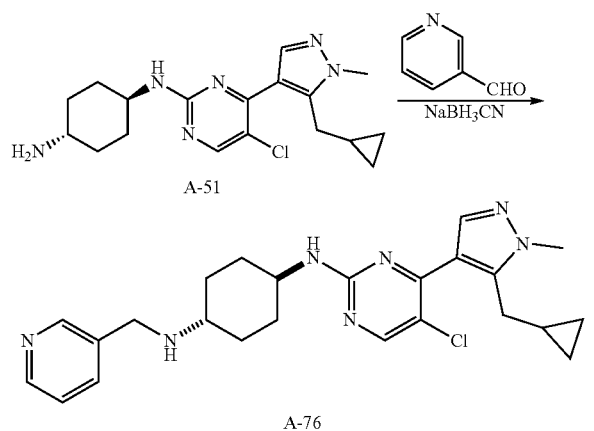

A-76

To a solution of A-51 (200.00 mg, 554.20 μmol, 1.00 eq) and pyridine-3-carbalde hyde (59.36 mg, 554.20 μmol, 52.07 uL, 1.00 eq) were added AcOH (33.28 mg, 554.20 μmol, 31.70 μL, 1.00 eq) and NaBH₃CN (69.65 mg, 1.11 mmol, 2.00 eq). The mixture was stirred at 15° C. for 16 hours. The mixture was quenched with aqueous NaHCO₃ (1 mL) and concentrated. The residue was purified by prep-HPLC (column: Phenomenex Gemini 150*25 mm*10 um; mobile phase: [water (0.05% ammonia hydroxide v/v)-ACN]; B %: 40%-58%, 12 min) to give A-76 (100.00 mg, 219.09 μmol, 39.5% yield, 98.8% purity) as a yellow solid.

LCMS: RT=2.381 min, m/z 452.2 [M+H]⁺

¹H NMR (CDCl3, 400 MHz) δ8.58-8.51 (m, 2H), 7.69 (d, J=8.0 Hz, 1H), 7.27 (s, 1H), 4.87 (d, J=8.0 Hz, 1H), 3.91 (s, 3H), 3.85-3.81 (m, 3H), 3.07-3.06 (m, 2H), 2.56-2.51 (m, 1H), 2.16-2.01 (m, 4H), 1.30-1.22 (m, 4H), 1.09 (m, 1H), 0.50-0.46 (m, 2H), 0.19-0.16 (m, 2H).

Preparation of (1R, 4R)—N¹-((1H-pyrazol-4-yl)methyl)-N⁴-(4-(5-(cyclopropylmethyl)-1-methyl-1H-pyrazol-4-yl)pyrimidin-2-yl)cyclohexane-1,4-diamine (A80)

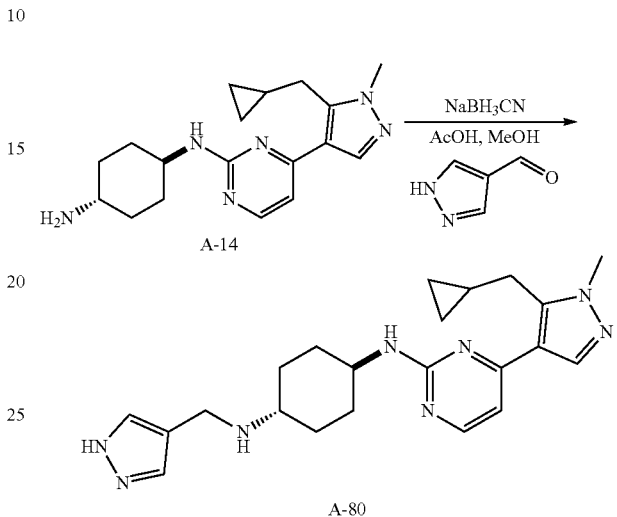

A-80

To a solution of A-14 (200.00 mg, 612.67 μmol, 1.00 eq) and 1H-pyrazole-4-carbaldehyde (58.87 mg, 612.67 μmol, 1.00 eq) were added AcOH (36.79 mg, 612.67 μmol, 35.04 uL, 1.00 eq) and NaBH₃CN (77.00 mg, 1.23 mmol, 2.00 eq). The mixture was stirred at 15° C. for 16 hours. The mixture was quenched with aqueous NaHCO₃ (1 mL) and concentrated. The residue was purified by prep-HPLC (basic condition) to give A-80 (20.00 mg, 48.90 μmol, 8% yield, 99.4% purity) as a yellow solid.

LCMS: RT=2.418 min, m/z 407.2 [M+H]⁺

¹H NMR (CDCl₃, 400 MHz) δ 8.17 (d, J=5.2 Hz, 1H), 7.83 (s, 1H), 7.58 (s, 1H), 6.71 (d, J=6.2 Hz, 1H), 4.88 (d, J=7.6 Hz, 1H), 3.89 (s, 4H), 3.81 (s, 2H), 3.21 (d, J=6.0 Hz, 2H), 2.61 (s, 1H), 2.21-2.03 (m, 4H), 1.36-1.25 (m, 4H), 1.09 (s, 1H), 0.48-0.46 (m, 2H), 0.25-0.24 (m, 2H).

Preparation of (1R,4R)—N¹-(4-(5-(cyclopropylmethyl)-1-methyl-1H-pyrazol-4-yl)pyrimidin-2-yl)-N⁴-((1-methyl-1H-pyrazol-4-yl)methyl)cyclohexane-1,4-diamine (A81)

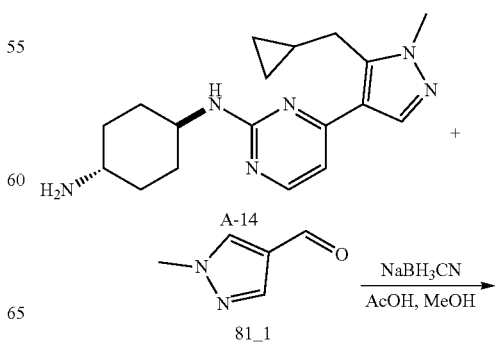

81_1

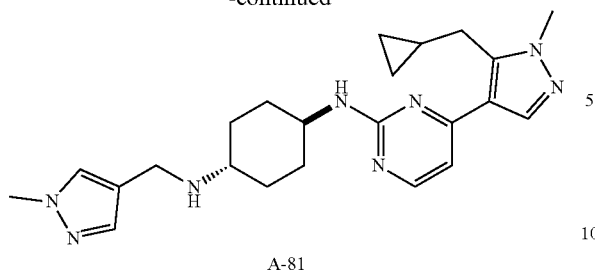

A-81

To a solution of A-14 (200.00 mg, 612.67 μmol, 1.00 eq) and compound 81_1 (67.46 mg, 612.67 μmol, 1.00 eq) were added AcOH (36.79 mg, 612.67 μmol, 35.04 μL, 1.00 eq) and NaBH₃CN (77.00 mg, 1.23 mmol, 2.00 eq). The mixture was stirred at 15° C. for 16 hours. The mixture was quenched with a.q NaHCO₃ (1 mL) and concentrated. The residue was purified by prep-HPLC (basic condition) to give A-81 (40.00 mg, 87.81 μmol, 14.3% yield, 92% purity) as a yellow solid.

LCMS: RT=2.469 min, m/z 421.2 [M+H]⁺

¹H NMR (CDCl₃, 400 MHz) δ 8.17 (d, J=5.2 Hz, 1H), 7.82 (s, 1H), 7.57 (s, 1H), 7.51 (s, 1H), 6.7 (d, J=6.2 Hz, 1H), 4.84 (d, J=7.6 Hz, 1H), 3.89-3.85 (m, 8H), 3.19 (d, J=6.0 Hz, 2H), 2.73 (s, 1H), 2.25-2.12 (m, 4H), 1.54 (m, 1H), 1.29-1.23 (m, 2H), 1.07 (s, 1H), 0.50-0.46 (m, 2H), 0.26-0.24 (m, 2H).

Preparation of (1R,4R)—N¹-((1H-pyrazol-3-yl)methyl)-N⁴-(5-chloro-4-(5-(cyclopropylmethyl)-1-methyl-1H-pyrazol-4-yl)pyrimidin-2-yl)cyclohexane-1,4-diamine (A-82)

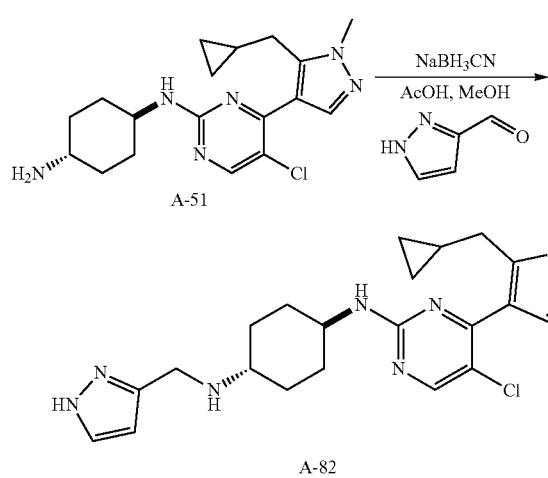

To a solution of A-51 (200.00 mg, 554.20 μmol, 1.00 eq) and 1H-pyrazole-3-carbaldehyde (53.25 mg, 554.20 μmol, 1.00 eq) were added AcOH (31.7 μL, 554.20 μmol, 1.00 eq) and NaBH₃CN (69.65 mg, 1.11 mmol, 2.00 eq). The mixture was stirred at 15° C. for 16 hours. The mixture was quenched with a.q NaHCO₃ (1 mL) and concentrated. The residue was purified by prep-HPLC (basic condition) to give A-82 (35.00 mg, 79.28 μmol, 14.3% yield, 99.9% purity) as a yellow solid.

LCMS: RT=2.867 min, m/z 441.2 [M+H]⁺

¹H NMR (CDCl₃, 400 MHz) δ 8.20 (s, 1H), 8.13 (s, 1H), 7.53 (s, 1H), 6.22 (s, 1H), 4.91 (d, J=7.6 Hz, 1H), 3.93 (s, 2H), 3.91 (s, 3H), 3.81 (s, 1H), 3.49 (s, 1H), 3.07 (d, J=5.6 Hz, 2H), 2.56-2.53 (m, 1H), 2.16-2.02 (m, 4H), 1.33-1.32 (m, 4H), 1.05 (s, 1H), 0.48-0.45 (m, 2H), 0.18-0.16 (m, 2H).

Preparation of (1R,4R)—N¹-(1-(1H-pyrazol-4-yl)ethyl)-N⁴-(5-chloro-4-(5-(cyclopropylmethyl)-1-methyl-1H-pyrazol-4-yl)pyrimidin-2-yl)cyclohexane-1,4-diamine (A83)

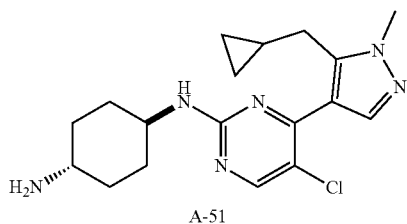

A-51

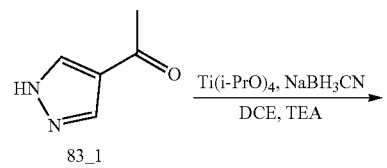

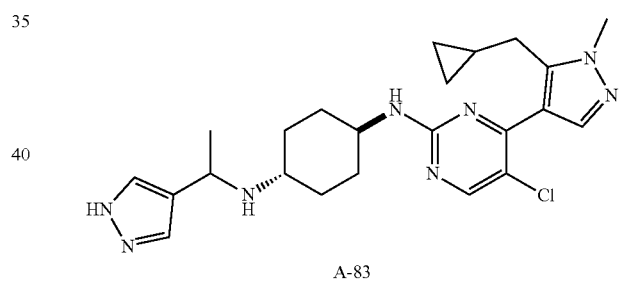

A-83

To a solution of A-51 (100.00 mg, 251.67 μmol, 1.00 eq, HCl), compound 83_1 (27.71 mg, 251.67 μmol, 1.00 eq) were added TEA (503.34 μmol, 69.77 uL, 2.00 eq) and Ti(i-PrO)₄ (149 μL, 503.34 μmol, 2.00 eq). The mixture was stirred at 80° C. for 12 hours. Then NaBH₃CN (39.54 mg, 629.18 μmol, 2.50 eq) was added. The resulting mixture was stirred at 15° C. for 4 hours. The mixture was quenched with a.q NaHCO₃ (50 mL) and extracted with DCM (50 mL*2). The organic layer was concentrated and purified by prep-HPLC (basic condition) to give A-83 (20.00 mg, 43.96 μmol, 17.5% yield) as a yellow solid.

LCMS: RT=1.897 m/z 455.2[M+H]⁺

¹H NMR (CDCl₃, 400 MHz) δ 8.19 (s, 1H), 8.12 (s, 1H), 7.52 (s, 2H), 4.90 (d, J=7.6 Hz, 1H), 4.05-4.00 (m, 1H), 3.91 (s, 3H), 3.78-3.76 (m, 1H), 3.06 (d, J=5.6 Hz, 2H), 2.49-2.46 (m, 1H), 2.11-2.08 (m, 4H), 1.40-1.38 (m, 3H), 1.25-1.19 (m, 4H), 1.05 (m, 1H), 0.47-0.44 (m, 2H), 0.16-0.15 (m, 2H).

Preparation of N-((1R,4R)-4-((5-chloro-4-(5-(cyclopropylmethyl)-1-methyl-1H-pyrazol-4-yl)pyrimidin-2-yl)amino)cyclohexyl)-1H-pyrazole-4-carboxamide (A87)

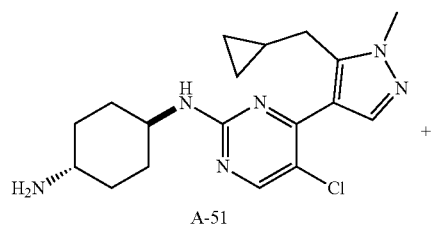

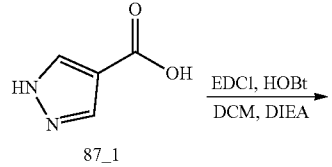

To a solution of compound 87_1 (46.59 mg, 415.65 μmol, 1.00 eq) in DCM (4 mL) were added DIEA (181.5 μL, 1.04 mmol, 2.50 eq), EDCI (95.62 mg, 498.78 μmol, 1.20 eq) and HOBt (11.23 mg, 83.13 μmol, 0.20 eq) at 0° C. The reaction mixture was stirred at 0° C. for 0.5 hour. The solution of A-51 (150.00 mg, 415.65 μmol, 1.00 eq) in DCM (4.5 mL) was added. The resulting mixture was stirred at 20° C. for 16 hours. The mixture was diluted with H₂O (50 mL) and extracted with DCM (40 mL*3). The organic layer was concentrated and purified by prep-HPLC (HCl condition) to give A-87 (80.00 mg, 160.61 μmol, 38.6% yield, 98.6% purity, HCl) as a yellow solid.

LCMS: RT=2.391 m/z 455.2[M+H]⁺

¹H NMR (MeOD, 400 MHz) δ 8.48 (s, 1H), 8.39 (s, 1H), 8.16 (s, 2H), 4.04 (s, 1H), 3.96 (s, 3H), 3.93-3.90 (m, 1H), 3.24 (d, J=6.4 Hz, 2H), 2.18-2.04 (m, 4H), 1.67-1.53 (m, 4H), 1.18 (s, 1H), 0.57-0.55 (m, 2H), 0.30-0.29 (m, 2H).

Preparation of (1R,4R)—N¹-(5-chloro-4-(5-(cyclopropylmethyl)-1-methyl-1H-pyrazol-4-yl)pyrimidin-2-yl)-N⁴-((5-methyl-1H-pyrazol-4-yl)methyl)cyclohexane-1,4-diamine (A-91)

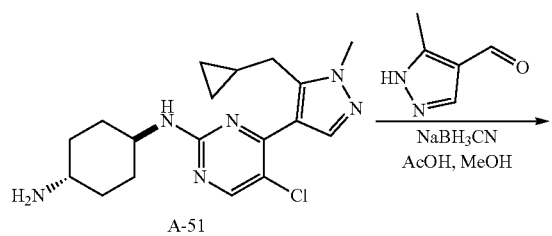

To a solution of A-51 (150.00 mg, 415.65 mol, 1.00 eq) and 5-methyl-1H-pyrazole-4-carbaldehyde (54.92 mg, 498.78 μmol, 1.20 eq) in MeOH (1.5 mL) were added AcOH (23.77 μL, 415.65 μmol, 1.00 eq) and NaBH₃CN (78.36 mg, 1.25 mmol, 3.00 eq). The mixture was stirred at 15° C. for 16 hours. The mixture was quenched with a.q NaHCO₃ (10 mL) and extracted with EA (20 mL*2). The combined organic layers were concentrated and purified by prep-HPLC (HCl condition) to give A-91 (20.00 mg, 36.22 μmol, 8.7% yield, 89% purity, HCl) as a white solid.

LCMS: RT=2.425 m/z 455.2[M+H]⁺

¹HNMR (MeOD, 400 MHz) δ 8.44-8.41 (m, 2H), 8.23 (s, 1H), 4.26 (s, 2H), 4.13-4.06 (m, 1H), 3.95 (s, 3H), 3.24 (d, J=6.4 Hz, 2H), 2.51 (s, 3H), 2.40-2.24 (m, 4H), 1.76-1.61 (m, 4H), 1.09 (s, 1H), 0.54-0.53 (m, 2H), 0.28-0.27 (m, 2H).

Preparation of (1R,4R)—N¹-(5-chloro-4-(5-(cyclopropylmethyl)-1-methyl-1H-pyrazol-4-yl)pyrimidin-2-yl)-N⁴-(2,2,2-trifluoroethyl)cyclohexane-1,4-diamine (A94)

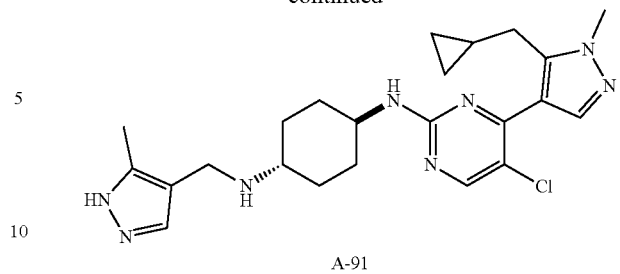

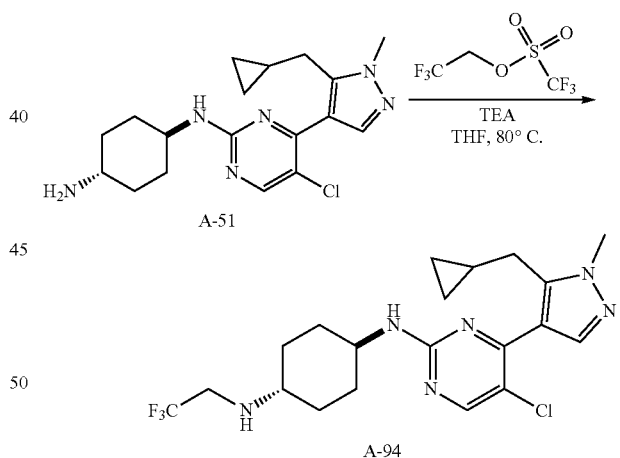

To a solution of A-51 (150.00 mg, 415.65 μmol, 1.00 eq) in THF (4.5 mL) were added TEA (144.04 μL, 1.04 mmol, 2.50 eq) and 2,2,2-trifluoroethyl trifluoromethanesulfonate (115.77 mg, 498.78 μmol, 1.20 eq). The mixture was stirred at 50° C. for 16 hours. The mixture was concentrated and purified by prep-HPLC (HCl condition) to give A-94 (80.00 mg, 163.38 μmol, 39.3% yield, 97.9% purity, HCl) as a yellow solid.

LCMS: RT=2.137 min, m/z 443.2 [M+H]⁺

¹H NMR (MeOD, 400 MHz) δ 8.45 (m, 2H), 4.15-4.09 (m, 2H), 4.09 (s, 1H), 3.95 (s, 3H), 3.39-3.36 (m, 1H), 3.22-3.21 (m, 2H), 2.33-2.25 (m, 4H), 1.71-1.56 (m, 4H), 1.09 (s, 1H), 0.54-0.52 (m, 2H), 0.28-0.27 (m, 2H).

Preparation of Preparation of (1R,4R)—N1-((1H-pyrazol-4-yl)methyl)-N4-(5-chloro-4-(5-(cyclopropylmethyl)-1-methyl-1H-pyrazol-4-yl)pyrimidin-2-yl)-N1-(2,2,2-trifluoroethyl)cyclohexane-1,4-diamine (A-95)

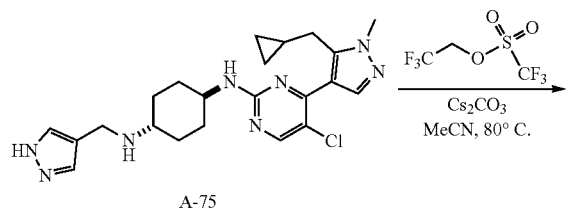

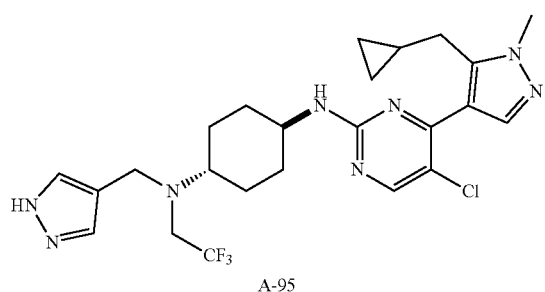

To a solution of A-75 (150.00 mg, 340.16 μmol, 1.00 eq) in MeCN (4.5 mL) were added Cs$_2$CO$_3$ (221.66 mg, 680.32 μmol, 2.00 eq) and 2,2,2-trifluoroethyl trifluoromethanesulfonate (118.43 mg, 510.24 μmol, 1.50 eq). The mixture was stirred at 70° C. for 16 hours. The mixture was filtered; the filtrate was concentrated and purified by prep-HPLC (HCl condition) to give A-95 (20.00 mg, 35.7 μmol, 10.5% yield, 100% purity, HCl) as a white solid.

LCMS: RT=2.285 m/z 523.2[M+H]$^+$ $^1$H NMR (MeOD, 400 MHz) δ 8.41-8.39 (m, 2H), 8.02 (s, 1H), 7.76 (s, 1H), 5.03-4.97 (m, 2H), 4.23 (s, 2H), 4.12-4.04 (m, 1H), 3.95 (s, 3H), 3.21 (d, J=6.4 Hz, 3H), 2.34-2.23 (m, 4H), 1.65-1.53 (m, 4H), 1.09 (s, 1H), 0.54-0.52 (m, 2H), 0.27-0.26 (m, 2H).

Preparation of (1R,4R)—N$^1$,N$^1$-bis((1H-pyrazol-4-yl)methyl)-N$^4$-(5-chloro-4-(5-(cyclopropylmethyl)-1-methyl-1H-pyrazol-4-yl)pyrimidin-2-yl)cyclohexane-1,4-diamine (A-96)

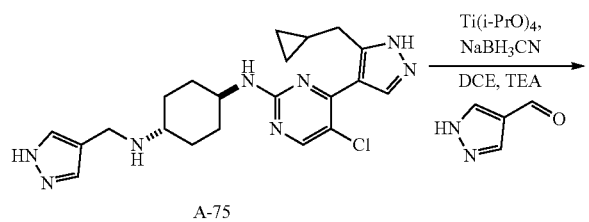

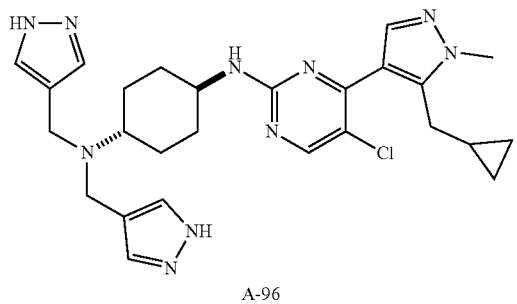

To a solution of A-75 (50.00 mg, 113.4 μmol, 1.00 eq) and compound 1H-pyrazole-4-carbaldehyde (32.69 mg, 340.17 μmol, 3.00 eq) were added TEA (31.44 μL, 226.78 μmol, 2.00 eq) and Ti(Oi-Pr)$_4$ (67.1 μL, 226.78 μmol, 2.00 eq). The mixture was stirred at 80° C. for 12 hours. NaBH$_3$CN (21.38 mg, 340.17 μmol, 3.00 eq) was added and the resulting mixture was stirred at 15° C. for 4 hours. The reaction was quenched with a.q NaHCO$_3$ (1 mL) and filtered. The filtrate was purified by prep-HPLC (TFA and then basic condition) to give A-96 (7.00 mg, 13.10 umol, 11.6% yield, 97.5% purity) as a white solid.

LCMS: RT=2.382 m/z 521.3[M+H]$^+$ $^1$H NMR (MeOD, 400 MHz) δ 8.23 (m, 2H), 8.03 (s, 1H), 7.78 (s, 4H), 4.47-4.29 (m, 4H), 3.91-3.87 (m, 4H), 3.12 (d, J=6.4 Hz, 2H), 2.27-2.22 (m, 4H), 1.94-1.85 (m, 2H), 1.46-1.36 (m, 2H), 1.01-1.00 (m, 1H), 0.45-0.44 (m, 2H), 0.14-0.13 (m, 2H).

Preparation of (1R,4R)—N$^1$-(4-(5-(cyclopropylmethyl)-1-methyl-1H-pyrazol-4-yl)-5-fluoropyrimidin-2-yl)cyclohexane-1,4-diamine (A-86)

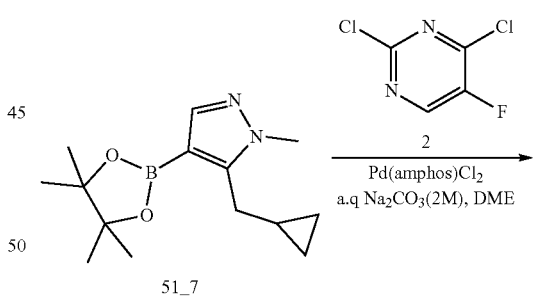

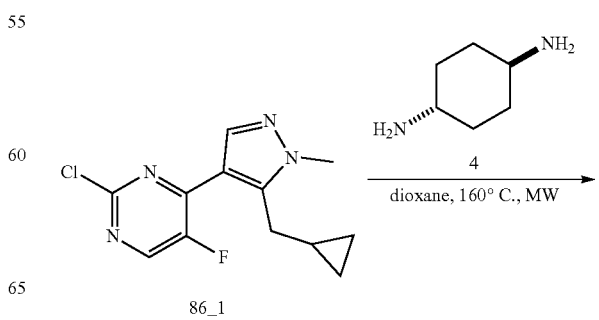

-continued

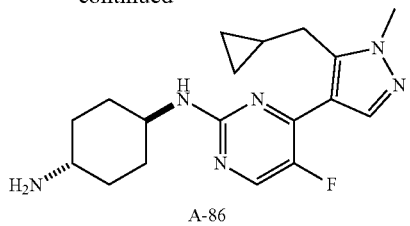
A-86

Step 1:

To a solution of compound 51_7 (800 mg, 3.05 mmol, 1.00 eq) in DME (16 mL) were added compound 2 (509.54 mg, 3.05 mmol, 1.00 eq), Na$_2$CO$_3$ (2 M, 4.6 mL, 3.00 eq) and 4-ditert-butylphosphanyl-N,N-dimethyl-aniline;dichloropalladium (108.04 mg, 152.50 μmol, 108 uL, 0.05 eq) under nitrogen. The resulting mixture was stirred at 85° C. for 2 hours under nitrogen. The mixture was diluted with H$_2$O (50 mL) and extracted with EA (50 mL). The organic layer was concentrated to give compound 86_1 (1.20 g, crude) as a yellow oil.

LCMS: RT=1.819 min, m/z 267.1 [M+H]$^+$

Step 2:

The mixture of compound 86_1 (1.10 g, 4.12 mmol, 1.00 eq) and compound 4 (1.88 g, 16.48 mmol, 4.00 eq) in dioxane (16 mL) was stirred at 130° C. for 8 hours under microwave. The mixture was filtered and concentrated. The residue was purified by pre-HPLC (HCl condition) to give A-86 (1.30 g, crude) as a yellow solid. A-86 (300 mg) was purified again by prep-HPLC (HCl condition) to give A-86 (20.00 mg, 52.51 μmol, 12.1% yield, 100% purity, HCl) as a yellow solid.

LCMS: RT=2.321 min, m/z 345.2 [M+H]$^+$ $^1$H NMR (MeOD, 400 MHz) δ 8.37-8.36 (m, 1H), 8.23-8.22 (m, 1H), 4.07-4.03 (m, 1H), 3.96 (s, 3H), 3.21 (d, J=6.4 Hz, 2H), 2.24-2.18 (m, 4H), 1.68-1.57 (m, 2H), 1.19 (s, 1H), 0.57-0.55 (m, 2H), 0.38-0.34 (m, 2H).

Preparation of (1R,4R)—N$^1$-((1H-pyrazol-4-yl)methyl)-N$^4$-(4-(5-(cyclopropylmethyl)-1-methyl-1H-pyrazol-4-yl)-5-fluoropyrimidin-2-yl)cyclohexane-1,4-diamine (A-85)

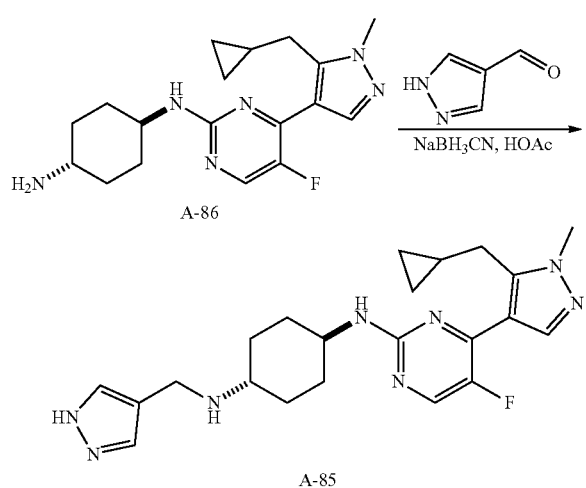

To a solution of A-86 (300.00 mg, 783.90 μmol, 1.00 eq) and 1H-pyrazole-4-carbaldehyde (82.86 mg, 862.29 μmol, 1.10 eq) in MeOH (3 mL) were added AcOH (49.31 μL, 862.29 μmol, 1.10 eq) and NaBH$_3$CN (98.52 mg, 1.57 mmol, 2.00 eq). The mixture was stirred at 15° C. for 16 hours. The mixture was quenched with a.q NaHCO$_3$ (1 mL) and concentrated. The residue product was purified by prep-HPLC (basic condition) to give A-85 (50.00 mg, 111.53 μmol, 14.2% yield, 94.7% purity) as a yellow solid.

LCMS: RT=2.472 min, m/z 425.3 [M+H]$^+$ $^1$H NMR (CDCl$_3$, 400 MHz) δ 8.10-8.09 (m, 1H), 8.02-8.01 (m, 1H), 7.60 (s, 1H), 4.80 (d, J=8.4 Hz, 1H), 3.91 (s, 3H), 3.84 (m, 3H), 3.22-3.21 (m, 2H), 2.68 (s, 1H), 2.21-2.06 (m, 4H), 1.41-1.35 (m, 2H), 1.30-1.24 (m, 3H), 1.10-1.09 (m, 1H), 0.49-0.45 (m, 2H), 0.24-0.22 (m, 2H).

Biological Experimental Procedures

Primary Screen in RKO Cells for Compounds Having Typical CKIα Inhibitory Activity (β-catenin and p53 stabilization and histone H2AX phosphorylation; see Elyada et al, Nature 2011 Feb. 17; 470 (7334):409-13; Pribluda et al, Cancer Cell 2013 Aug. 12; 24(2):242-56). RKO colorectal cells were incubated with 10 μM of each of the compounds for 16 hours at 37° C. Cells were washed with PBS and cell pellets were incubated with ice cold protein lysis buffer containing protease inhibitor cocktail (1/200; Calbiochem) and phosphatase inhibitors (20 mM p-nitrophenyl phosphate (PNPP), 20 mM 3-glycerophosphate and 300 nM okadaic acid). Western blot analysis was performed by means of standard techniques. Blots were incubated with antibodies detecting β-catenin (1/2,500; BD Transduction), p53 (DO-1&1801 hybridoma mix; dilution of 1:20 of supernatants from each), CKIα (C-19; 1/1,000; Santa Cruz Biotechnology) and phospho-histoneH2AX (S139; 1/1,000; Millipore). Secondary antibodies were HRP-linked goat anti-mouse, goat anti-rabbit and rabbit anti-goat antibodies (all 1/10,000; Jackson). Blots were developed using ECL (GE Healthcare).

Dose Response Assay of the Most Active Compounds.

Figure 1B:
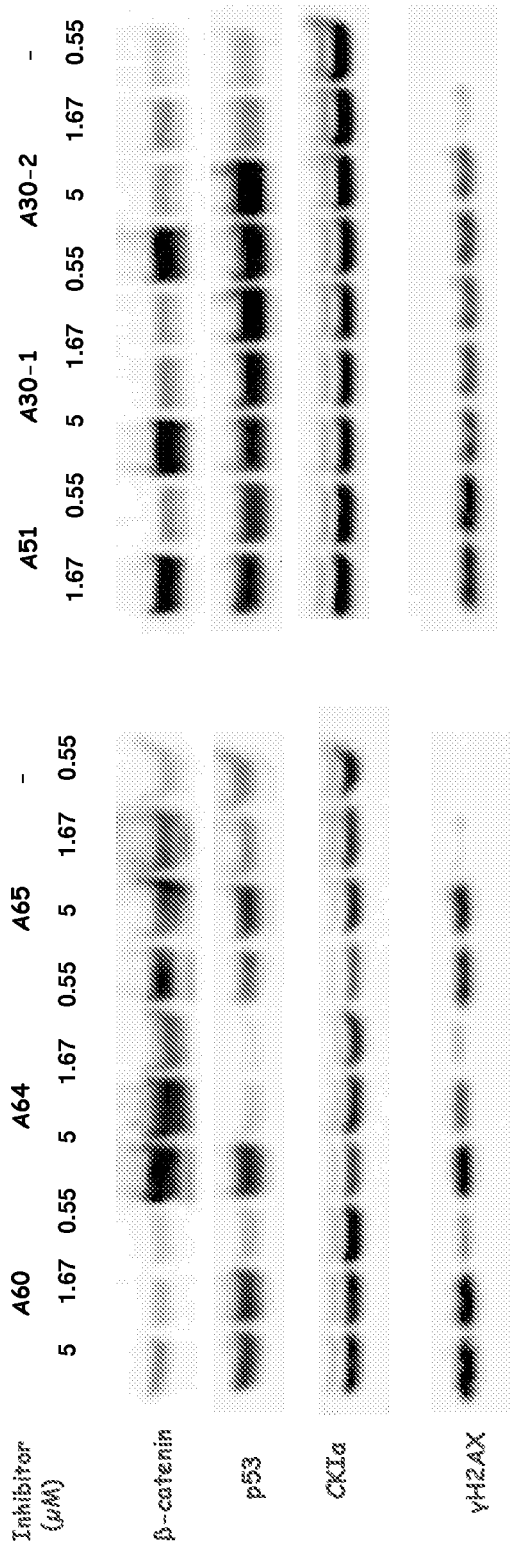
Figure 2A:
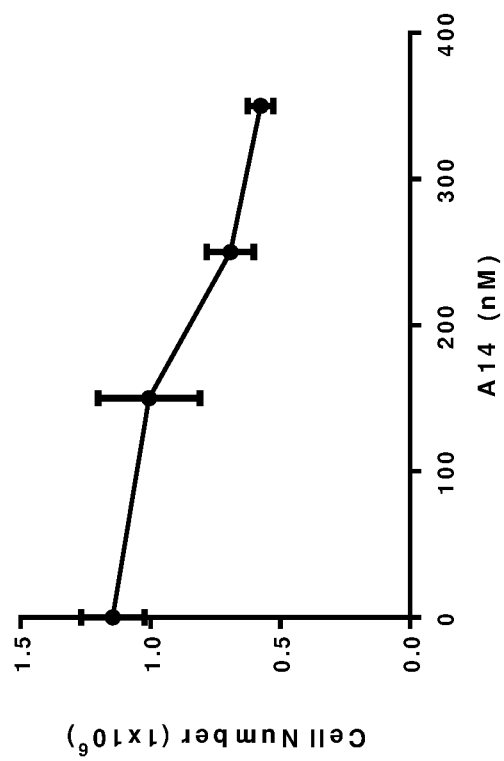
FIGS. 2A-2D show that the CKIα inhibitor A14 induces apoptosis of bone marrow cells isolated from CML blast crisis mice in a dose dependent manner (ex vivo).
Figure 2B:
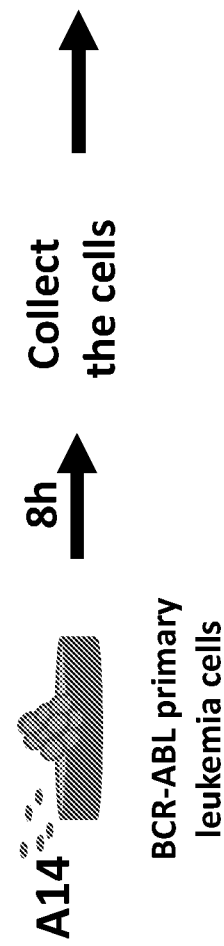
Figure 2C:
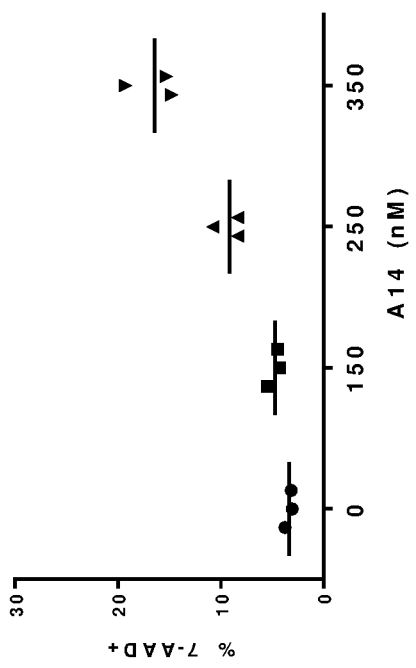
Figure 2D:
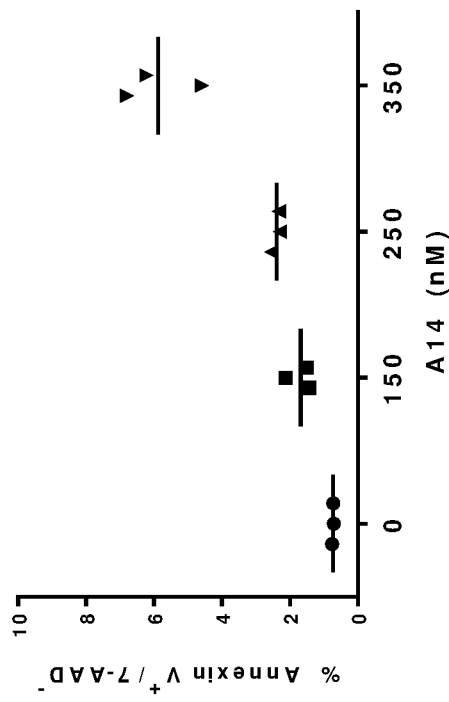

Active compounds were further analyzed in a dose-response experiment (FIGS. 1A and 1B). Similar to the primary screen, RKO cells were incubated with descending concentrations of each of the active compounds for 16 hours at 37° C. Cell extract isolation and Western Blot analysis were similar to the primary screen.

Generation of a Mouse Model of CML Blast Crisis and Inhibitor Studies in this Model.

To generate the BCR-ABL-inducible chronic myeloid leukemia (CML) model, bone marrow (BM) cells from 10 weeks wild type mouse were extracted and enriched for cKit expressing cells (EasySep #18757) and incubated overnight at 37° C. in RPMI growth medium supplemented with 15% FCS, L-Glutamine, Pen/Strep (Biological Industries, Israel) and stem cell factor (SCF), IL-3, IL-6 and TPO (Peprotech). The culture was then infected with p210BCR-ABL-IRES-GFP retrovirus construct containing supernatant medium for 4 hours, then growth medium was added and infected cells were incubated at 37° C. for additional 24 h. The culture was then injected I.V. into sublethally irradiated (500 rad) mice. Upon observing a fast steady increase of GFP-expressing cells in the peripheral blood of inoculated mice (by FACS) and rising numbers of leukocyte and immature cells (detected by Wright-Giemsa stained blood films), mice were sacrificed and their BM cells were transferred to new sublethally irradiated WT hosts; each such transfer was termed disease generation. By the fourth transfer, the hosts were no longer sublethally irradiated prior to disease transfer. Blast crisis development was readily detectable by a highly abnormal number of blast cells, more than 30% of white blood cells (WBC) in the peripheral blood (PB), and short time intervals between transfers. CKI inhibitor studies were performed on late generation diseases, in which PB blasts were easily detectable, with no host irradiation and a short generation time (up to 12 days). Mice were monitored daily for cachexia, weight loss, lethargy, and ruff coats, and moribund mice were sacrificed upon moribund.

Figure 3A:
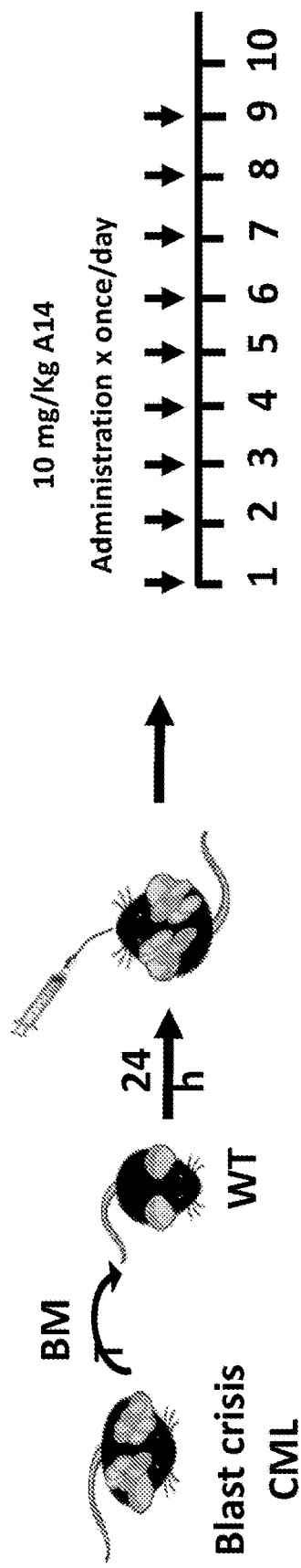
FIGS. 3A-3C demonstrate that A14 significantly reduces the leukemia cell burden in the peripheral blood and bone marrow in vivo in CML blast crisis mice.
Figure 3C:
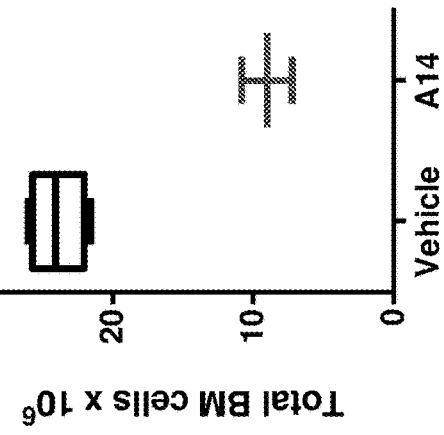
Figure 3B:
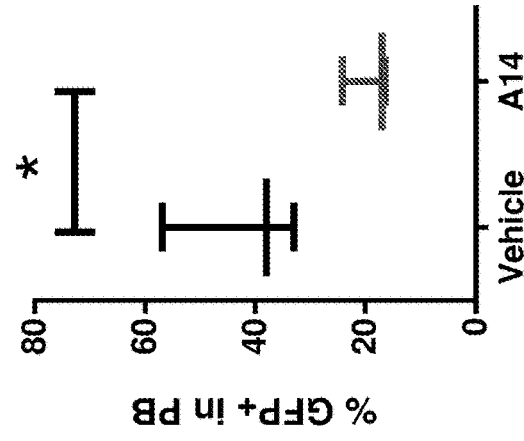
Figure 5:
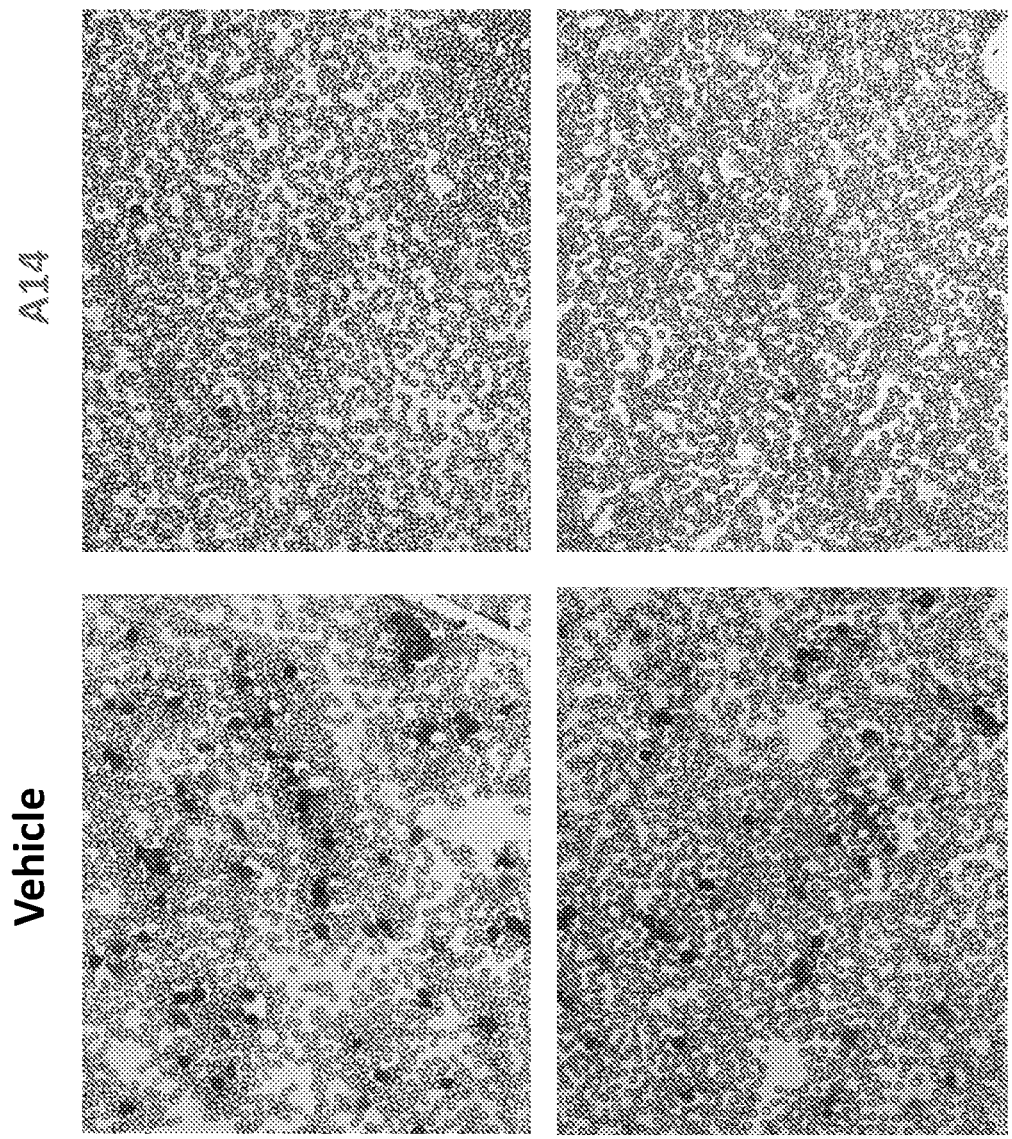
FIG. 5 shows representative photographs of blood smears from A14 treated compared to vehicle-treated CML blast crisis mouse at day 9 following BM transplantation.

For evaluating CKIα inhibition effect on CML, a selective CKIα inhibitor (A14) was administered by oral gavage once a day at a dose of 10 mg/kg, starting from 24 h after BM transplantation (BMT) (FIG. 3A). The inhibitor was dissolved in 1% methyl cellulose with 0.1% Tween 80 and 0.2% Poly-ethylene glycol (Vehicle). Control mice were treated with the vehicle only.

Ex Vivo Inhibitor Effects (FIGS. 2A and 13A-E).

Freshly isolated BM from AML (13A-E) or CML blast crisis (2A) carrying mice were grown in RPMI supplemented with 15% FCS, L-Glutamine, Pen/Strep, Hepes, Sodium Pyruvate and non-essential amino acids (Biological Industries, Israel). CKI inhibitors (A14, A51, A75 or A86) were dissolved in DMSO and added to the tissue culture medium at the indicated concentrations; control cultures were treated with DMSO only. Several hours following treatment (as indicated in each experiment), cells were harvested and counted manually using a camera and standard inverted light microscope. Dead cells were excluded using Trypan Blue (Sigma). AnnexinV-PE (MBL), 7AAD (Tonbo) and PD-L1 (BioLegend) staining was evaluated by FACS according to manufacturer's recommendation.

Figure 6:
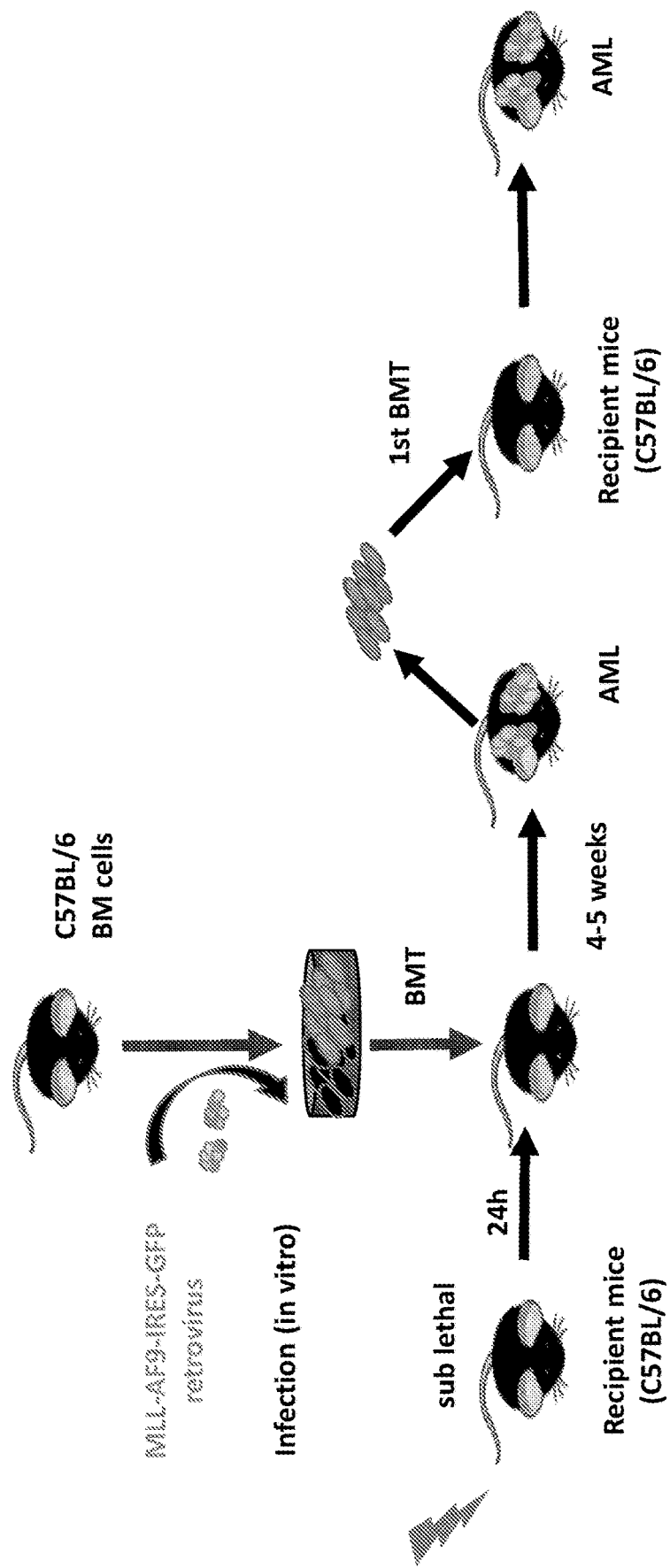
FIG. 6 shows a schematic representation of preparation of the AML mouse model.
Figure 8A:
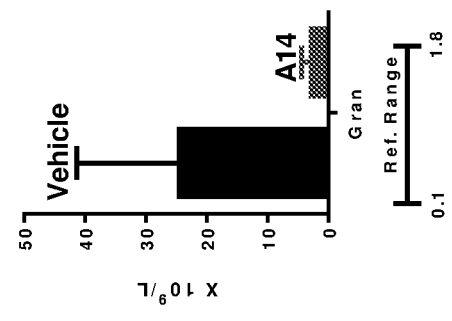
FIGS. 8A-8G show the complete blood count at day 9 after the treatment of AML mice with A14 of the invention.
Figure 8B:
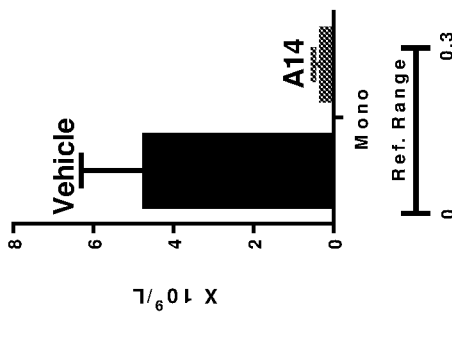
Figure 8C:
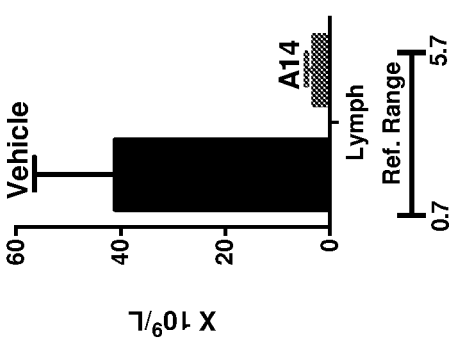
Figure 8D:
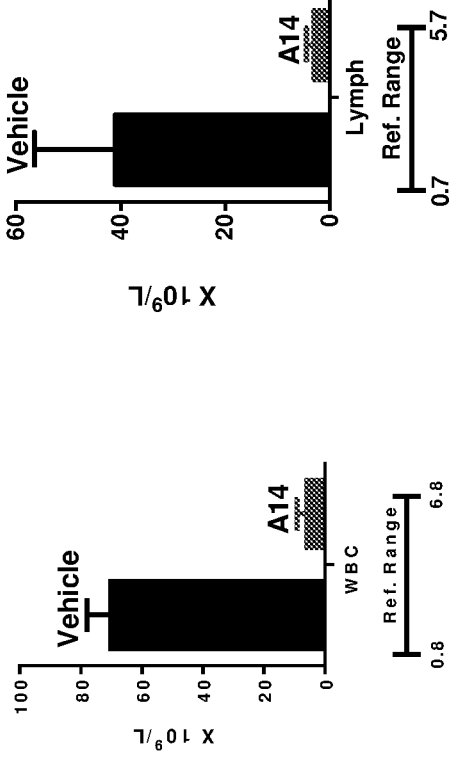
Figure 8E:
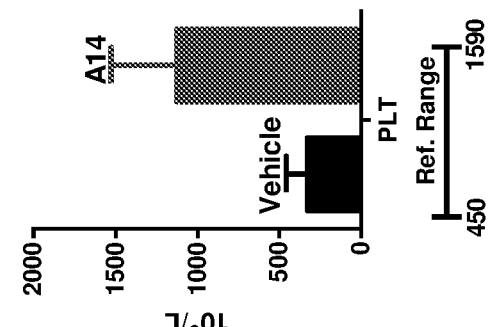
Figure 8F:
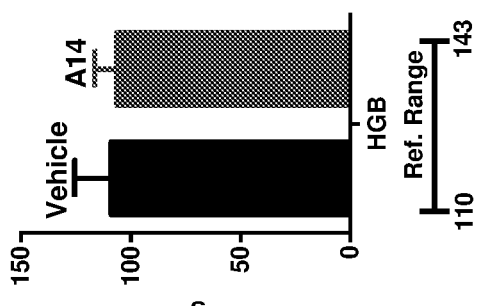
Figure 8G:
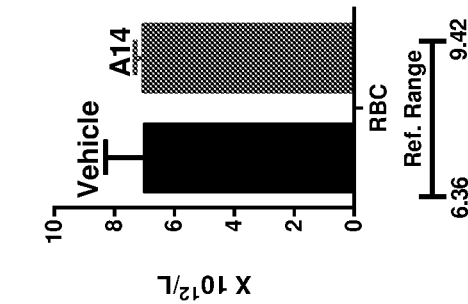
Figure 9:
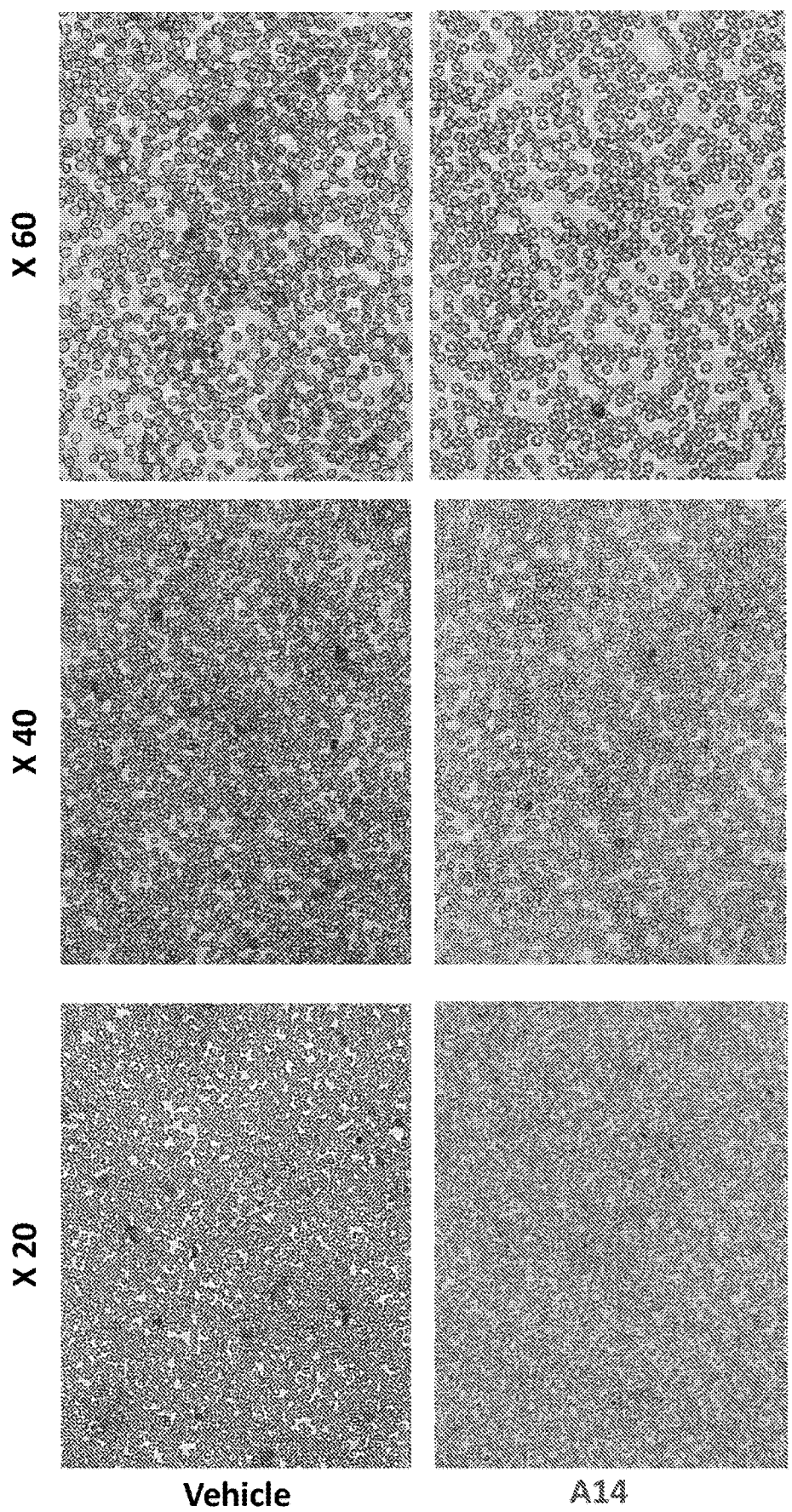
FIG. 9 shows representative photographs of blood smears from A14 compared to vehicle-treated AML mice at day 9 following the first A14 treatment.

Generation of a Mouse Model of Acute Myeloid Leukemia (AML) (FIG. 6) and Treatment with the CKIα Inhibitor A14 (FIGS. 7, 8 and 9) or A51 (FIGS. 11 and 12).

To generate the MLL-AF9 Acute myeloid leukemia (AML) model, bone marrow (BM) cells from 10 week old wild type mouse were extracted and enriched for cKit expressing cells (EasySep #18757) and incubated overnight in RPMI supplemented with 15% FCS L-Glutamine, Pen/Strep (Biological Industries, Israel) and stem cell factor (SCF), IL-3, IL-6 and TPO (Peprotech). The culture was infected with MSCV-MLL-AF9-IRES-GFP retrovirus construct containing supernatant medium for 4 hours, then growth medium was added and infected cells were incubated at 37° C. for additional 24 h. The culture was then injected I.V. into sub lethally irradiated (500 rad) mice. Upon detectable steady increase of GFP expressing cells in the mice peripheral blood (checked by FACS analysis) and rise in leukocyte numbers and immature cells (detected by Wright-Giemsa stained blood films), mice were sacrificed and their BM was transferred ($1^{st}$ BMT) to sublethally irradiated WT hosts. Upon emergence of AML disease mice were sacrificed and 50,000 BM cells were transplanted ($2^{nd}$ BMT) into WT host mice. GFP expressing cells were monitored in the peripheral blood and upon detecting >10% GFP$^+$ in PB (day 11 after BMT) mice were treated with A14 inhibitor (FIG. 7A). A14 was administered by oral gavage once a day at a dose of 20 mg/kg for 3 days followed by 10 mg/kg/day for 6 more days. The inhibitor was dissolved in 1% methyl cellulose with 0.1% Tween 80 and 0.2% Poly-ethylene glycol (Vehicle). Control mice were treated with the vehicle only. Mice were monitored daily for cachexia, lethargy, and ruff coats, and moribund mice were sacrificed. For a single dose experiment (FIG. 11A) A51 was administered by oral gavage at a single dose of 20 mg/kg and mice were sacrificed 16 hours following treatment.

FACS Analysis.

All assays were performed on BD's equipment: FACS caliber, FACS ARIA sorter or LSR II machines. For immunostaining, cells were suspended in a 1% BSA/PBS buffer with 5 µM EDTA. Cells were then analyzed by using Annexin V PE Apoptosis Detection Kit (eBioscience), 7-AAD (TONBO biosciences) and PE anti-mouse CD274 (B7-H1, PD-L1) antibody (clone 10F.9G2, BioLegend); Assays were performed according to the manufacturer's instruction. Monoclonal antibodies specific for CD16 and CD32 (Miltenyi Biotec) were used for blockade of Fc receptors before staining.

Complete Blood Counts.

Peripheral venous blood was obtained from the mouse facial vein using standard techniques and analyzed using the auto hematology analyzer BC-2800 (Mindray) per manufacturer's instructions.

Table 1 provides quantified information for compounds of the invention in activation of p53 and DNA damage response (DDR) and β-catenin stabilization as an indicator of Wnt pathway activation. p53 activation was determined according to the degree of protein stabilization in several Western blot assays (Western blot examples are shown in FIGS. 1A and 1B). For example, A43 stabilized p53 significantly above the non-treatment control at 6 µM with no activity at 2 µM (FIG. 1A, lower right panel) and thus received an average value of + for p53 activation. In contrast, A35 started stabilizing p53 at 0.2 µM, with maximal stabilization at 1 µM (FIG. 1A, upper right panel) and thus received an average value of +++ for p53 activation. A19-4, neither stabilized p53, nor induced γH2AX (a DNA damage response [DDR] indicator), but stabilized β-catenin at 2 µM, similarly to the best β-catenin stabilizing compounds (FIG. 1A, lower left panel) and thus received a value of +++ for β-catenin/Wnt activation.

TABLE 1 p53, DNA damage response and Wnt/β-catenin activation of compounds of the invention

| Compound | Structure | Name | Mass (M + H$^+$) | DDR & p53 activity | β-Catenin activity |
|---|---|---|---|---|---|
| A14 | 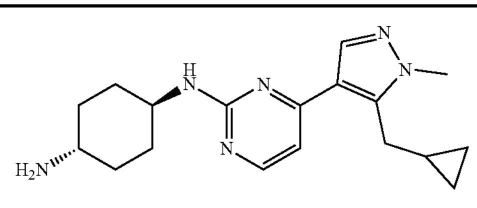 | (1R,4R)-N$^1$-(4-(5-(cyclopropyl methyl)-1-methyl-1H-pyrazol-4-yl)pyrimidin-2-yl)cyclohexane-1,4-diamine | Calc'd for $C_{18}H_{27}N_6$: 327.2; Found: 327.2 | +++ | ++ |

TABLE 1-continued p53, DNA damage response and Wnt/β-catenin activation of compounds of the invention

| Compound | Name | Mass (M + H+) | DDR & p53 activity | β-Catenin activity |
|---|---|---|---|---|
| A29-1 | N-((1R,4R)-4-((4-(5-(cyclopropylmethyl)-1-methyl-1H-pyrazol-4-yl)pyrimidin-2-yl)amino)cyclohexyl)-2-methoxyacetamide | Calc'd for $C_{21}H_{31}N_6O2$: 399.2; Found: 399.2 | ++ | NA |
| A27 | (1R,4R)-$N^1$-(4-(5-(cyclopropylmethyl)-1-methyl-1H-pyrazol-4-yl)pyrimidin-2-yl)-$N^4$-methylcyclohexane-1,4-diamine | Calc'd for $C_{19}H_{29}N_6$: 341.2.; Found: 341.2 | ++ | ++ |
| A28 | (1R,4R)-$N^1$-(4-(5-(cyclopropylmethyl)-1-methyl-1H-pyrazol-4-yl)pyrimidin-2-yl)-$N^4$,$N^4$-dimethylcyclohexane-1,4-diamine | Calc'd for $C_{20}H_{31}N_6$: 355.3; Found: 355.2 | ++ | +++ |
| A36 | (1R,4R)-$N^1$-(4-(1-cyclopentyl-5-(cyclopropylmethyl)-1H-pyrazol-4-yl)pyrimidin-2-yl)cyclohexane-1,4-diamine | Calc'd for $C_{22}H_{33}N_6$: 381.3; Found: 381.4 | ++ | NA |
| A39 | (1R,4R)-$N^1$-(4-(5-(cyclopropylmethyl)-1-(tetrahydro-2H-pyran-4-yl)-1H-pyrazol-4-yl)pyrimidin-2-yl)cyclohexane-1,4-diamine | Calc'd for $C_{22}H_{33}N_6O$: 397.3; Found: 397.4 | ++ | NA |
| A29 | (1R,4R)-$N^1$-(4-(5-(cyclopropylmethyl)-1-methyl-1H-pyrazol-4-yl)pyrimidin-2-yl)-$N^4$-(2-methoxyethyl)cyclohexane-1,4-diamine | Calc'd for $C_{21}H_{33}N_6O$: 385.3; Found: 385.2 | ++ | NA |

TABLE 1-continued p53, DNA damage response and Wnt/β-catenin activation of compounds of the invention

| Compound | Structure | Name | Mass (M + H+) | DDR & p53 activity | β-Catenin activity |
|---|---|---|---|---|---|
| A19-4 | 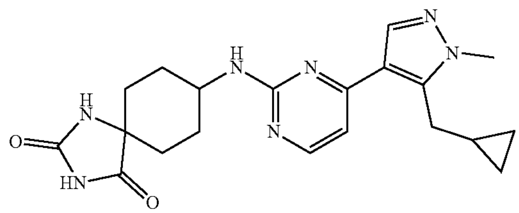 | 8-((4-(5-(cyclopropyl-methyl)-1-methyl-1H-pyrazol-4-yl)pyrimidin-2-yl)amino)-1,3-diazaspiro[4.5]decane-2,4-dione | Calc'd for $C_{20}H_{26}N_7O_2$: 396.2; Found: 396.2 | NA | +++ |
| A35 | 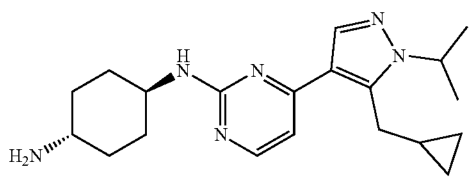 [SMILES: CC(C)n1ncc(-c2ccnc(N[C@H]3CC[C@H](N)CC3)n2)c1CC1CC1] | (1R,4R)-N1-(4-(5-(cyclopropyl-methyl)-1-isopropyl-1H-pyrazol-4-yl)pyrimidin-2-yl)cyclohexane-1,4-diamine | Calc'd for $C_{20}H_{31}N_6$: 355.3; Found: 355.3 | +++ | ++ |
| A41 | 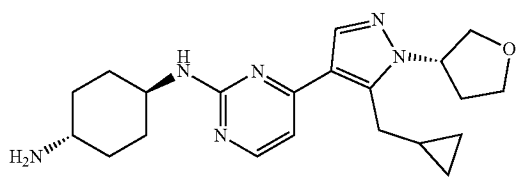 [SMILES: N[C@H]1CC[C@H](Nc2nccc(-c3cnn([C@H]4CCOC4)c3CC3CC3)n2)CC1] | (1r,4S)-N1-(4-(5-(cyclopropyl-methyl)-1-((S)-tetrahydrofuran-3-yl)-1H-pyrazol-4-yl)pyrimidin-2-yl)cyclohexane-1,4-diamine | Calc'd for $C_{21}H_{31}N_6O$: 383.3; Found: 383.3 | ++ | NA |
| A42 | 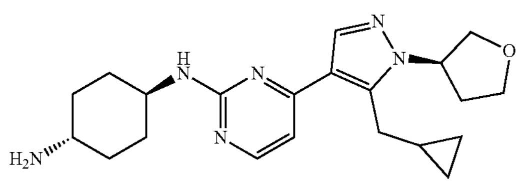 [SMILES: N[C@H]1CC[C@H](Nc2nccc(-c3cnn([C@@H]4CCOC4)c3CC3CC3)n2)CC1] | (1R,4R)-N1-(4-(5-(cyclopropyl-methyl)-1-((R)-tetrahydrofuran-3-yl)-1H-pyrazol-4-yl)pyrimidin-2-yl)cyclohexane-1,4-diamine | Calc'd for $C_{21}H_{31}N_6O$: 383.3; Found: 383.2 | ++ | NA |
| A43 | 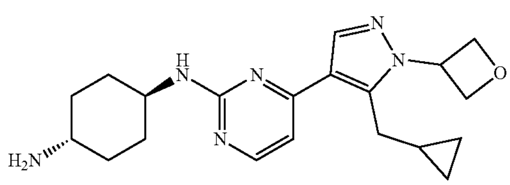 [SMILES: N[C@H]1CC[C@H](Nc2nccc(-c3cnn(C4COC4)c3CC3CC3)n2)CC1] | (1R,4R)-N1-(4-(5-(cyclopropyl-methyl)-1-(oxetan-3-yl)-1H-pyrazol-4-yl)pyrimidin-2-yl)cyclohexane-1,4-diamine | Calc'd for $C_{20}H_{29}N_6O$: 369.2; Found: 369.3 | + | NA |
| A46 | 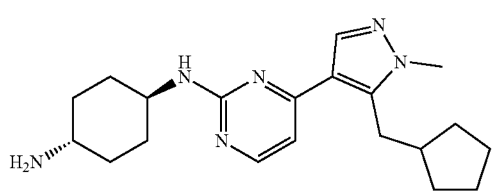 [SMILES: Cn1ncc(-c2ccnc(N[C@H]3CC[C@H](N)CC3)n2)c1CC1CCCC1] | (1R,4R)-N1-(4-(5-(cyclopentyl-methyl)-1-methyl-1H-pyrazol-4-yl)pyrimidin-2-yl)cyclohexane-1,4-diamine | Calc'd for $C_{20}H_{31}N_6$: 355.3; Found: 355.2 | ++ | NA |
| A38 | 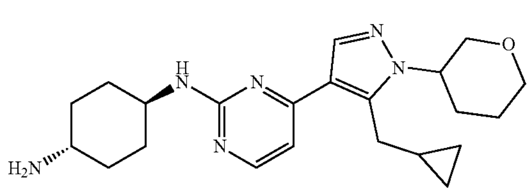 [SMILES: N[C@H]1CC[C@H](Nc2nccc(-c3cnn(C4CCCOC4)c3CC3CC3)n2)CC1] | (1R,4R)-N1-(4-(5-(cyclopropyl-methyl)-1-(tetrahydro-2H-pyran-3-yl)-1H-pyrazol-4-yl)pyrimidin-2-yl)cyclohexane-1,4-diamine | Calc'd for $C_{22}H_{33}N_6O$: 397.3; Found: 397.3 | + | + |

TABLE 1-continued p53, DNA damage response and Wnt/β-catenin activation of compounds of the invention

| Compound | Structure | Name | Mass (M + H⁺) | DDR & p53 activity | β-Catenin activity |
|---|---|---|---|---|---|
| A45 | 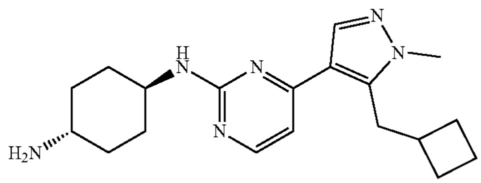 [SMILES: Cn1ncc(-c2ccnc(N[C@H]3CC[C@H](N)CC3)n2)c1CC1CCC1] | (1R,4R)-N1-(4-(5-(cyclobutyl-methyl)-1-methyl-1H-pyrazol-4-yl)pyrimidin-2-yl)cyclohexane-1,4-diamine | Calc'd for $C_{19}H_{29}N_6$: 341.2; Found: 341.3 | ++ | + |
| A19 | 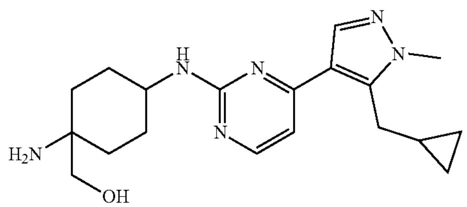 [SMILES: Cn1ncc(-c2ccnc(NC3CCC(N)(CO)CC3)n2)c1CC1CC1] | (1-amino-4-((4-(5-(cyclopropyl-methyl)-1-methyl-1H-pyrazol-4-yl)pyrimidin-2-yl)amino)cyclo-hexyl)methanol | Calc'd for $C_{19}H_{29}N_6O$: 357.2; Found: 357.2 | + | + |
| A26 | 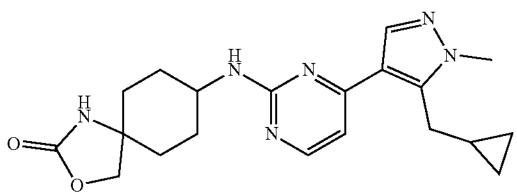 [SMILES: Cn1ncc(-c2ccnc(NC3CCC4(CC3)COC(=O)N4)n2)c1CC1CC1] | 8-((4-(5-(cyclopropyl-methyl)-1-methyl-1H-pyrazol-4-yl)pyrimidin-2-yl)amino)-3-oxa-1-azaspiro[4.5]decan-2-one | Calc'd for $C_{20}H_{27}N_6O_2$: 383.2; Found: 383.2 | + | + |
| A47 | 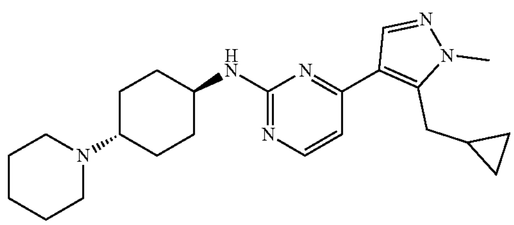 [SMILES: Cn1ncc(-c2ccnc(N[C@H]3CC[C@H](N4CCCCC4)CC3)n2)c1CC1CC1] | 4-(5-(cyclopropyl-methyl)-1-methyl-1H-pyrazol-4-yl)-N-((1R,4R)-4-(piperidin-1-yl)cyclohexyl)pyrimidin-2-amine | Calc'd for $C_{23}H_{35}N_6$: 395.3; Found: 395.2 | ++ | + |
| A48 | 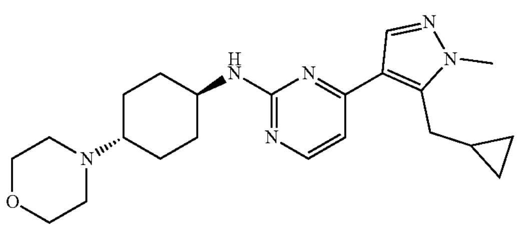 [SMILES: Cn1ncc(-c2ccnc(N[C@H]3CC[C@H](N4CCOCC4)CC3)n2)c1CC1CC1] | 4-(5-(cyclopropyl-methyl)-1-methyl-1H-pyrazol-4-yl)-N-((1R,4R)-4-morpholino-cyclohexyl)pyrimidin-2-amine | Calc'd for $C_{22}H_{33}N_6O$: 397.3; Found: 397.3 | + | + |
| A49 | 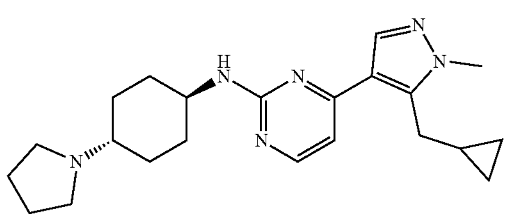 [SMILES: Cn1ncc(-c2ccnc(N[C@H]3CC[C@H](N4CCCC4)CC3)n2)c1CC1CC1] | 4-(5-(cyclopropyl-methyl)-1-methyl-1H-pyrazol-4-yl)-N-((1R,4R)-4-(pyrrolidin-1-yl)cyclohexyl)pyrimidin-2-amine | Calc'd for $C_{22}H_{33}N_6$: 381.3; Found: 381.3 | + | NA |
| A50 | 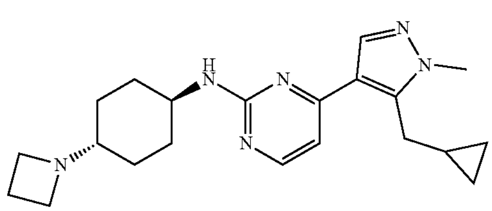 [SMILES: Cn1ncc(-c2ccnc(N[C@H]3CC[C@H](N4CCC4)CC3)n2)c1CC1CC1] | N-((1R,4R)-4-(azetidin-1-yl)cyclohexyl)-4-(5-(cyclopropyl-methyl)-1-methyl-1H-pyrazol-4-yl)pyrimidin-2-amine | Calc'd for $C_{21}H_{31}N_6$: 367.3; Found: 367.3 | +++ | ++ |

TABLE 1-continued p53, DNA damage response and Wnt/β-catenin activation of compounds of the invention

| Compound | Structure | Name | Mass (M + H+) | DDR & p53 activity | β-Catenin activity |
|---|---|---|---|---|---|
| A51 | 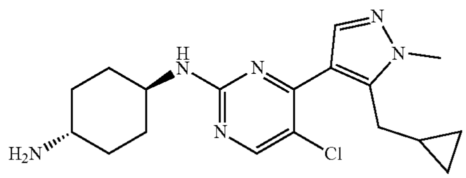 [SMILES: Cn1ncc(-c2nc(N[C@H]3CC[C@H](N)CC3)ncc2Cl)c1CC1CC1] | (1R,4R)-N1-(5-chloro-4-(5-(cyclopropylmethyl)-1-methyl-1H-pyrazol-4-yl)pyrimidin-2-yl)cyclohexane-1,4-diamine | Calc'd for $C_{18}H_{26}ClN_6$: 361.2; Found: 361.1 | ++++ | +++ |
| A52 | 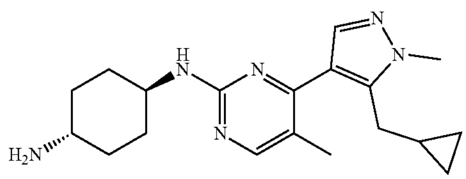 [SMILES: Cc1cnc(N[C@H]2CC[C@H](N)CC2)nc1-c1cnn(C)c1CC1CC1] | (1R,4R)-N1-(4-(5-(cyclopropylmethyl)-1-methyl-1H-pyrazol-4-yl)-5-methylpyrimidin-2-yl)cyclohexane-1,4-diamine | Calc'd for $C_{19}H_{29}N_6$: 341.2; Found: 341.2 | ++ | NA |
| A53 | 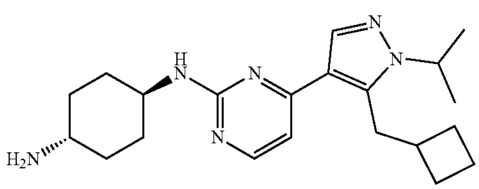 [SMILES: CC(C)n1ncc(-c2ccnc(N[C@H]3CC[C@H](N)CC3)n2)c1CC1CCC1] | (1R,4R)-N1-(4-(5-(cyclobutylmethyl)-1-isopropyl-1H-pyrazol-4-yl)pyrimidin-2-yl)cyclohexane-1,4-diamine | Calc'd for $C_{21}H_{33}N_6$: 369.3; Found: 369.2 | + | + |
| A58 | 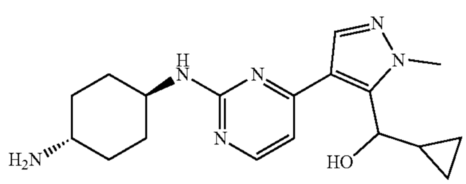 [SMILES: Cn1ncc(-c2ccnc(N[C@H]3CC[C@H](N)CC3)n2)c1C(O)C1CC1] | (4-(2-(((1R,4R)-4-aminocyclohexyl)amino)pyrimidin-4-yl)-1-methyl-1H-pyrazol-5-yl)(cyclopropyl)methanol | Calc'd for $C_{18}H_{27}N_6O$: 343.2; Found: 343.2 | + | NA |
| A59 | 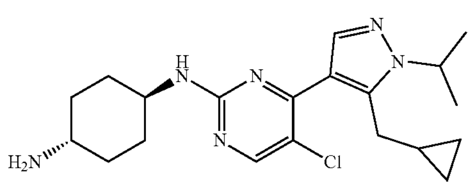 [SMILES: CC(C)n1ncc(-c2nc(N[C@H]3CC[C@H](N)CC3)ncc2Cl)c1CC1CC1] | (1R,4R)-N¹-(5-chloro-4-(5-(cyclopropylmethyl)-1-isopropyl-1H-pyrazol-4-yl)pyrimidin-2-yl)cyclohexane-1,4-diamine | Calc'd for $C_{20}H_{30}ClN_6$: 389.2; Found: 389.2 | +++ | ++ |
| A56 | 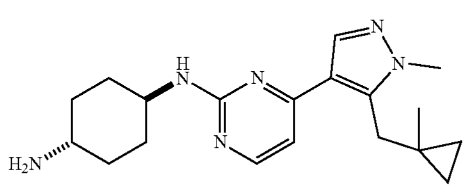 [SMILES: Cn1ncc(-c2ccnc(N[C@H]3CC[C@H](N)CC3)n2)c1CC1(C)CC1] | (1R,4R)-N¹-(4-(1-methyl-5-((1-methylcyclopropyl)methyl)-1H-pyrazol-4-yl)pyrimidin-2-yl)cyclohexane-1,4-diamine | Calc'd for $C_{19}H_{29}N_6$: 341.2; Found: 341.2 | ++ | NA |
| A57 | 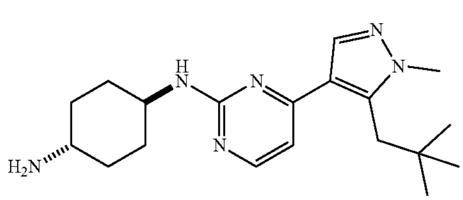 [SMILES: Cn1ncc(-c2ccnc(N[C@H]3CC[C@H](N)CC3)n2)c1CC(C)(C)C] | (1R,4R)-N¹-(4-(1-methyl-5-neopentyl-1H-pyrazol-4-yl)pyrimidin-2-yl)cyclohexane-1,4-diamine | Calc'd for $C_{19}H_{31}N_6$: 343.3; Found: 343.2 | NA | NA |

TABLE 1-continued p53, DNA damage response and Wnt/β-catenin activation of compounds of the invention

| Compound | Structure | Name | Mass (M + H+) | DDR & p53 activity | β-Catenin activity |
|---|---|---|---|---|---|
| A30-1 | 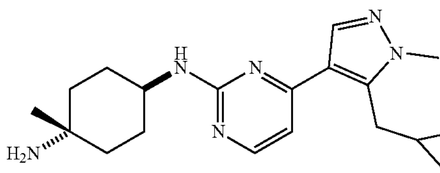 | (1R,4R)-N$^1$-(5-chloro-4-(5-(cyclopropyl-methyl)-1-methyl-1H-pyrazol-4-yl)pyrimidin-2-yl)-4-methylcyclo-hexane-1,4-diamine | Calc'd for C$_{19}$H$_{28}$ClN$_6$: 375.2; Found: 375.2 | ++++ | ++ |
| A30-2 | 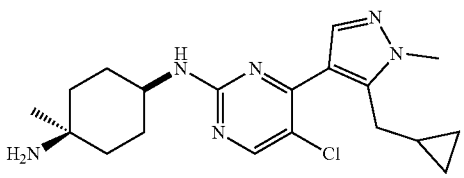 [SMILES: Cn1ncc(-c2nc(N[C@H]3CC[C@@](C)(N)CC3)ncc2Cl)c1CC1CC1] | (1s,4s)-N1-(5-chloro-4-(5-(cyclopropyl-methyl)-1-methyl-1H-pyrazol-4-yl)pyrimidin-2-yl)-4-methylcyclo-hexane-1,4-diamine | Calc'd for C$_{19}$H$_{28}$ClN$_6$: 375.2; Found: 375.2 | ++ | ++ |
| A60 | 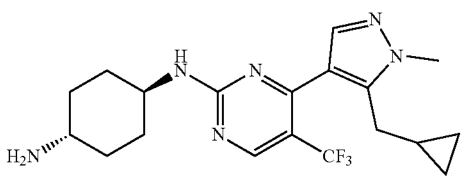 [SMILES: Cn1ncc(-c2nc(N[C@H]3CC[C@H](N)CC3)ncc2C(F)(F)F)c1CC1CC1] | (1R,4R)-N$^1$-(4-(5-(cyclopropyl-methyl)-1-methyl-1H-pyrazol-4-yl)-5-(trifluoromethyl)pyrimidin-2-yl)cyclohexane-1,4-diamine | Calc'd for C$_{19}$H$_{26}$F$_3$N$_6$: 395.2; Found: 395.2 | ++ | +/− |
| A64 | 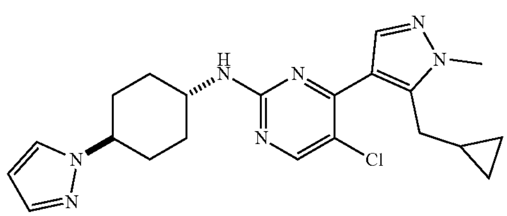 [SMILES: Cn1ncc(-c2nc(N[C@H]3CC[C@H](n4cccn4)CC3)ncc2Cl)c1CC1CC1] | N-((1R,4R)-4-(1H-pyrazol-1-yl)cyclohexyl)-5-chloro-4-(5-(cyclopropyl-methyl)-1-methyl-1H-pyrazol-4-yl)pyrimidin-2-amine | Calc'd for C$_{21}$H$_{27}$ClN$_7$: 412.2; Found: 412.2 | + | ++ |
| A65 | 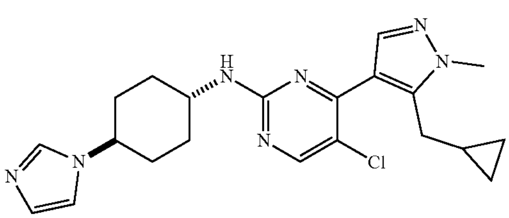 [SMILES: Cn1ncc(-c2nc(N[C@H]3CC[C@H](n4ccnc4)CC3)ncc2Cl)c1CC1CC1] | N-((1R,4R)-4-(1H-imidazol-1-yl)cyclohexyl)-5-chloro-4-(5-(cyclopropyl-methyl)-1-methyl-1H-pyrazol-4-yl)pyrimidin-2-amine | Calc'd for C$_{21}$H$_{27}$ClN$_7$: 412.2; Found: 412.2 | ++ | ++ |
| A68 | 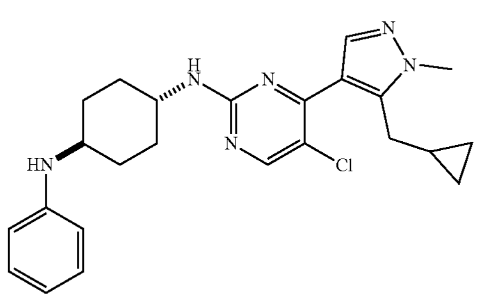 [SMILES: Cn1ncc(-c2nc(N[C@H]3CC[C@H](Nc4ccccc4)CC3)ncc2Cl)c1CC1CC1] | (1R,4R)-N$^1$-(5-chloro-4-(5-(cyclopropyl-methyl)-1-methyl-1H-pyrazol-4-yl)pyrimidin-2-yl)-N$^4$-phenylcyclohexane-1,4-diamine | Calc'd for C$_{24}$H$_{30}$ClN$_6$: 437.2; Found: 437.2 | + | + |

TABLE 1-continued p53, DNA damage response and Wnt/β-catenin activation of compounds of the invention

| Compound | Structure | Name | Mass (M + H+) | DDR & p53 activity | β-Catenin activity |
|---|---|---|---|---|---|
| A71 | 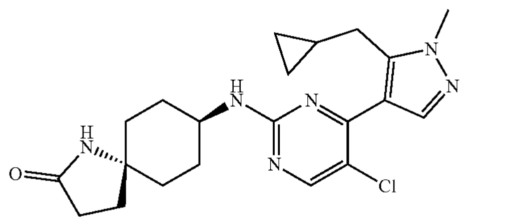 [SMILES: Cn1ncc(-c2nc(N[C@H]3CC[C@@]4(CCC(=O)N4)CC3)ncc2Cl)c1CC1CC1] | (5r,8r)-8-((5-chloro-4-(5-(cyclopropyl-methyl)-1-methyl-1H-pyrazol-4-yl)pyrimidin-2-yl)amino)-1-azaspiro[4.5]decan-2-one | Calc'd for $C_{21}H_{28}ClN_6O$: 415.2; Found: 415.2 | NA | ++ |
| A74 | 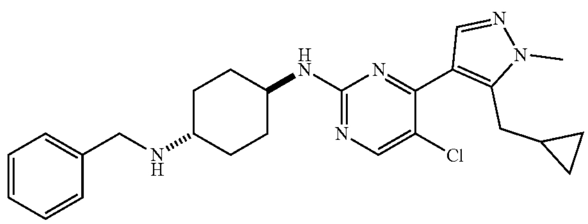 [SMILES: Cn1ncc(-c2nc(N[C@H]3CC[C@H](NCc4ccccc4)CC3)ncc2Cl)c1CC1CC1] | (1R,4R)-$N^1$-benzyl-$N^4$-(5-chloro-4-(5-(cyclopropyl-methyl)-1-methyl-1H-pyrazol-4-yl)pyrimidin-2-yl)cyclohexane-1,4-diamine | Calc'd for $C_{25}H_{32}ClN_6$: 451.2; Found: 451.2 | +++ | ++ |
| A75 | 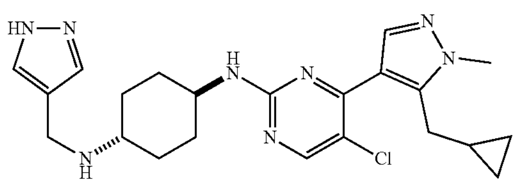 [SMILES: Cn1ncc(-c2nc(N[C@H]3CC[C@H](NCc4cn[nH]c4)CC3)ncc2Cl)c1CC1CC1] | (1R,4R)-$N^1$-((1H-pyrazol-4-yl)methyl)-$N^4$-(5-chloro-4-(5-(cyclopropyl-methyl)-1-methyl-1H-pyrazol-4-yl)pyrimidin-2-yl)cyclohexane-1,4-diamine | Calc'd for $C_{22}H_{30}ClN_8$: 441.2; Found: 441.2 | +++++ | +++ |
| A76 | 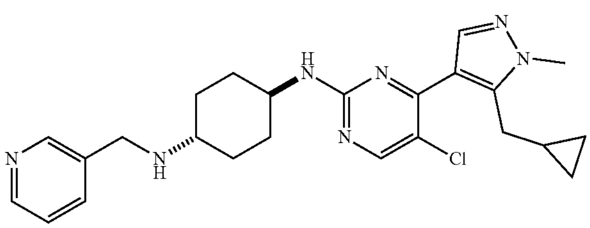 [SMILES: Cn1ncc(-c2nc(N[C@H]3CC[C@H](NCc4cccnc4)CC3)ncc2Cl)c1CC1CC1] | (1R,4R)-$N^1$-(5-chloro-4-(5-(cyclopropyl-methyl)-1-methyl-1H-pyrazol-4-yl) pyrimidin-2-yl)-$N^4$-(pyridin-3-ylmethyl)cyclohexane-1,4-diamine | Calc'd for $C_{24}H_{31}ClN_7$: 452.2; Found: 452.2 | +++ | ++ |
| A80 | 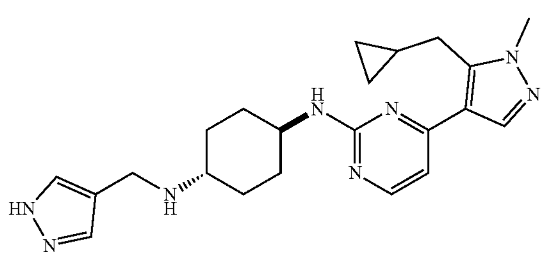 [SMILES: Cn1ncc(-c2ccnc(N[C@H]3CC[C@H](NCc4cn[nH]c4)CC3)n2)c1CC1CC1] | (1r, 4r)-$N^1$-((1H-pyrazol-4-yl)methyl)-$N^4$-(4-(5-(cyclopropyl-methyl)-1-methyl-1H-pyrazol-4-yl)pyrimidin-2-yl)cyclohexane-1,4-diamine | Calc'd for $C_{22}H_{31}N_8$: 407.3; Found: 407.2 | ++ | NA |
| A81 | 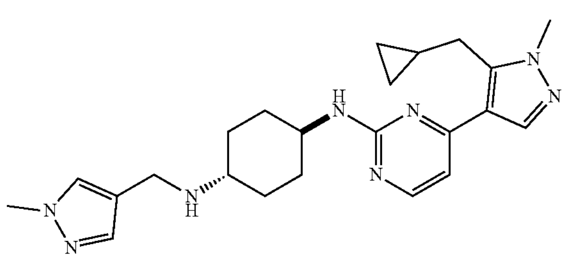 [SMILES: Cn1cc(CN[C@H]2CC[C@H](Nc3nccc(-c4cnn(C)c4CC4CC4)n3)CC2)cn1] | (1R,4R)-$N^1$-((1H-pyrazol-3-yl)methyl)-$N^4$-(5-chloro-4-(5-(cyclopropyl-methyl)-1-methyl-1H-pyrazol-4-yl)pyrimidin-2-yl)cyclohexane-1,4-diamine | Calc'd for $C_{23}H_{33}N_8$: 421.3; Found: 421.2 | ++ | NA |

TABLE 1-continued p53, DNA damage response and Wnt/β-catenin activation of compounds of the invention

| Com-pound | Structure | Name | Mass (M + H⁺) | DDR & p53 activity | β-Catenin activity |
|---|---|---|---|---|---|
| A82 | 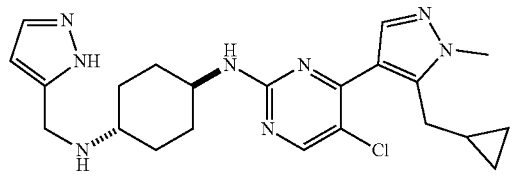 [SMILES: Cn1ncc(-c2nc(N[C@H]3CC[C@H](NCc4ccn[nH]4)CC3)ncc2Cl)c1CC1CC1] | (1R,4R)-N$^1$-((1H-pyrazol-3-yl)methyl)-N$^4$-(5-chloro-4-(5-(cyclopropyl methyl)-1-methyl-1H-pyrazol-4-yl)pyrimidin-2-yl)cyclohexane-1,4-diamine | Calc'd for $C_{22}H_{30}ClN_8$: 441.2; Found: 441.2 | +++ | ++ |
| A83 | 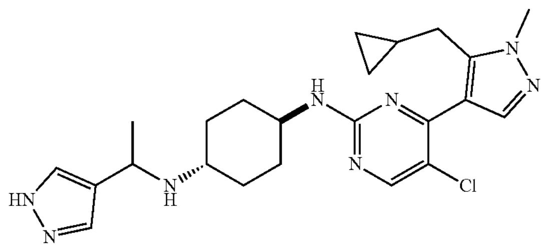 [SMILES: CC(N[C@H]1CC[C@H](Nc2ncc(Cl)c(-c3cnn(C)c3CC3CC3)n2)CC1)c1cn[nH]c1] | (1R,4R)-N$^1$-(1-(1H-pyrazol-4-yl)ethyl)-N$^4$-(5-chloro-4-(5-(cyclopropyl-methyl)-1-methyl-1H-pyrazol-4-yl)pyrimidin-2-yl)cyclohexane-1,4-diamine | Calc'd for $C_{23}H_{32}ClN_8$: 455.2; Found: 455.2 | ++ | ++ |
| A87 | 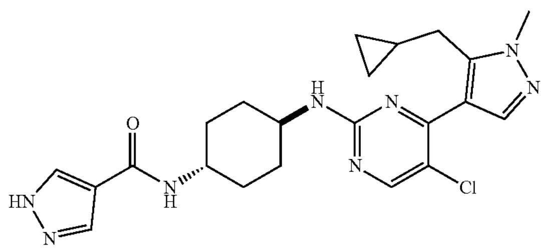 [SMILES: Cn1ncc(-c2nc(N[C@H]3CC[C@H](NC(=O)c4cn[nH]c4)CC3)ncc2Cl)c1CC1CC1] | N-((1R,4R)-4-((5-chloro-4-(5-(cyclopropyl-methyl)-1-methyl-1H-pyrazol-4-yl)pyrimidin-2-yl)amino)cyclo-hexyl)-1H-pyrazole-4-carboxamide | Calc'd for $C_{22}H_{28}ClN_8O$: 455.2; Found: 455.2 | + | +++ |
| A91 | 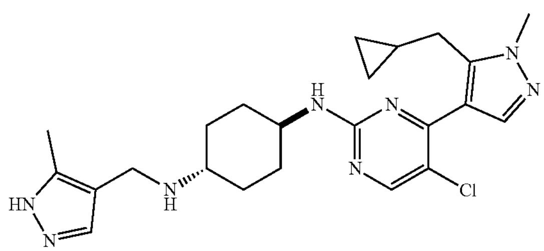 [SMILES: Cc1[nH]ncc1CN[C@H]1CC[C@H](Nc2ncc(Cl)c(-c3cnn(C)c3CC3CC3)n2)CC1] | (1R,4R)-N$^1$-(5-chloro-4-(5-(cyclopropyl-methyl)-1-methyl-1H-pyrazol-4-yl)pyrimidin-2-yl)-N$^4$-((5-methyl-1H-pyrazol-4-yl)methyl)cyclo hexane-1,4-diamine | Calc'd for $C_{23}H_{32}ClN_8$: 455.2; Found: 455.2 | +++ | ++ |
| A94 | 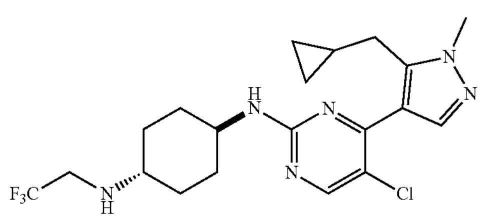 [SMILES: Cn1ncc(-c2nc(N[C@H]3CC[C@H](NCC(F)(F)F)CC3)ncc2Cl)c1CC1CC1] | (1R,4R)-N$^1$-(5-chloro-4-(5-(cyclopropyl-methyl)-1-methyl-1H-pyrazol-4-yl)pyrimidin-2-yl)-N$^4$-(2,2,2-trifluoroethyl)cyclohexane-1,4-diamine | Calc'd for $C_{20}H_{27}ClF_3N_6$: 443.2; Found: 443.2 | + | ++ |
| A95 | 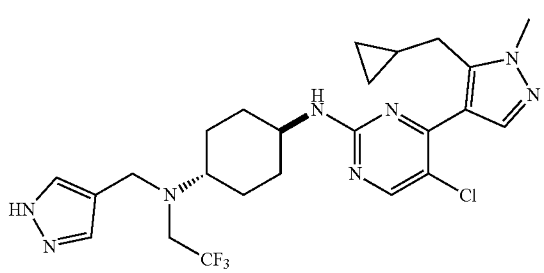 [SMILES: Cn1ncc(-c2nc(N[C@H]3CC[C@H](N(Cc4cn[nH]c4)CC(F)(F)F)CC3)ncc2Cl)c1CC1CC1] | (1R,4R)-N$^1$-((1H-pyrazol-4-yl)methyl)-N$^4$-(5-chloro-4-(5-(cyclopropyl methyl)-1-methyl-1H-pyrazol-4-yl)pyrimidin-2-yl)-N$^1$-(2,2,2-trifluoroethyl)cyclohexane-1,4-diamine | Calc'd for $C_{24}H_{31}ClF_3N_6$: 523.2; Found: 523.2 | +++ | ++ |

TABLE 1-continued p53, DNA damage response and Wnt/β-catenin activation of compounds of the invention

| Compound | Structure | Name | Mass (M + H+) | DDR & p53 activity | β-Catenin activity |
|---|---|---|---|---|---|
| A96 | 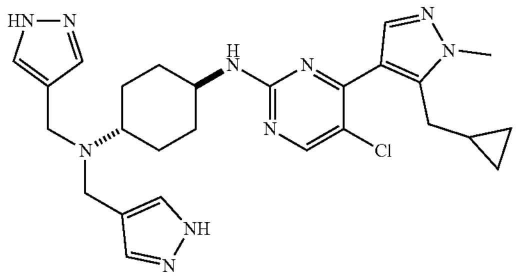 [SMILES: Cn1ncc(-c2nc(N[C@H]3CC[C@H](N(Cc4cn[nH]c4)Cc4cn[nH]c4)CC3)ncc2Cl)c1CC1CC1] | (1R,4R)-N$^1$,N$^1$-bis((1H-pyrazol-4-yl)methyl)-N$^4$-(5-chloro-4-(5-(cyclopropyl-methyl)-1-methyl-1H-pyrazol-4-yl)pyrimidin-2-yl)cyclohexane-1,4-diamine | Calc'd for C$_{26}$H$_{34}$ClN$_{10}$: 521.3; Found: 521.3 | NA | NA |
| A86 | 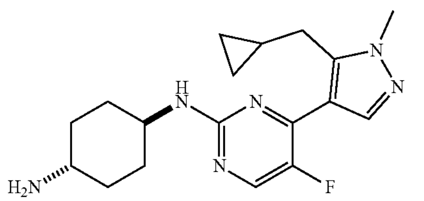 [SMILES: Cn1ncc(-c2nc(N[C@H]3CC[C@H](N)CC3)ncc2F)c1CC1CC1] | (1R,4R)-N$^1$-(4-(5-(cyclopropyl-methyl)-1-methyl-1H-pyrazol-4-yl)-5-fluoropyrimidin-2-yl)cyclohexane-1,4-diamine | Calc'd for C$_{18}$H$_{26}$FN$_6$: 345.2; Found: 345.2 | +++++ | +++ |
| A85 | 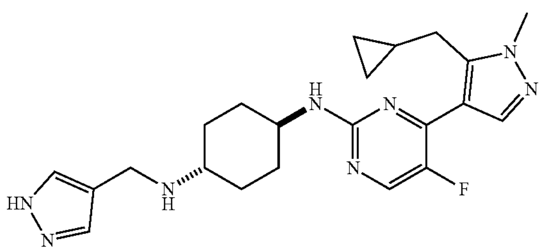 [SMILES: Cn1ncc(-c2nc(N[C@H]3CC[C@H](NCc4cn[nH]c4)CC3)ncc2F)c1CC1CC1] | (1R,4R)-N$^1$-((1H-pyrazol-4-yl)methyl)-N$^4$-(4-(5-(cyclopropyl-methyl)-1-methyl-1H-pyrazol-4-yl)-5-fluoropyrimidin-2-yl)cyclohexane-1,4-diamine | Calc'd for C$_{22}$H$_{30}$FN$_6$: 425.3; Found: 425.3 | +++ | +++ |

+ indicates low, yet significant activation at a compound concentration of 6 μM;
+++ indicates maximal β-catenin or p53 stabilization at >2 μM;
++++ indicates maximal activation of p53 and DDR at >0.5 μM,
+++++ indicates maximal activation of p53 and DDR at >0.1 μM.

IRAK1 Inhibition with Compounds of the Invention.

Figure 10:
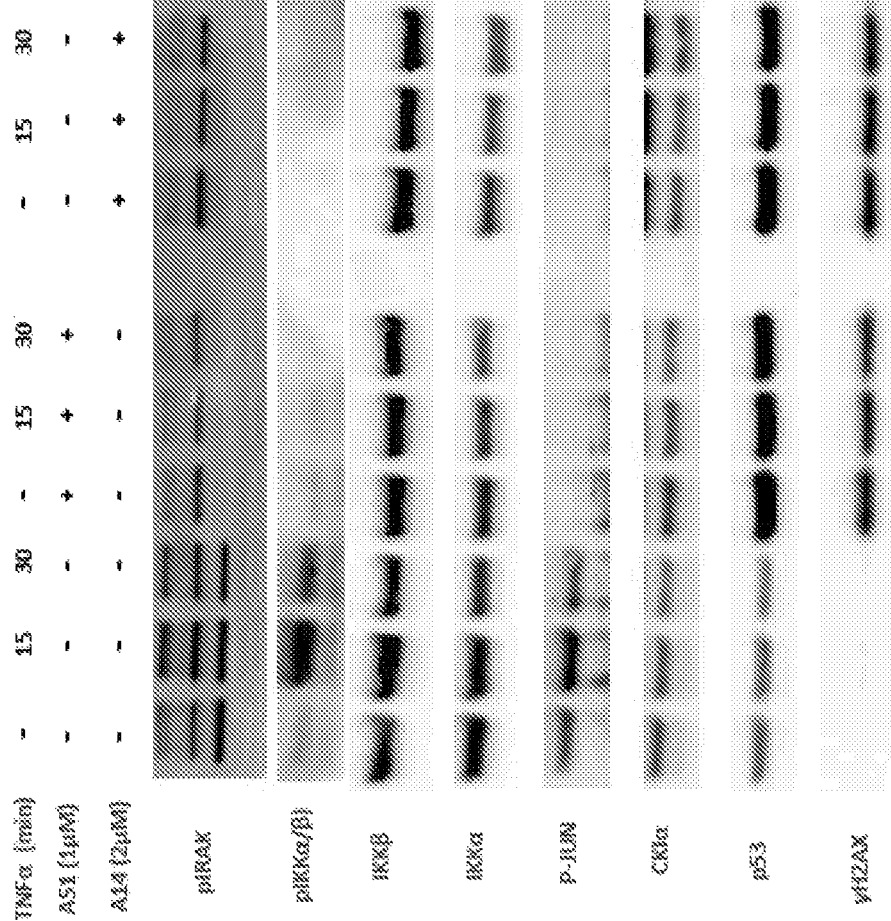
FIG. 10 shows IRAK1 inhibition by the inhibitor compounds of the invention, A51 and A14. Cells were harvested and analyzed by Western blot. Blots were incubated with the following antibodies: Phospho-IRAK1 (Thr209), (A1074, AssayBiothechnology; 1/1,000), Phospho-IKKα/β (Ser176/180) (16A6, Cell Signaling; 1/1,000), IKKα (2682, cell signaling; 1/1,1000), IKK β (2370, cell signaling; 1/1,1000), Phospho-c-Jun (Ser 63) (9261, cell signaling; 1/1,1000), p53 (DO-1&1801 hybridoma mix; dilution of 1:20 of supernatants from each), CKIα (C-19; 1/1,000; Santa Cruz Biotechnology) and phospho-histoneH2AX (S139; 1/1,000; Millipore). Secondary antibodies were HRP-linked goat anti-mouse, goat anti-rabbit and rabbit anti-goat antibodies (all 1/10,000; Jackson). Inhibition of Phospho-IRAK1, Phospho-IKKα/β and Phospho-c-Jun indicate IRAK1 inhibition. p53 stabilization and phosphorylation of H2AX (γH2AX), a marker of DNA damage, indicative of CKIα kinase inhibition. CKIα protein levels serves as a loading control.

RKO cells were incubated for 16 hours at 37° C. with the indicated concentrations of compounds of the invention A51 (1 μM) and A14 (2 μM) (FIG. 10). At the indicated time points, RKO were treated with TNFα (100 units/ml). Cells were harvested and analyzed by Western blot. Blots were incubated with the following antibodies: Phospho-IRAK1 (Thr209), (A1074, AssayBiothechnology; 1/1,000), Phospho-IKKα/β (Ser176/180) (16A6, Cell Signaling; 1/1,000), IKKα (2682, cell signaling; 1/1,1000), IKK β (2370, cell signaling; 1/1,1000), Phospho-c-Jun (Ser 63) (9261, cell signaling; 1/1,1000), p$^{53}$ (DO-1&1801 hybridoma mix; dilution of 1:20 of supernatants from each), CKIα (C-19; 1/1,000; Santa Cruz Biotechnology) and phospho-histoneH2AX (S139; 1/1,000; Millipore). Secondary antibodies were HRP-linked goat anti-mouse, goat anti-rabbit and rabbit anti-goat antibodies (all 1/10,000; Jackson). Blots were developed using ECL (GE Healthcare).

FIG. 10, shows the inhibition of phosphorylation of IRAK1 as well as Phospho-IKKα/β and Phospho-c-Jun, indicative of IRAK1 kinase Inhibition. Also shown is p53 stabilization and phosphorylation of H2AX (γH2AX), a marker of DNA damage, indicative of CKIα kinase inhibition. CKIα protein levels serves as a loading control. Kinome affinity scan for A51 (WXL5846, see Table 2 below), shows that the key targets of A51 includes the entire CKI family members and IRAK1, with a few control kinases. KINOMEscan™ is based on a competition binding assay that quantitatively measures the ability of a compound to compete with an immobilized, active-site directed ligand. The assay is performed by combining three components: DNA-tagged kinase; immobilized ligand; and a test compound. The ability of the test compound to compete with the immobilized ligand is measured via quantitative PCR of the DNA tag; % Ctrl=0 (zero) indicates a complete inhibition of the kinase tested by a concentration of 1 μM inhibitor (Fabian, M. A. et al. A small molecule-kinase interaction map for clinical kinase inhibitors. Nat. Biotechnol. 23, 329-336 (2005) and Karaman, M. W. et al. A quantitative analysis of kinase inhibitor selectivity. Nat. Biotechnol. 26, 127-132 (2008)).

TABLE 2

Kinome affinity scan for A51 (WXL5846)

| Gene Symbol | Target WXL05846 A51 % Ctrl 1000 nM |
|---|---|
| ERK1 | 94 |
| ERK2 | 71 |

TABLE 2-continued

Kinome affinity scan for A51 (WXL5846)

| Gene Symbol | Target WXL05846 A51 % Ctrl 1000 nM |
|---|---|
| FAK | 91 |
| FGFR2 | 94 |
| FGFR3 | 100 |
| FLT3 | 89 |
| FLT3(ITD) | 57 |
| GSK3A | 3.3 |
| GSK3B | 5 |
| IGF1R | 100 |
| IKK-alpha | 87 |
| IKK-beta | 77 |
| INSR | 93 |
| IRAK1 | 0 |
| IRAK4 | 67 |
| CSNK1A1 | 1.9 |
| CSNK1A1L | 0.5 |
| CSNK1D | 2.8 |
| CSNK1E | 0.1 |
| CSK1G2 | 0.7 |
| CSNK2A1 | 22 |

Table 3 shows the Kd measurements for the interaction of A14 (WXL-4085) and A51 (WXL-5846) with IRAK1

TABLE 3

Kd of A14 (WXL-4085) and A51 (WXL-5846) with IRAK1

| Gene Symbol | Target | |
|---|---|---|
| | WXL-4085-02N A14 Kd (nM) | WXL-5846 A51 Kd (nM) |
| IRAK1 | 11 | 2.9 |

Conclusion. IRAK1 as a superior target in a kinome scan shows zero binding of IRAK1 to its target in the presence of the inhibitors. Pyrazole pyrimidine compounds of the invention A51 and A14 showed excellent binding Kd to IRAK1. The compounds also showed inhibition of IRAK1 activation and inhibition of the activation of the IRAK1 target IKK (Ikappa B kinase) in RKO cells (Western blot analysis). It is to be noted that compound A51 showed complete (100%) inhibition of phospho-(active) IRAK1 at a concentration of 1 µM in the RKO cell line. As a comparison, Garrett W. Rhyasen et al. showed that Amgen's IRAK1-4 inhibitor used in the treatment of MDS and breast cancer inhibited only 70% of IRAK1/4 in cell lines at 10 µM (Garrett W. Rhyasen et al, 2013, Cancer Cell 24, 90-104, see especially FIG. 2 therein). Thus, compounds of the invention, such as A51, are found to be excellent inhibitors of IRAK1, an important upstream regulator of the NF-kB pathway which plays an important role in hematological malignancies (including among others multiple myeloma, MDS, leukemia and lymphoma, head and neck cancer and breast cancer).

Single-Dose Treatment Effect of a CKI Inhibitor in AML Mice and PD-L1 Expression.

Figure 12B:
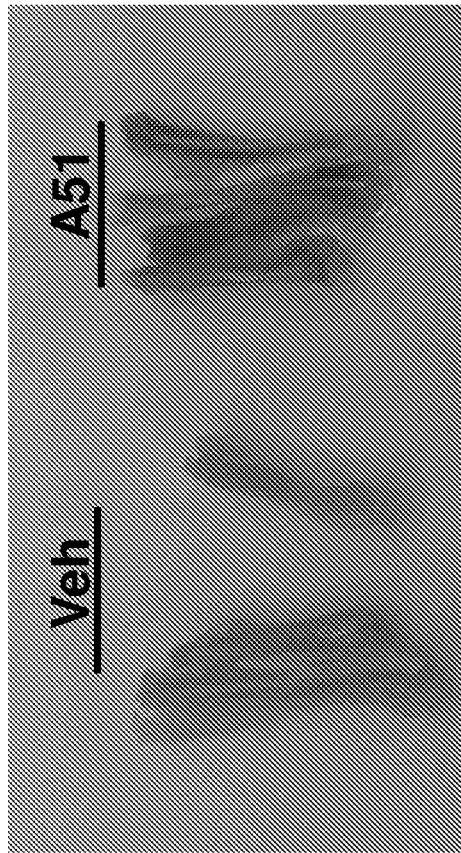
FIGS. 12A and 12B show pictures of spleen and bone from treated AML mice. Actual reduction in spleen size (splenomegaly) after treatment with A51, as disclosed above (FIG. 12A) and opaque bones turned to normal color following a single dose treatment (FIG. 12B).
Figure 12A:
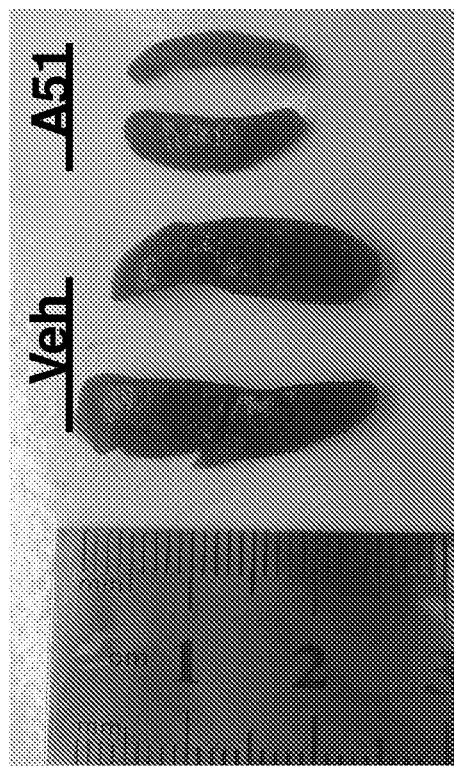

AML mice were prepared by inoculating MLL-AF9 oncogene-transduced bone marrow cells to C57/BL6 mice. MLL-AF9 fusion represents one of a poor prognosis human AML induced by chromosomal translocation. 30 days after leukemia inoculation, the recipient mice have high white blood cells (WBC) counts (×10 higher than a normal mouse), and harbor >95% leukemia blasts in the bone marrow and 50% of the peripheral WBC in these mice are AML blasts. These mice have splenomegaly and their bones are pale and fragile due to the acute leukemia (FIG. 12). Oral treatment with A51 (20 mg/Kg) for 16 hrs results in massive reduction of the total leukemia cells in the blood (FIG. 11B), shrinking of the leukemic spleen (FIG. 11C and FIG. 12A), 50% and >90% reduction of proportion of leukemic blasts (GFP+ cells) in the bone marrow and blood, respectively (FIG. 11D and FIG. 11E). Opaque bones turned to normal color following a single dose treatment (FIG. 12B).

In Vitro Treatment Effects of CKI Inhibitors on AML Cells Isolated from the Bone Marrow of Leukemic Mice.

Figure 13A:
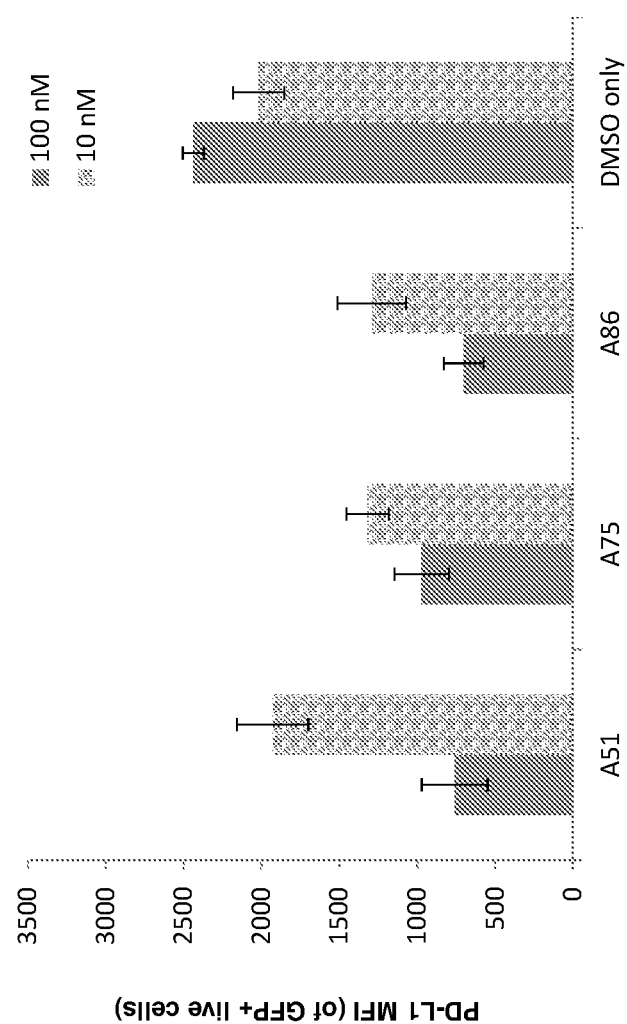
FIGS. 13A-13E show the results of in vitro treatment effects of CKI inhibitors on AML cells isolated from the bone marrow of leukemic mice. Shown are the percentage of dead cells (7AAD+) and the effects of the inhibitors on the expression of the major immune checkpoint protein PD-L1 in the leukemic cells; Inhibitor treatment was in 10 or 100 nM for several time points (5 hours,—FIG. 13A, 6 hours,—FIGS. 13B and 13C, and 9 hours FIGS. 13D and 13E).
Figure 13C:
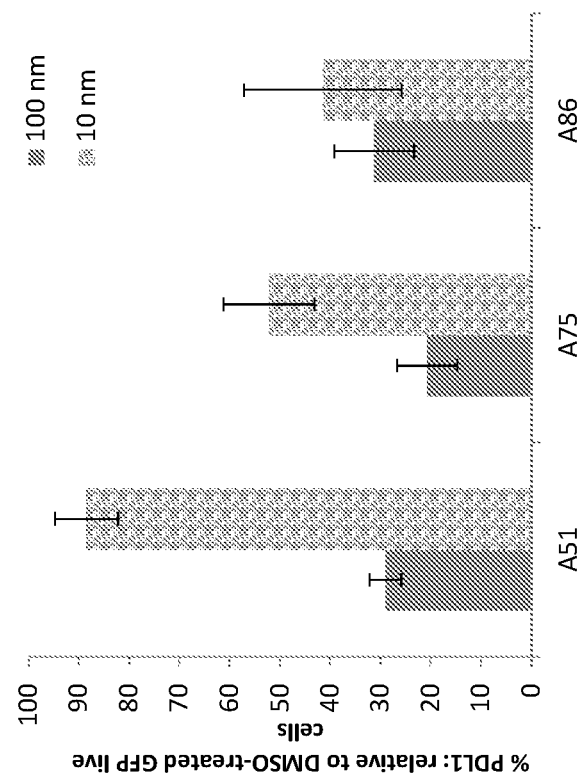
Figure 13B:
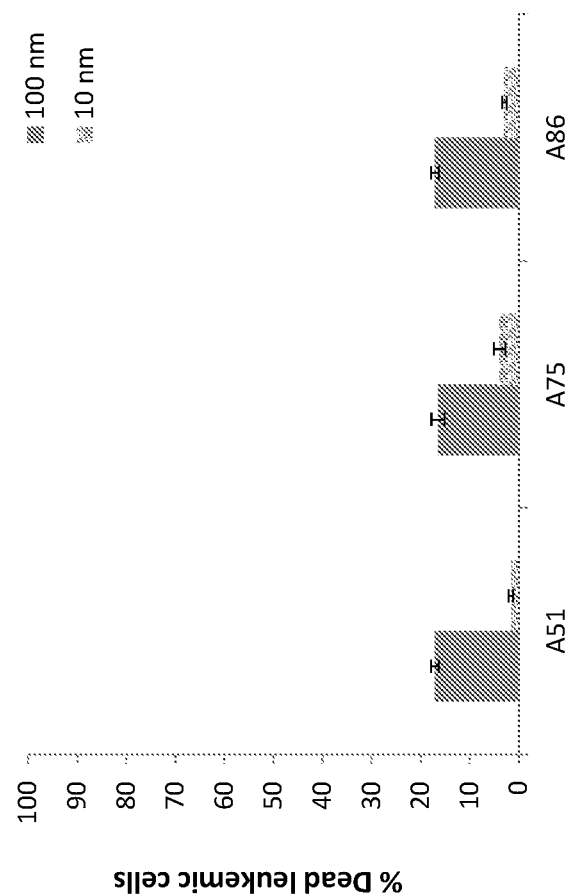
Figure 13E:
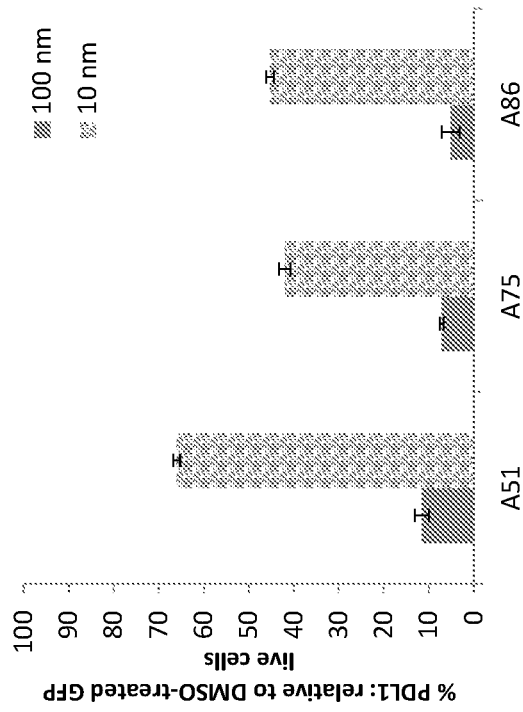
Figure 13D:
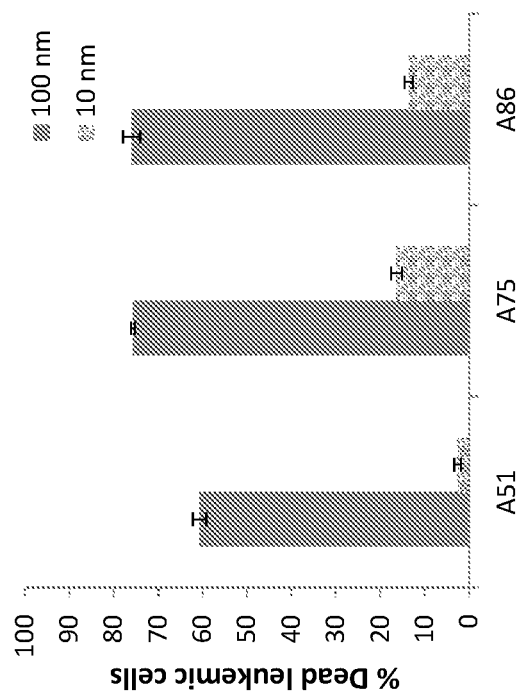

Shown are the percentage of dead cells (7AAD+) following 10 or 100 nM inhibitor-treatment, at 6 and 9 hours after treatment (FIGS. 13B and 13D). DMSO treatment resulted in <10% dead cells at 9 hrs. Also, shown are effects of the inhibitors on the leukemia expression of the major immune checkpoint protein PD-L1 by flow cytometry analysis: reduction of the mean fluorescence intensity (MFI) at 5 hrs, and a decrease in the fraction of PD-L1-positive leukemia cells after inhibitor treatment in comparison to DMSO-treated cells at 6 and 9 hours (decrease expressed by % of DMSO control) (FIGS. 13A, 13C and 13E).

The invention claimed is:

1. A method of inhibiting Casein kinase I in a subject, comprising administering to the subject a compound having formula (I), or a stereoisomer or a pharmaceutically acceptable salt thereof:

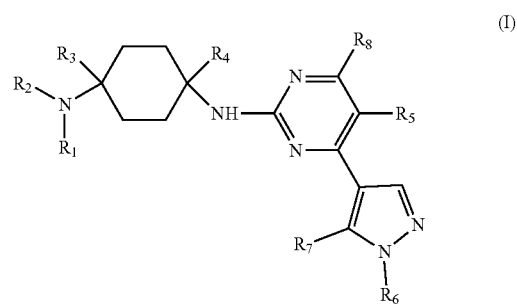

(I)

wherein:
$R_1$ and $R_2$ are each independently H; or straight or branched $C_1$-$C_8$ alkyl, straight or branched $C_1$-$C_5$ alkoxy, straight or branched $C_1$-$C_5$ acyl, $C_5$-$C_{15}$ aryl, or $C_3$-$C_7$ heteroaryl, each of which is optionally substituted by at least one of halide, hydroxyl, an ester, an ether, $C_5$-$C_{15}$ aryl, $C_3$-$C_7$ heteroaryl, and an amide; or $R_1$ and $R_2$ together with the nitrogen atom they are connected to form a 4-7 membered saturated, unsaturated, or aromatic ring that optionally includes at least one of N, O, NH, C=N, C=O, and SO$_2$, and is optionally substituted with at least one of straight or branched $C_1$-$C_8$ alkyl, $C_5$-$C_{15}$ aryl, $C_3$-$C_7$ heteroaryl, hydroxyl, halide, and cyano;

$R_3$ and $R_4$ are each independently H, or straight or branched $C_1$-$C_8$ alkyl optionally substituted by at least one of halide, hydroxyl, $C_1$-$C_5$ alkoxy, $C_5$-$C_{15}$ aryl, $C_3$-$C_7$ heteroaryl, an ester, and an amide; or $R_1$ or $R_2$ together with $R_3$ and the carbon and nitrogen atoms they are each connected to form a 4-7 membered saturated, unsaturated, or aromatic ring that optionally includes at least one of N, NH, O, C=N, C=O, and SO$_2$, and is optionally substituted with at least one of straight or branched $C_1$-$C_5$ alkyl, $C_5$-$C_{15}$ aryl, $C_3$-$C_7$ heteroaryl, hydroxyl, and halide;

$R_5$ and $R_8$ are each independently H or halide; or straight or branched $C_1$-$C_8$ alkyl, straight or branched $C_2$-$C_8$ alkenyl, or straight or branched $C_2$-$C_8$ alkynyl, each of which is optionally substituted by at least one halide;

$R_6$ is straight or branched $C_1$-$C_8$ alkyl, straight or branched $C_2$-$C_8$ alkenyl, straight or branched $C_2$-$C_8$ alkynyl, $C_5$-$C_{10}$ cycloalkyl, or saturated or unsaturated 4-6 membered heterocyclyl, each of which is optionally substituted by at least one of straight or branched $C_1$-$C_8$ alkyl, $C_3$-$C_7$ cycloalkyl, 4-6 membered heterocyclyl, $C_5$-$C_{15}$ aryl, $C_3$-$C_7$ heteroaryl, halide, hydroxyl, and $C_1$-$C_5$ alkyl halide; and $R_7$ is straight or branched $C_1$-$C_8$ alkyl, straight or branched $C_2$-$C_8$ alkenyl, or straight or branched $C_2$-$C_8$ alkynyl, each of which is substituted by at least one $C_3$-$C_7$ cycloalkyl, 4-6 membered heterocyclyl, $C_5$-$C_{15}$ aryl, $C_3$-$C_7$ heteroaryl, halide, hydroxyl, and $C_1$-$C_5$ alkyl halide.

2. The method of claim 1, wherein $R_1$ is H; or straight or branched $C_1$-$C_8$ alkyl, $C_5$-$C_{15}$ aryl, or $C_3$-$C_7$ heteroaryl, each of which is optionally substituted by at least one of halide, hydroxyl, an ester, an ether, $C_5$-$C_{15}$ aryl, $C_3$-$C_7$ heteroaryl, and an amide.

3. The method of claim 1, wherein $R_1$ is H.

4. The method of claim 1, wherein $R_2$ is H; or straight or branched $C_1$-$C_8$ alkyl, $C_5$-$C_{15}$ aryl, or $C_3$-$C_7$ heteroaryl, each of which is optionally substituted by at least one of halide, hydroxyl, an ester, an ether, $C_5$-$C_{15}$ aryl, $C_3$-$C_7$ heteroaryl, and an amide.

5. The method of claim 1, wherein $R_2$ is H.

6. The method of claim 1, wherein $R_1$ and $R_2$ together with the nitrogen atom they are connected to form a 4-7 membered saturated, unsaturated, or aromatic ring that optionally includes at least one of N, O, NH, C=N, C=O, and $SO_2$, and is optionally substituted with at least one of straight or branched $C_1$-$C_5$ alkyl, $C_5$-$C_{15}$ aryl, $C_3$-$C_7$ heteroaryl, hydroxyl, halide, and cyano.

7. The method of claim 1, wherein $R_1$ together with $R_3$ and the carbon and nitrogen atoms they are each connected to form a 4-7 membered saturated, unsaturated, or aromatic ring that optionally includes at least one of N, NH, 0, C=N, C=O, and $SO_2$, and is optionally substituted with at least one of straight or branched $C_1$-$C_5$ alkyl, $C_5$-$C_{15}$ aryl, $C_3$-$C_7$ heteroaryl, hydroxyl, and halide.

8. The method of claim 1, wherein $R_3$ is H, or straight or branched $C_1$-$C_8$ alkyl optionally substituted by at least one of halide, hydroxyl, $C_1$-$C_5$ alkoxy, $C_5$-$C_{15}$ aryl, $C_3$-$C_7$ heteroaryl, an ester, and an amide.

9. The method of claim 1, wherein $R_3$ is H.

10. The method of claim 1, wherein $R_4$ is H, or straight or branched $C_1$-$C_8$ alkyl optionally substituted by at least one of halide, hydroxyl, $C_1$-$C_5$ alkoxy, $C_5$-$C_{15}$ aryl, $C_3$-$C_7$ heteroaryl, an ester, and an amide.

11. The method of claim 1, wherein $R_4$ is H.

12. The method of claim 1, wherein $R_5$ is selected from H, Cl, and straight or branched $C_1$-$C_4$ alkyl.

13. The method of claim 1, wherein $R_5$ is H.

14. The method of claim 1, wherein $R_6$ is straight or branched $C_1$-$C_8$ alkyl, or saturated, unsaturated, or aromatic 4-6 membered heterocyclyl, each optionally substituted by at least one of straight or branched $C_1$-$C_8$ alkyl, $C_3$-$C_7$ cycloalkyl, halide, hydroxyl, and $CF_3$.

15. The method of claim 1, wherein $R_6$ is straight or branched $C_1$-$C_8$ alkyl.

16. The method of claim 1, wherein $R_6$ is methyl.

17. The method of claim 1, wherein $R_7$ is straight or branched $C_1$-$C_8$ alkyl substituted by at least one of $C_3$-$C_7$ cycloalkyl and hydroxyl.

18. The method of claim 1, wherein $R_8$ is selected from H, Cl, and straight or branched $C_1$-$C_4$ alkyl.

19. The method of claim 1, wherein $R_8$ is H.

20. The method of claim 1, wherein the compound is:

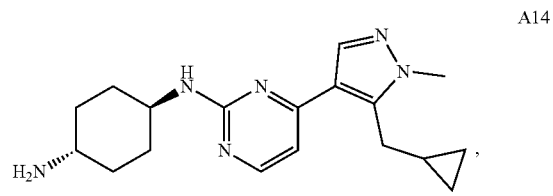

A14,

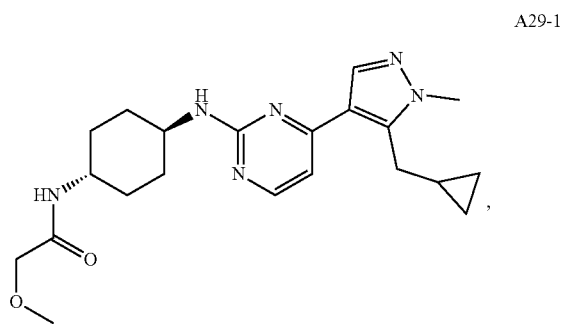

A29-1,

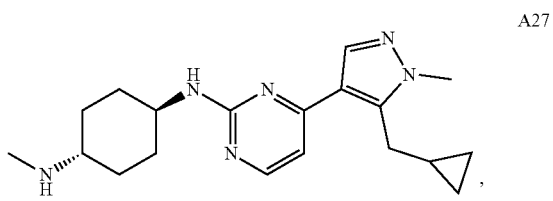

A27,

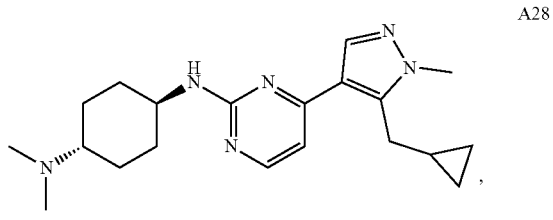

A28,

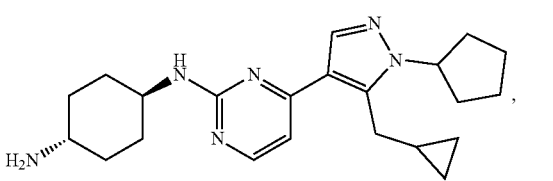

A36,

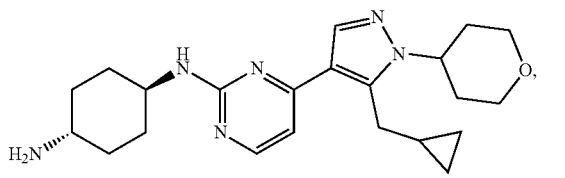

A39,

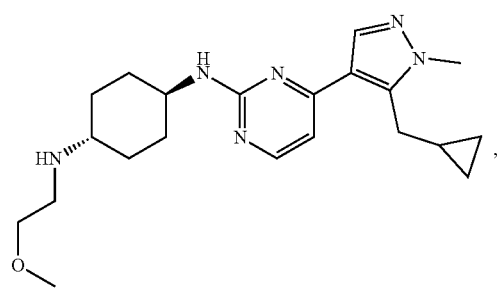
A29
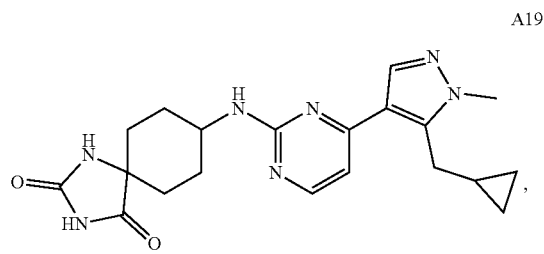
A19-4
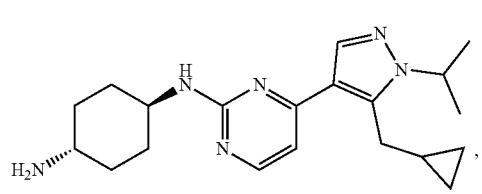
A35
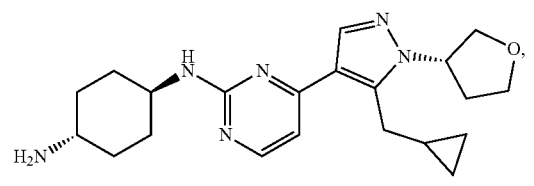
A41
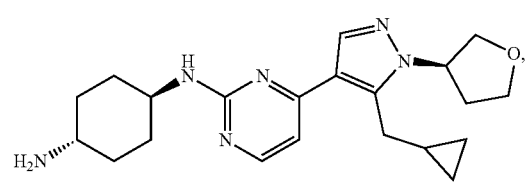
A42
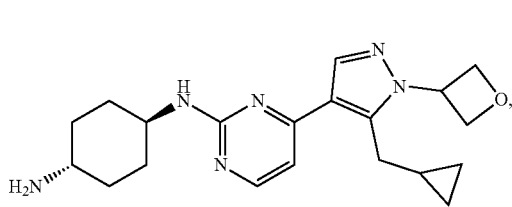
A43
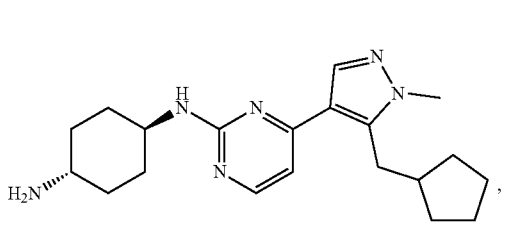
A46
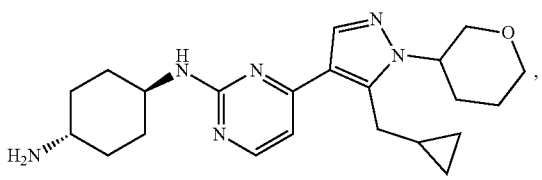
A38
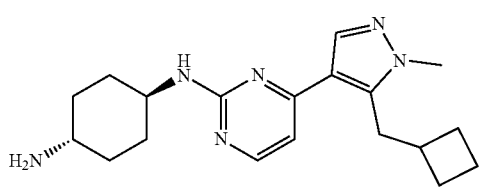
A45
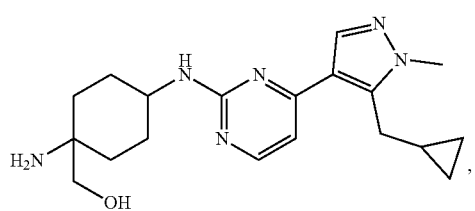
A19
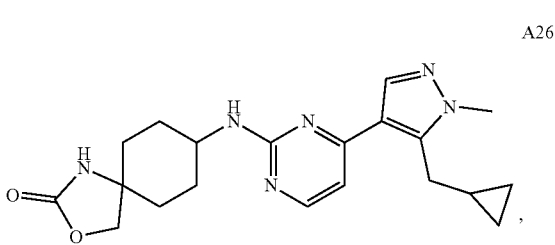
A26
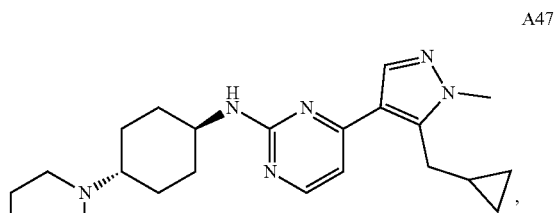
A47
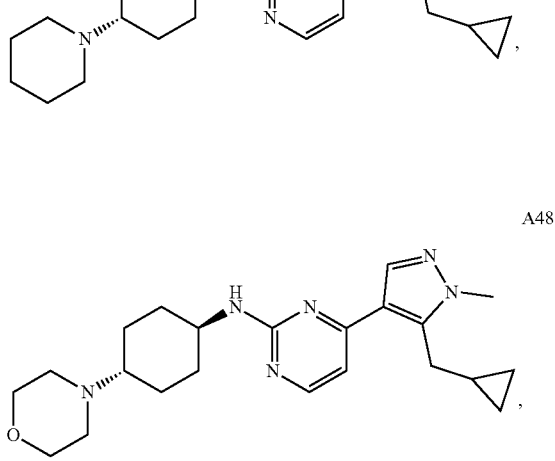
A48

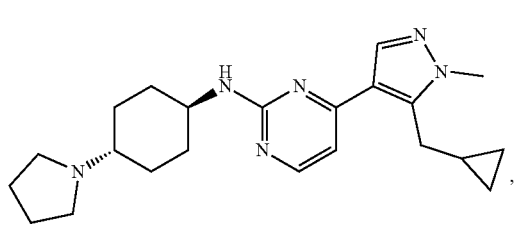 A49
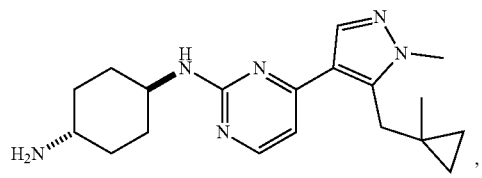 A56
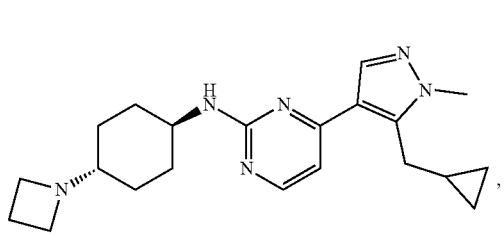 A50
A57
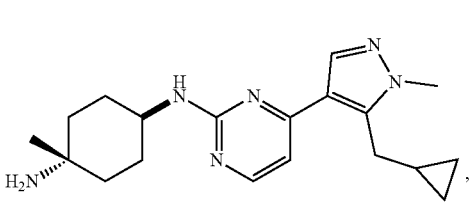 A30-1
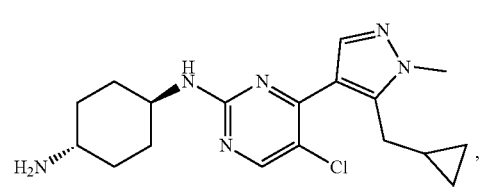 A51
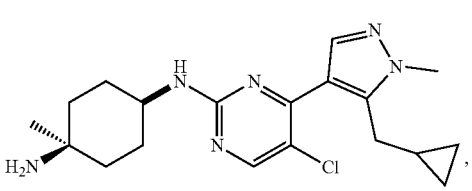 A30-2
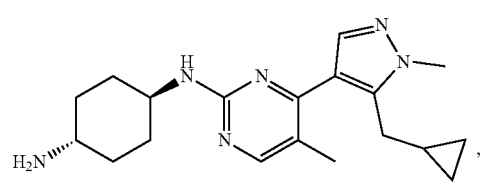 A52
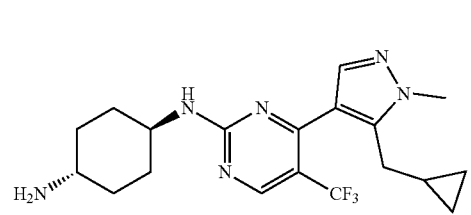 A60
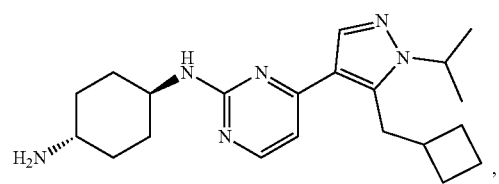 A53
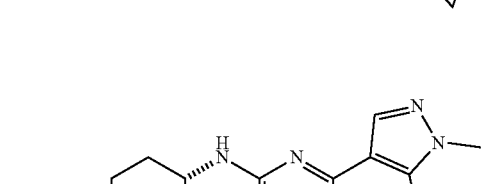 A64
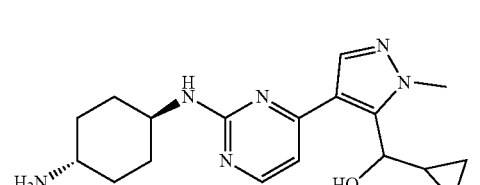 A58
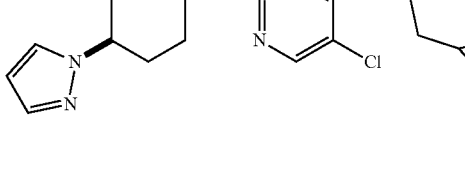 A65
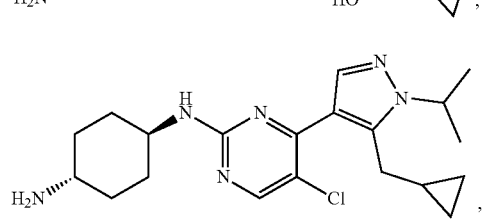 A59

-continued
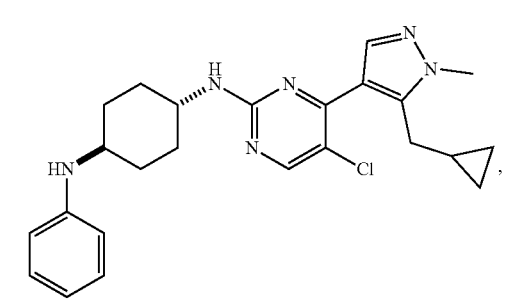
A68
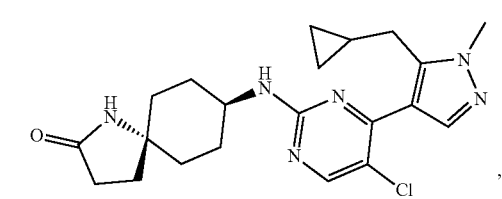
A71
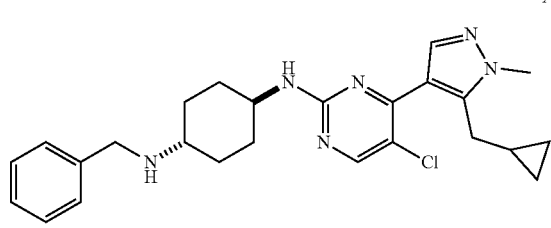
A74
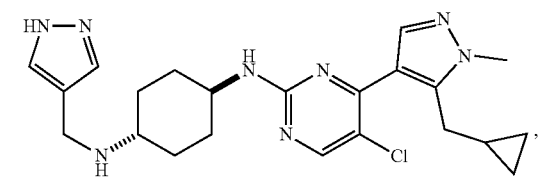
A75
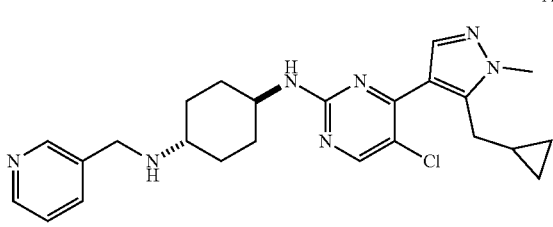
A76
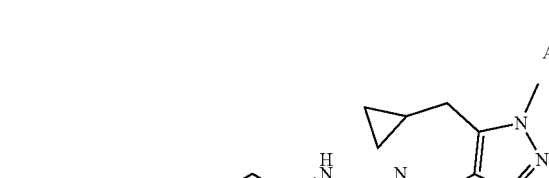
A80
-continued
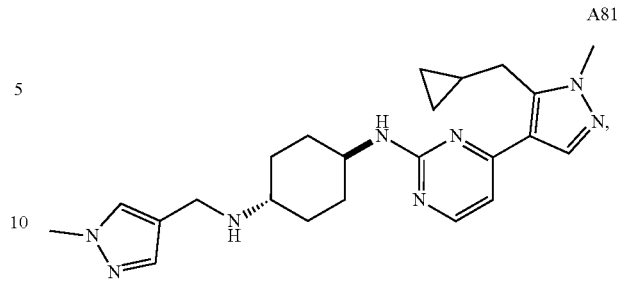
A81
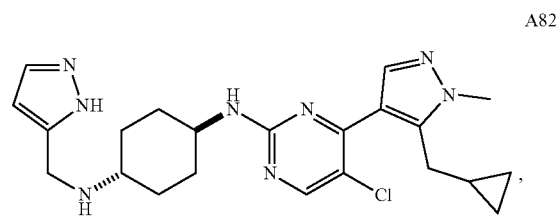
A82
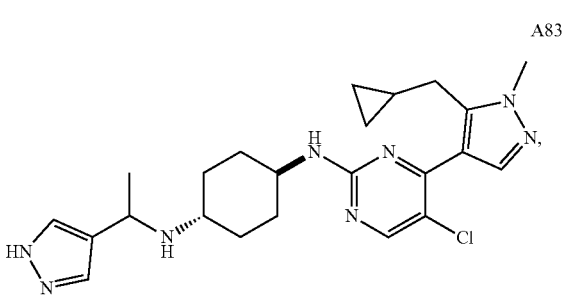
A83
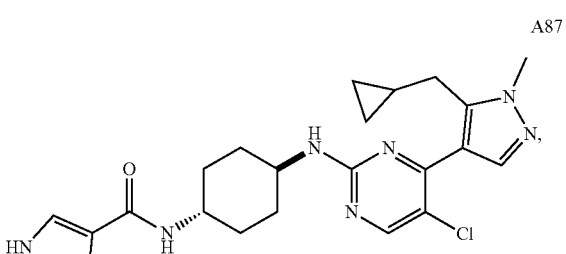
A87
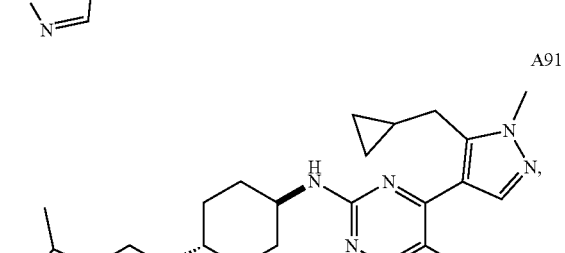
A91
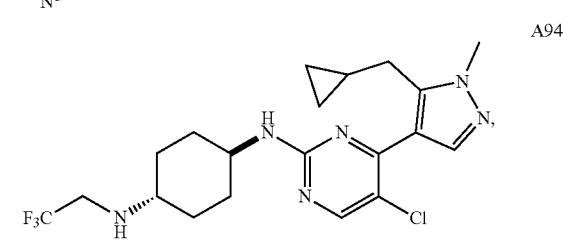
A94

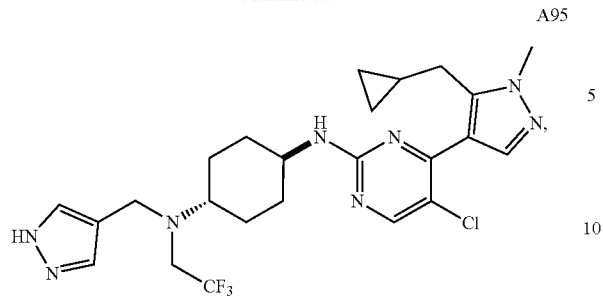
or a pharmaceutically acceptable salt thereof.
* * * * *